United States Patent
Kumamoto et al.

(10) Patent No.: US 8,263,628 B2
(45) Date of Patent: Sep. 11, 2012

(54) FLUORINE-CONTAINING ORGANOSULFUR COMPOUND AND PESTICIDAL COMPOSITION THEREOF

(75) Inventors: Koji Kumamoto, Toyonaka (JP); Hiroyuki Miyazaki, Takarazuka (JP)

(73) Assignee: Sumitomo Chemical Company, Limited., Tokyo (JP)

( * ) Notice: Subject to any disclaimer, the term of this patent is extended or adjusted under 35 U.S.C. 154(b) by 181 days.

(21) Appl. No.: 12/674,531

(22) PCT Filed: Aug. 22, 2008

(86) PCT No.: PCT/JP2008/065471
§ 371 (c)(1),
(2), (4) Date: Feb. 22, 2010

(87) PCT Pub. No.: WO2009/025397
PCT Pub. Date: Feb. 26, 2009

(65) Prior Publication Data
US 2011/0124651 A1    May 26, 2011

(30) Foreign Application Priority Data
Aug. 23, 2007    (JP) ................................. 2007-217209

(51) Int. Cl.
*A61K 31/44*    (2006.01)
*C07D 213/00*    (2006.01)
(52) U.S. Cl. ........................................ 514/357; 546/339
(58) Field of Classification Search .................. 546/339; 514/357
See application file for complete search history.

(56) References Cited

U.S. PATENT DOCUMENTS
5,438,033 A * 8/1995 Drumm et al. ................ 504/130

FOREIGN PATENT DOCUMENTS
JP          2005-179321 A     7/2005
WO    WO 2008/143332 A1    11/2008

OTHER PUBLICATIONS

Abe et al. CAS: 151:56879, 2009.*
Drumm et al. CAS: 123: 191221, 1995.*
Chinese Office Action dated Jul. 21, 2011 for Application No. 200880112857.5.
International Preliminary Report on Patentability (Form PCT/IB/373) and Written Opinion of the International Searching Authority (Form PCT/ISA/237) issued in PCT/JP2008/065471 (dated Feb. 24, 2010).
Database WPI Week 200560, Thomson Scientific, London, GB, AN 2005-585455, XP002508065.
Office Action for corresponding Egyptian Patent Application No. 2010020301, dated Dec. 1, 2011.

* cited by examiner

*Primary Examiner* — Rei-tsang Shiao
(74) *Attorney, Agent, or Firm* — Birch Stewart Kolasch & Birch, LLP

(57) ABSTRACT

There is provided a fluorine-containing organosulfur compound having an excellent control effect on harmful arthropods, which is represented by the formula (I): wherein m represents 0 or 1; n represents 0, 1 or 2; A represents an optionally substituted 6-membered aromatic heterocyclic group; $R_1$ to $R_4$ are the same or different and represent a hydrogen atom, a C1-C4 chain hydrocarbon group optionally substituted with a halogen atom, etc.; and Q represents a C1-C5 haloalkyl group containing at least one fluorine atom, or a fluorine atom.

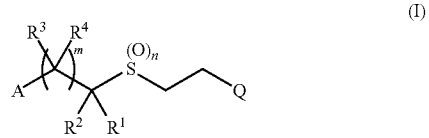

(I)

9 Claims, No Drawings

FLUORINE-CONTAINING ORGANOSULFUR COMPOUND AND PESTICIDAL COMPOSITION THEREOF

TECHNICAL FIELD

The present invention relates to a fluorine-containing sulfur compound and a pesticidal composition thereof.

BACKGROUND ART

A number of pesticidal compositions have hitherto been developed and served for practical use. Further, JP 2005-179321 A discloses a halogen-containing organosulfur compound.

DISCLOSURE OF THE INVENTION

An object of the present invention is to provide a novel compound which has an excellent control effect on pests, and applications thereof.

The present inventors have intensively studied so as to find out a compound having an excellent controlling effect on pests and found that a fluorine-containing organosulfur compound represented by the formula (I) below had an excellent controlling effect on pests such as harmful insects and ticks. Thus the present invention has been completed.

That is, the present invention provides:

(1) A fluorine-containing organosulfur compound represented by the formula (I):

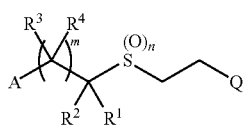

(I)

wherein m represents 0 or 1;
n represents 0, 1 or 2;
A represents a 6-membered aromatic heterocyclic group optionally substituted with a group of the groups E1 to E2;
$R^1$ and $R^3$ are the same or different and represent a C1-C4 chain hydrocarbon group optionally substituted with a halogen atom, a $-C(=G)R^5$ group, a cyano group, a halogen atom or a hydrogen atom;
$R^2$ and $R^4$ are the same or different and represent a C1-C4 chain hydrocarbon group optionally substituted with a halogen atom, a halogen atom, or a hydrogen atom;
Q represents a C1-C5 haloalkyl group containing at least one fluorine atom, or a fluorine atom;
G represents an oxygen atom or a sulfur atom;
$R^5$ represents a C1-C4 alkyl group optionally substituted with a halogen atom, a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, or a hydrogen atom;
the group E1 is a monovalent group selected from the group consisting of a C1-C6 chain hydrocarbon group optionally substituted with a group of the group L, a C3-C6 cycloalkyl group optionally substituted with a halogen atom, $-OR^6$, $-SR^6$, $-S(=O)R^6$, $-S(=O)_2R^6$, $-C(=O)R^7$, $-OC(=O)R^8$, a halogen atom, a cyano group, a nitro group and a hydroxyl group;
the group E2 is a divalent group selected from the group consisting of a C2-C6 alkanediyl group optionally substituted with a group of the group L, a 1,3-butadiene-1,4-diyl group optionally substituted with a group of the group L, -G-T-G- and -T-G-T-;
T represents a methylene group or an ethylene group;
$R^6$ represents a C1-C4 chain hydrocarbon group optionally substituted with a halogen atom or a C3-C6 cycloalkyl group optionally substituted with a halogen atom;
$R^7$ represents a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, a C1-C4 alkyl group optionally substituted with a halogen atom, or a hydrogen atom;
$R^8$ represents a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, a C1-C4 alkyl group optionally substituted with a halogen atom, or a hydrogen atom; and
the group L is a monovalent group selected from the group consisting of a hydroxyl group, $-OR^6$, $-SR^6$, $-S(=O)R^6$, $-S(=O)_2R^6$, $-C(=O)R^7$, $-OC(=O)R^8$, a cyano group, a nitro group and a halogen atom (hereinafter, sometimes, referred to as the present compound);

(2) The fluorine-containing organosulfur compound according to the above (1), wherein m is 0;

(3) The fluorine-containing organosulfur compound according to the above (1), wherein m is 1;

(4) The fluorine-containing organosulfur compound according to any one of the above (1) to (3), wherein n is 0;

(5) The fluorine-containing organosulfur compound according to any one of the above (1) to (3), wherein n is 1 or 2;

(6) The fluorine-containing organosulfur compound according to any one of the above (1) to (5), wherein A represents a pyridyl group, a pyridazinyl group, a pyrimidinyl group or a pyrazinyl group, and the pyridyl group, the pyridazinyl group, the pyrimidinyl group or the pyrazinyl group may be substituted with a group of the groups E1 to E2;

(7) The fluorine-containing organosulfur compound according to any one of the above (1) to (5), wherein A represents a pyridyl group optionally substituted with a group E3, a pyridazinyl group optionally substituted with a group E3, a pyrimidinyl group optionally substituted with a group E3, or a pyrazinyl group optionally substituted with a group E3, and the group E3 is a monovalent group selected from the group consisting of a halogen atom, a trifluoromethyl group, a pentafluoroethyl group, an ethynyl group, a cyano group, a nitro group, a trifluoromethoxy group, a trifluoromethylthio group, a trifluoromethanesulfinyl group, a trifluoromethanesulfonyl group, a methylthio group, a methanesulfinyl group and a methanesulfonyl group;

(8) A pesticidal composition comprising the fluorine-containing organosulfur compound according to any one of the above (1) to (7) as an active ingredient; and (9) A pest control method which comprises applying an effective amount of the compound according to any one of the above (1) to (7) to pests or habitats of the pests.

BEST MODE FOR CARRYING OUT THE INVENTION

In the present invention, the description such as "C1-C4" denotes a total number of carbon atoms that constitute each substituent group.

Examples of a "halogen atom" include a fluorine atom, a chlorine atom and a bromine atom.

Examples of the 6-membered aromatic heterocyclic group include pyridyl groups such as a 2-pyridyl group, a 3-pyridyl group and a 4-pyridyl group; pyridazinyl groups such as a 3-pyridazinyl group and a 4-pyridazinyl group;
pyrimidinyl groups such as a 2-pyrimidinyl group, a 4-pyrimidinyl group and a 5-pyrimidinyl group;
pyrazinyl groups such as a 2-pyrazinyl group; 1,2,4-triazinyl groups such as a 1,2,4-triazin-3-yl group, a 1,2,4-triazin-5-yl group and a 1,2,4-triazin-6-yl group; and 1,3,5-triazinyl groups such as a 1,3,5-triazin-2-yl group.

Specific examples of the "6-membered aromatic heterocyclic group optionally substituted with a group of the groups E1 to E2" are as follows.

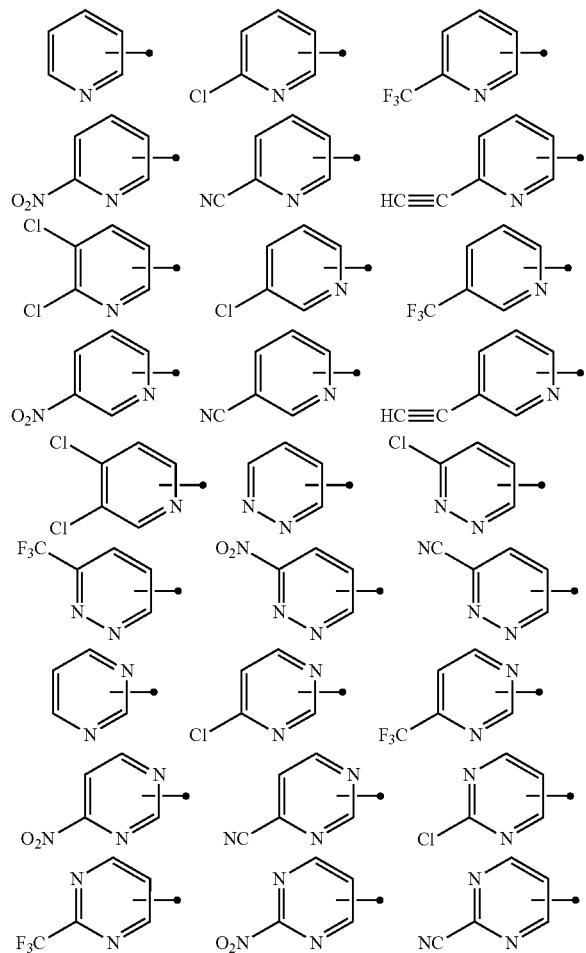

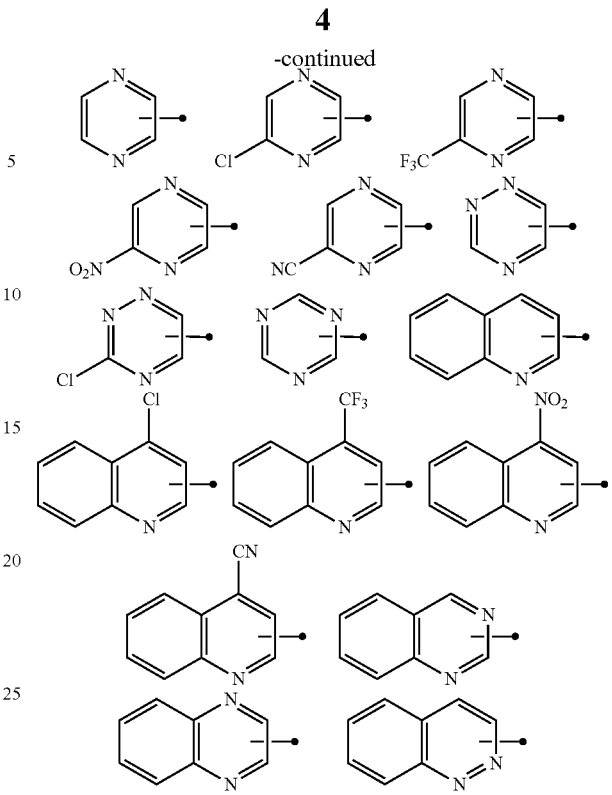

Examples of the "C1-C4 chain hydrocarbon group optionally substituted with a halogen atom" include C1-C4 alkyl groups which may be substituted with a halogen atom such as a methyl group, an ethyl group, a propyl group, a 1-methylethyl group (hereafter, sometimes, referred to as an i-propyl group), a 1,1-dimethylethyl group (hereafter, sometimes, referred to as a t-butyl group), a chloromethyl group, a fluoromethyl group, a difluoromethyl group, a trifluoromethyl group, a 2,2,2-trifluoroethyl group, a 1,1,2,2-tetrafluoroethyl group and a 1,1,2,2,2-pentafluoroethyl group; C2-C4 alkenyl groups which may be substituted with a halogen atom such as a vinyl group, a 2,2-difluorovinyl group, a 1,2,2-trifluorovinyl group, a 1-propenyl group, a 2-propenyl group, a 3,3-difluoro-2-propenyl group, a 1-methyl-2-propenyl group, a 2-methyl-2-propenyl group, a 1-butenyl group and 2-butenyl group; and C2-C4 alkynyl groups which may be substituted with a halogen atom such as an ethynyl group, a 1-propynyl group, a 3,3,3-trifluoro-1-propynyl group, a 2-propynyl group, a 1-methyl-2-propynyl group, a 1-butynyl group, a 2-butynyl group and a 3-butynyl group.

Examples of the "C1-C5 haloalkyl group containing at least one fluorine atom" include a fluoromethyl group, a difluoromethyl group, a trifluoromethyl group, a 1-fluoroethyl group, a 2-fluoroethyl group, a 1,1-difluoroethyl group, a 2,2-difluoroethyl group, a 2,2,2-trifluoroethyl group, a 1,1,2,2,2-pentafluoroethyl group, a 1-fluoropropyl group, a 1,1-difluoropropyl group, a 2-fluoropropyl group, a 2,2-difluoropropyl group, a 3-fluoropropyl group, a 3,3-difluoropropyl group, a 3,3,3-trifluoropropyl group, a 1,1,2,2,3,3,3-heptafluoropropyl group, a 2,2,3,3,3-pentafluoropropyl group, a 2,2,2-trifluoro-(1-trifluoromethyl)ethyl group, a 1,2,2,2-tetrafluoro-trifluoro-(1-trifluoromethyl)ethyl group, a 2,2,3,3-tetrafluoropropyl group, a 1-fluorobutyl group, a 1,1-difluorobutyl group, a 2-fluorobutyl group, a 2,2-difluorobutyl group, a 3-fluorobutyl group, a 3,3-difluorobutyl group, a 4-fluorobutyl group, a 4,4-difluorobutyl group, a 4,4,4-trifluorobutyl group, a 3,3,4,4,4-pentafluorobutyl group, a 2,2, 3,4,4-pentafluorobutyl group, a 2,2,3,3,4,4,4-heptafluorobutyl group, a 1-fluoropentyl group, a 1,1-difluoropentyl group, a 2-fluoropentyl group, a 2,2-difluoropentyl group, a 3-fluoropentyl group, a 3,3-difluoropentyl group, a 4-fluoropentyl group, a 4,4-difluoropentyl group, a 5-fluoropentyl group, a 5,5-difluoropentyl group, a 5,5,5-trifluoropentyl group, a 4,4,5,5,5-pentafluoropentyl group, a 3,3,4,4,5,5,5-heptafluoropentyl group, a 2,2,3,3,4,4,5,5-octafluoropentyl group and a 2,2,3,3,4,4,5,5,5-nonafluoropentyl group.

Examples of the "C1-C4 alkyl group optionally substituted with a halogen atom" include a methyl group, an ethyl group, a 1-ethylethyl group, a 1,1-dimethylethyl group, a propyl group, an isopropyl group, a 1-methylpropyl group, a butyl group, a fluoromethyl group, a chloromethyl group, a bromomethyl group, an iodomethyl group, a difluoromethyl group, a chlorodifluoromethyl group, a bromodifluoromethyl group, a trifluoromethyl group, a dichloromethyl group, a trichloromethyl group, a 1-chloroethyl group, a 1-bromoethyl group, a 1-fluoroethyl group, a 2-chloroethyl group, a 2-bromoethyl group, a 2-fluoroethyl group, a 2,2-difluoroethyl group, a 2,2,2-trifluoroethyl group, a 2,2,2-trichloroethyl group, a pentafluoroethyl group, a 2,2,2-trifluoro-1-chloroethyl group, a 3-fluoropropyl group, a 3-chloropropyl group, a 1-fluoro-1-methylethyl group, a 1-chloro-1-methylethyl group, a 2-chloro-1,1-dimethylethyl group, a 2-fluoro-1,1-dimethylethyl group, a heptafluoropropyl group, a 1,1,2,2,3,3-hexafluoropropyl group, a 4-chlorobutyl group and a 4-fluorobutyl group.

Examples of the "C1-C4 alkoxy group optionally substituted with a halogen atom" include a methoxy group, an ethoxy group, a propoxy group, a trifluoromethoxy group, a bromodifluoromethoxy group, a difluoromethoxy group, a chlorodifluoromethoxy group, a pentafluoroethoxy group, a 2,2,2-trifluoroethoxy group and a 1,1,2,2-tetrafluoroethoxy group.

Examples of the "C3-C6 alkenyloxy group optionally substituted with a halogen atom" include a 1-propenyloxy group, a 2-propenyloxy group, a 1-methyl-2-propenyloxy group, a 1,1-dimethyl-2-propenyloxy group and a 2,2-difluoro-2-propenyloxy group.

Examples of the "C3-C6 alkynyloxy group optionally substituted with a halogen atom" include a 2-propynyloxy group, a 1-methyl-2-propynyloxy group, a 1,1-dimethyl-2-propynyloxy group, a 2-butynyloxy group, a 1-methyl-2-butynyloxy group, a 1,1-dimethyl-2-butynyloxy group and a 3,3,3-trifluoro-1-propynyloxy group.

Examples of the "C1-C4 alkylamino group optionally substituted with a halogen atom" include an N-methylamino group, an N-ethylamino group, an N-propylamino group, an N-(1-methylethyl)amino group and an N-(2,2,2-trifluoroethyl)amino group.

Examples of "a di(C1-C4 alkyl)amino group optionally substituted with a halogen atom" include an N,N-dimethylamino group, an N-ethyl-N-methylamino group, an N,N-diethylamino group, an N-methyl-N-propylamino group, an N-ethyl-N-propylamino group, an N,N-dipropylamino group, an N-methyl-N-(1-methylethyl)amino group, an N-ethyl-N-(1-methylethyl)amino group, an N,N-di(1-methylethyl)amino group, an N-methyl-N-(2,2,2-trifluoroethyl)amino group and an N-methyl-N-ethyl-N-(2,2,2-trifluoroethyl)amino group.

Examples of the "C2-C5 cyclic amino group" include a 1-azylidino group, a 1-azetidinyl group, a 1-pyrrolidinyl group, a piperidino group and a morphorino group.

Examples of the "C1-C6 chain hydrocarbon group optionally substituted with a group of the group L" include a C1-C6 alkyl group optionally substituted with a group of the group L, a C2-C6 alkenyl group optionally substituted with a group of the group L, and a C2-C6 alkynyl group optionally substituted with a group of the group L.

Examples of the "C1-C6 alkyl group optionally substituted with a group of the group L" include C1-C6 alkyl groups which may be substituted with a halogen atom such as a methyl group, an ethyl group, a propyl group, a 1-methylethyl group, a 2,2-dimethylpropyl group, a chloromethyl group, a fluoromethyl group, a difluoromethyl group, a trifluoromethyl group, a 2,2,2-trifluoroethyl group, a 1,1,2,2-tetrafluoroethyl group, a 1,1,2,2,2-pentafluoroethyl group and a 1,1-dimethylethyl group; (C1-C4 alkoxy)C1-C4 alkyl groups which may be substituted with a halogen atom such as a methoxymethyl group, an ethoxymethyl group, a 1-methoxyethyl group, a 1-ethoxyethyl group and a trifluoromethoxymethyl group; (C3-C6 alkenyloxy)C1-C4 alkyl groups which may be substituted with a halogen atom such as a (1-propenyloxy)methyl group, a (2-propenyloxy)methyl group, a (1-methyl-2-propenyloxy)methyl group, a (1,1-dimethyl-2-propenyloxy)methyl group, a (2,2-difluoro-2-propenyloxy)methyl group, a 1-(1-propenyloxy)ethyl group, 1-(2-propenyloxy)ethyl group, a 1-(1-methyl-2-propenyloxy)ethyl group, a 1-(1,1-dimethyl-2-propenyloxy)ethyl group, a 1-(2,2-difluoro-2-propenyloxy)ethyl group, a 2-(1-propenyloxy)ethyl group, a 2-(2-propenyloxy)ethyl group, a 2-(1-methyl-2-propenyloxy)ethyl group, a 2-(1,1-dimethyl-2-propenyloxy)ethyl group and a 2-(2,2-difluoro-2-propenyloxy)ethyl group; (C3-C6 alkynyloxy)C1-C4 alkyl groups which may be substituted with a halogen atom such as a (2-propynyloxy)methyl group, a (1-methyl-2-propynyloxy)methyl group, a (1,1-dimethyl-2-propynyloxy)methyl group, a (2-butynyloxy)methyl group, a (1-methyl-2-butynyloxy)methyl group, a (1,1-dimethyl-2-butynyloxy)methyl group, a (3,3,3-trifluoro-1-propynyloxy)methyl group, a 1-(2-propynyloxy)ethyl group, a 1-(1-methyl-2-propynyloxy)ethyl group, a 1-(1,1-dimethyl-2-propynyloxy)ethyl group, a 1-(2-butynyloxy)ethyl group, a 1-(1-methyl-2-butynyloxy)ethyl group, a 1-(1,1-dimethyl-2-butynyloxy)ethyl group, a 1-(3,3,3-trifluoro-1-propynyloxy)ethyl group, a 2-(2-propynyloxy)ethyl group, a 2-(1-methyl-2-propynyloxy)ethyl group, a 2-(1,1-dimethyl-2-propynyloxy)ethyl group, a 2-(2-butynyloxy)ethyl group, 2-(1-methyl-2-butynyloxy)ethyl group, a 2-(1,1-dimethyl-2-butynyloxy)ethyl group and a 2-(3,3,3-trifluoro-1-propynyloxy)ethyl group; and (hydroxyl)C1-C4 alkyl group optionally substituted with a halogen atom such as a hydroxymethyl group, a 1-hydroxyethyl group, a 1-hydroxy-1-methylethyl group, a 2-hydroxyethyl group and a 2-hydroxy-1-methylethyl group.

Examples of the "C2-C6 alkenyl group optionally substituted with a group of the group L" include C2-C6 alkenyl groups which may be substituted with a halogen atom such as a vinyl group, a 2,2-difluorovinyl group, a 1,2,2-trifluorovinyl group, a 1-propenyl group, a 2-propenyl group, a 3,3-difluoro-2-propenyl group and a 1-methyl-2-propenyl group.

Examples of the "C2-C6 alkynyl group optionally substituted with a group of the group L" include ethynyl groups such as a 1-ethynyl group, a 2-bromoethynyl group, a 2-iodoethynyl and a 2-(methoxycarbonyl)ethynyl group;
a 1-propynyl group or a substituted 1-propynyl group such as a 3-fluoro-1-propynyl group, a 3,3-difluoro-1-propynyl group, a 3-(dimethylamino)-1-propynyl group, a 3,3,3-trifluoro-1-propynyl group, a 3-methoxy-1-propynyl group and a 3-(methoxycarbonyl)-1-propynyl group;
a 2-propynyl group or a substituted 2-propynyl group such as a 1-fluoro-2-propynyl group and a 1,1-difluoro-2-propynyl group;

a 1-butynyl group or a substituted 1-butynyl group such as a 4-fluoro-1-butynyl group, a 4-methoxy-1-butynyl group, a 4-(dimethylamino)-1-butynyl group and a 4-(methoxycarbonyl)-1-butynyl group;

a 2-butynyl group or a substituted 2-butynyl group such as a 4-fluoro-2-butynyl group, a 4-methoxy-2-butynyl group, 4-(dimethylamino)-2-butynyl and a 4-(methoxycarbonyl)-2-butynyl group;

a 3-butynyl group or a substituted 3-butynyl group such as a 1,1-difluoro-3-butynyl group;

a 1-pentynyl group or a substituted 1-pentynyl group such as a 5-fluoro-1-pentynyl group, a 5-methoxy-1-pentynyl group, a 5-(dimethylamino)-1-pentynyl group and a 5-(methoxycarbonyl)-1-pentynyl group; and a 2-pentynyl group or a substituted 2-pentynyl group such as a 5-fluoro-2-pentynyl group, a 5-methoxy-2-pentynyl group, a 5-(dimethylamino)-2-pentynyl group and a 5-(methoxycarbonyl)-2-pentynyl group.

Examples of the "C3-C6 cycloalkyl group optionally substituted with a halogen atom" include a cyclopropyl group, a 1-methylcyclopropyl group, a 2,2-dichlorocyclopropyl group, a 2,2-dichloro-1-methylcyclopropyl group, a 2,2-difluorocyclopropyl group, a 2,2-difluoro-1-methylcyclopropyl group, a cyclobutyl group, a cyclopentyl group and a cyclohexyl group.

Examples of the "C2-C6 alkanediyl group optionally substituted with a group of the group L" include an ethane-1,2-diyl group, a propane-1,2-diyl group, a propane-1,3-diyl group, a butane-1,4-diyl group, a 2,3-dichlorobutane-1,4-diyl group and a pentane-1,5-diyl group.

Examples of the "1,3-butadiene-1,4-diyl group optionally substituted with a group of the group L" include a 1,3-butadiene-1,4-diyl group, a 2,2-dimethyl-1,3-butadiene-1,4-diyl group, a 1-chloro-1,3-butadiene-1,4-diyl group, a 2-chloro-1,3-butadiene-1,4-diyl group, a 2,2-dichloro-1,3-butadiene-1,4-diyl group and a 1,4-dichloro-1,3-butadiene-1,4-diyl group.

Examples of the present compound include the following compounds:

a fluorine-containing organosulfur compound represented by the formula (I), wherein A represents a pyridyl group, a pyridazinyl group, a pyrimidinyl group or a pyrazinyl group, and the pyridyl group, the pyridazinyl group, the pyrimidinyl group or the pyrazinyl group may be substituted with a group of the groups E1 to E2;

a fluorine-containing organosulfur compound represented by the formula (I), wherein A represents a pyridyl group optionally substituted with a group of the groups E1 to E2;

a fluorine-containing organosulfur compound represented by the formula (I), wherein A represents a pyridazinyl group optionally substituted with a group of the groups E1 to E2;

a fluorine-containing organosulfur compound represented by the formula (I), wherein A represents a pyrimidinyl group optionally substituted with a group of the groups E1 to E2;

a fluorine-containing organosulfur compound represented by the formula (I), wherein A represents a pyrazinyl group optionally substituted with a group of the groups E1 to E2;

a fluorine-containing organosulfur compound represented by the formula (I), wherein A represents a 6-membered aromatic heterocyclic group optionally substituted with a group of the groups E1 to E2;

a fluorine-containing organosulfur compound represented by the formula (I), wherein A represents a 6-membered aromatic heterocyclic group optionally substituted with a group of the group E3, wherein the group E3 is a monovalent group selected from the group consisting of a halogen atom, a trifluoromethyl group, a pentafluoroethyl group, an ethynyl group, a cyano group, a nitro group, a trifluoromethoxy group, a trifluoromethylthio group, a trifluoromethanesulfinyl group, a trifluoromethanesulfonyl group, a methylthio group, a methanesulfinyl group and a methanesulfonyl group;

a fluorine-containing organosulfur compound represented by the formula (I), wherein A represents a pyridyl group, a pyridazinyl group, a pyrimidinyl group or a pyrazinyl group, and the pyridyl group, the pyridazinyl group, the pyrimidinyl group or the pyrazinyl group may be substituted with a group of the group E3;

a fluorine-containing organosulfur compound represented by the formula (I), wherein A represents a pyridyl group optionally substituted with a group of the group E3;

a fluorine-containing organosulfur compound represented by the formula (I), wherein A represents a pyridazinyl group optionally substituted with a group of the group E3;

a fluorine-containing organosulfur compound represented by the formula (I), wherein A represents a pyrimidinyl group optionally substituted with a group of the group E3;

A fluorine-containing organosulfur compound represented by the formula (I), wherein A represents a pyrazinyl group optionally substituted with a group of the group E3;

a fluorine-containing organosulfur compound represented by the formula (I), wherein each of $R^1$ and $R^2$ represents a hydrogen atom;

A fluorine-containing organosulfur compound represented by the formula (I), wherein $R^1$ represents a C1-C4 chain hydrocarbon group optionally substituted with a halogen atom, and $R^2$ represents a hydrogen atom;

a fluorine-containing organosulfur compound represented by the formula (I), wherein $R^1$ represents a C1-C4 alkyl group optionally substituted with a halogen atom, and $R^2$ represents a hydrogen atom;

a fluorine-containing organosulfur compound represented by the formula (I), wherein $R^1$ represents a methyl group, and $R^2$ represents a hydrogen atom;

a fluorine-containing organosulfur compound represented by the formula (I), wherein $R^1$ represents a C1-C4 chain hydrocarbon group optionally substituted with a halogen atom, and $R^2$ represents a halogen atom;

a fluorine-containing organosulfur compound represented by the formula (I), wherein $R^1$ represents a C1-C4 alkyl group optionally which may be substituted with a halogen atom, and $R^2$ represents a halogen atom;

a fluorine-containing organosulfur compound represented by the formula (I), wherein $R^1$ represents a methyl group, and $R^2$ represents a halogen atom;

a fluorine-containing organosulfur compound represented by the formula (I), wherein $R^1$ represents a C1-C4 chain hydrocarbon group optionally substituted with a halogen atom, and $R^2$ represents a methyl group;

a fluorine-containing organosulfur compound represented by the formula (I), wherein $R^1$ represents a C1-C4 alkyl group optionally substituted with a halogen atom, and $R^2$ represents a methyl group;

a fluorine-containing organosulfur compound represented by the formula (I), wherein each of $R^1$ and $R^2$ represents a methyl group;

a fluorine-containing organosulfur compound represented by the formula (I), wherein $R^1$ represents —C(=G)$R^5$, and $R^2$ represents a hydrogen atom;

a fluorine-containing organosulfur compound represented by the formula (I), wherein $R^1$ represents —C(=G)$R^5$, G represents an oxygen atom, and $R^2$ represents a hydrogen atom;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, and $R^2$ represents a hydrogen atom;

a fluorine-containing organosulfur compound represented by the formula (I), wherein $R^1$ represents —C(=G)$R^5$, G represents an oxygen atom, $R^5$ represents a methoxy group, and $R^2$ represents a hydrogen atom;

a fluorine-containing organosulfur compound represented by the formula (I), wherein $R^1$ represents —C(=G)$R^5$, G represents an oxygen atom, $R^5$ represents an amino group, and $R^2$ represents a hydrogen atom;

a fluorine-containing organosulfur compound represented by the formula (I), wherein $R^1$ represents a cyano group, and $R^2$ represents a hydrogen atom;

a fluorine-containing organosulfur compound represented by the formula (I), wherein $R^1$ represents —C(=G)$R^5$, and $R^2$ represents a halogen atom;

a fluorine-containing organosulfur compound represented by the formula (I), wherein $R^1$ represents —C(=G)$R^5$, G represents an oxygen atom, and $R^2$ represents a halogen atom;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, and $R^2$ represents a halogen atom;

a fluorine-containing organosulfur compound represented by the formula (I), wherein $R^1$ represents —C(=G)$R^5$, G represents an oxygen atom, $R^5$ represents a methoxy group, and $R^2$ represents a halogen atom;

a fluorine-containing organosulfur compound represented by the formula (I), wherein $R^1$ represents —C(=G)$R^5$, G represents an oxygen atom, $R^5$ represents an amino group, and $R^2$ represents a halogen atom;

a fluorine-containing organosulfur compound represented by the foliula (I), wherein $R^1$ represents a cyano group, and $R^2$ represents a halogen atom;

a fluorine-containing organosulfur compound represented by the formula (I), wherein $R^1$ represents —C(=G)$R^5$, and $R^2$ represents a methyl group;

a fluorine-containing organosulfur compound represented by the formula (I), wherein $R^1$ represents —C(=G)$R^5$, G represents an oxygen atom, and $R^2$ represents a methyl group;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, and $R^2$ represents a methyl group;

a fluorine-containing organosulfur compound represented by the formula (I), wherein $R^1$ represents —C(=G)$R^5$, G represents an oxygen atom, $R^5$ represents a methoxy group, and $R^2$ represents a methyl group;

a fluorine-containing organosulfur compound represented by the formula (I), wherein $R^1$ represents —C(=G)$R^5$, G represents an oxygen atom, $R^5$ represents an amino group, and $R^2$ represents a methyl group;

a fluorine-containing organosulfur compound represented by the formula (I), wherein $R^1$ represents a cyano group, and $R^2$ represents a methyl group;

a fluorine-containing organosulfur compound represented by the formula (I), wherein $R^1$ represents a halogen atom, and $R^2$ represents a hydrogen atom;

a fluorine-containing organosulfur compound represented by the formula (I), wherein each of $R^1$ and $R^2$ represents a halogen atom;

a fluorine-containing organosulfur compound represented by the formula (I), wherein m is 0;

a fluorine-containing organosulfur compound represented by the formula (I), wherein m is 1, and each of $R^3$ and $R^4$ represents a hydrogen atom;

a fluorine-containing organosulfur compound represented by the formula (I), wherein m is 1, $R^3$ represents a C1-C4 chain hydrocarbon group, and $R^4$ represents a hydrogen atom;

a fluorine-containing organosulfur compound represented by the formula (I), wherein m is 1, $R^3$ represents a C1-C4 alkyl group, and $R^4$ represents a hydrogen atom;

a fluorine-containing organosulfur compound represented by the formula (I), wherein m is 1, $R^3$ represents a methyl group, and $R^4$ represents a hydrogen atom;

a fluorine-containing organosulfur compound represented by the formula (I), wherein m is 1, and each of $R^3$ and $R^4$ represents a methyl group;

a fluorine-containing organosulfur compound represented by the formula (1), wherein each of $R^1$ and $R^2$ represents a hydrogen atom, and m is 0;

a fluorine-containing organosulfur compound represented by the formula (I), wherein $R^1$ represents a C1-C4 chain hydrocarbon group optionally substituted with a halogen atom, $R^2$ represents a hydrogen atom, and m is 0;

a fluorine-containing organosulfur compound represented by the formula (I), wherein $R^1$ represents a C1-C4 alkyl group optionally substituted with a halogen atom, $R^2$ represents a hydrogen atom, and m is 0;

a fluorine-containing organosulfur compound represented by the formula (I), wherein $R^1$ represents a methyl group, $R^2$ represents a hydrogen atom, and m is 0;

a fluorine-containing organosulfur compound represented by the formula (I), wherein $R^1$ represents a C1-C4 chain hydrocarbon group optionally substituted with a halogen atom, $R^2$ represents a halogen atom, and m is 0;

a fluorine-containing organosulfur compound represented by the formula (I), wherein $R^1$ represents a C1-C4 alkyl group optionally substituted with a halogen atom, $R^2$ represents a halogen atom, and m is 0;

a fluorine-containing organosulfur compound represented by the formula (I), wherein $R^1$ represents a methyl group, $R^2$ represents a halogen atom, and m is 0;

a fluorine-containing organosulfur compound represented by the formula (I), wherein $R^1$ represents a C1-C4 chain hydrocarbon group optionally substituted with a halogen atom, $R^2$ represents a methyl group, and m is 0;

a fluorine-containing organosulfur compound represented by the formula (I), wherein $R^1$ represents a C1-C4 alkyl group optionally substituted with a halogen atom, $R^2$ represents a methyl group, and m is 0;

a fluorine-containing organosulfur compound represented by the formula (I), wherein each of $R^1$ and $R^2$ represents a methyl group, and m is 0;

a fluorine-containing organosulfur compound represented by the formula (I), wherein $R^1$ represents —C(=G)$R^5$, $R^2$ represents a hydrogen atom, and m is 0;

a fluorine-containing organosulfur compound represented by the formula (I), wherein $R^1$ represents —C(=G)$R^5$, G represents an oxygen atom, $R^2$ represents a hydrogen atom, and in is 0;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, $R^2$ represents a hydrogen atom, and m is 0;

a fluorine-containing organosulfur compound represented by the formula (I), wherein le represents —C(=G)$R^5$, G represents an oxygen atom, $R^5$ represents a methoxy group, $R^2$ represents a hydrogen atom, and m is 0;

a fluorine-containing organosulfur compound represented by the formula (I), wherein $R^1$ represents —C(=G)$R^5$, G represents an oxygen atom, $R^5$ represents an amino group, $R^2$ represents a hydrogen atom, and m is 0;

a fluorine-containing organosulfur compound represented by the formula (I), wherein $R^1$ represents a cyano group, $R^2$ represents a hydrogen atom, and m is 0;

a fluorine-containing organosulfur compound represented by the formula (I), wherein $R^1$ represents —C(=G)$R^5$, $R^2$ represents a halogen atom, and m is 0;

a fluorine-containing organosulfur compound represented by the formula (I), wherein $R^1$ represents —C(=G)$R^5$, G represents an oxygen atom, $R^2$ represents a halogen atom, and m is 0;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, $R^2$ represents a halogen atom, and m is 0;

a fluorine-containing organosulfur compound represented by the formula (I), wherein $R^1$ represents —C(=G)$R^5$, G represents an oxygen atom, $R^5$ represents a methoxy group, $R^2$ represents a halogen atom, and m is 0;

a fluorine-containing organosulfur compound represented by the formula (I), wherein $R^1$ represents —C(=G)$R^5$, G represents an oxygen atom, $R^5$ represents an amino group, $R^2$ represents a halogen atom, and m is 0;

a fluorine-containing organosulfur compound represented by the formula (I), wherein $R^1$ represents a cyano group, $R^2$ represents a halogen atom, and m is 0;

a fluorine-containing organosulfur compound represented by the formula (I), wherein $R^1$ represents —C(=G)$R^5$, $R^2$ represents a methyl group, and m is 0;

a fluorine-containing organosulfur compound represented by the formula (I), wherein $R^1$ represents —C(=G)$R^5$, G represents an oxygen atom, $R^2$ represents a methyl group, and m is 0;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, $R^2$ represents a methyl group, and m is 0;

a fluorine-containing organosulfur compound represented by the formula (I), wherein $R^1$ represents —C(=G)$R^5$, G represents an oxygen atom, $R^5$ represents a methoxy group, $R^2$ represents a methyl group, and m is 0;

a fluorine-containing organosulfur compound represented by the formula (I), wherein $R^1$ represents —C(=G)$R^5$, G represents an oxygen atom, $R^5$ represents an amino group, $R^2$ represents a methyl group, and m is 0;

a fluorine-containing organosulfur compound represented by the formula (I), wherein le represents a cyano group, $R^2$ represents a methyl group, and m is 0;

a fluorine-containing organosulfur compound represented by the formula (I), wherein le represents a halogen atom, $R^2$ represents a hydrogen atom, and m is 0;

a fluorine-containing organosulfur compound represented by the formula (I), wherein each of R and $R^2$ independently represents a halogen atom, and m is 0;

a fluorine-containing organosulfur compound represented by the formula (I), wherein each of $R^1$ and $R^2$ represents a hydrogen atom, in is 1, and $R^3$ and $R^4$ represent a C1-C4 chain hydrocarbon group or a hydrogen atom;

a fluorine-containing organosulfur compound represented by the formula (I), wherein $R^1$ represents a C1-C4 chain hydrocarbon group optionally substituted with a halogen atom, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents a C1-C4 alkyl group optionally substituted with a halogen atom, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents a methyl group, $R^2$ represents a hydrogen atom, in is 1, and each of $R^3$ and $R^4$ independently represents a C1-C4 chain hydrocarbon group or a hydrogen atom;

a fluorine-containing organosulfur compound represented by the formula (I), wherein $R^1$ represents a C1-C4 chain hydrocarbon group optionally substituted with a halogen atom, $R^2$ represents a halogen atom, in is 1, and each of $R^3$ and $R^4$ independently represents a C1-C4 chain hydrocarbon group or a hydrogen atom;

a fluorine-containing organosulfur compound represented by the formula (I), wherein $R^1$ represents a C1-C4 alkyl group optionally substituted with a halogen atom, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^l$ represents a methyl group, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents a C1-C4 chain hydrocarbon group optionally substituted with a halogen atom, $R^2$ represents a methyl group, m is 1, and each of $R^3$ and $R^4$ independently represents a C1-C4 chain hydrocarbon group or a hydrogen atom;

a fluorine-containing organosulfur compound represented by the formula (I), wherein $R^1$ represents a C1-C4 alkyl group optionally substituted with a halogen atom, $R^2$ represents a methyl group, m is 1, and each of $R^3$ and $R^4$ independently represents a C1-C4 chain hydrocarbon group or a hydrogen atom;

a fluorine-containing organosulfur compound represented by the formula (I), wherein $R^1$ and $R^2$ represent methyl groups, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, G represents an oxygen atom, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, G represents an oxygen atom, $R^5$ represents a methoxy group, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, G represents an oxygen atom, $R^5$ represents an amino group, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents a cyano group, $R^2$ represents a hydrogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, $R^2$ represents a halogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, G represents an oxygen atom, $R^2$ represents a halogen atom, m is 1, and each of $R^3$ and $R^4$ independently represents a C1-C4 chain hydrocarbon group or hydrogen atom;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, $R^2$ represents a halogen atom, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, G represents an oxygen atom, $R^5$ represents a methoxy group, $R^2$ represents a halogen atom, m is 1, and each of $R^3$ and $R^4$ independently represents a C1-C4 chain hydrocarbon group or a hydrogen atom;

A fluorine-containing organosulfur compound represented by the formula (I), wherein $R^1$ L represents —C(=G)$R^5$, G represents an oxygen atom, $R^5$ represents an amino group, $R^2$ represents a halogen atom, in is 1, and each of $R^3$ and $R^4$ independently represents a C1-C4 chain hydrocarbon group or a hydrogen atom;

a fluorine-containing organosulfur compound represented by the formula (I), wherein $R^1$ L represents a cyano group, $R^2$ represents a halogen atom, in is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, $R^2$ represents a methyl group, in is 1, and each of $R^3$ and $R^4$ independently represents a C1-C4 chain hydrocarbon group or a hydrogen atom;

a fluorine-containing organosulfur compound represented by the formula (I), wherein $R^1$ L represents —C(=G)$R^5$, G represents an oxygen atom, $R^2$ represents a methyl group, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, G represents an oxygen atom, $R^5$ represents a C1-C4 alkoxy group optionally substituted with a halogen atom, $R^2$ represents a methyl group, in is 1, and each of $R^3$ and $R^4$ independently represents a C1-C4 chain hydrocarbon group or a hydrogen atom;

a fluorine-containing organosulfur compound represented by the formula (I), wherein $R^1$ L represents —C(=G)$R^5$, G represents an oxygen atom, $R^5$ represents a methoxy group, $R^2$ represents a methyl group, m is 1, and each of $R^3$ and $R^4$ independently represents a C1-C4 chain hydrocarbon group or a hydrogen atom;

a fluorine-containing organosulfur compound represented by the formula (I), wherein $R^1$ represents —C(=G)$R^5$, G represents an oxygen atom, $R^5$ represents an amino group, $R^2$ represents a methyl group, m is 1, and each of $R^3$ and $R^4$ independently represents a C1-C4 chain hydrocarbon group or a hydrogen atom;

a fluorine-containing organosulfur compound represented by the formula (I), wherein $R^1$ represents a cyano group, $R^2$ represents a methyl group, m is 1, and each of $R^3$ and $R^4$ independently represents a C1-C4 chain hydrocarbon group or a hydrogen atom;

a fluorine-containing organosulfur compound represented by the formula (I), wherein $R^1$ represents a halogen atom, $R^2$ represents a hydrogen atom, m is 1, and each of $R^3$ and $R^4$ independently represent a C1-C4 chain hydrocarbon group or a hydrogen atom;

a fluorine-containing organosulfur compound represented by the formula (I), wherein $R^1$ and $R^2$ represent halogen atoms, m is 1, and each of $R^3$ and $R^4$ independently represents a C1-C4 chain hydrocarbon group or a hydrogen atom;

a fluorine-containing organosulfur compound represented by the formula (I), wherein Q represents a fluorine atom;

a fluorine-containing organosulfur compound represented by the formula (I), wherein Q represents a C1-05 haloalkyl group containing at least one fluorine atom;

a fluorine-containing organosulfur compound represented by the formula (I), wherein Q represents a fluoromethyl group;

a fluorine-containing organosulfur compound represented by the formula (I), wherein Q represents a trifluoromethyl group;

a fluorine-containing organosulfur compound represented by the formula (I), wherein Q represents a 1,1,2,2,2-pentafluoroethyl group;

a fluorine-containing organosulfur compound represented by the formula (I), wherein Q represents a 1,1,2,2,3,3,3-heptafluoropropyl group;

a fluorine-containing organosulfur compound represented by the formula (I), wherein n is 0;

a fluorine-containing organosulfur compound represented by the formula (I), wherein n is 1; and a fluorine-containing organosulfur compound represented by the formula (I), wherein n is 2.

Hereinafter, the process for producing a present compound will be described.

Among the compounds of the present invention, the compound represented by the formula (I), wherein n is 0, i.e., the compound represented by the formula (I-a) can be prepared by the following Production Process 1 to Production Process 5.

Production Process 1

The compound represented by the formula (I-a) can be prepared, for example, by reacting the compound (a) with the compound (b):

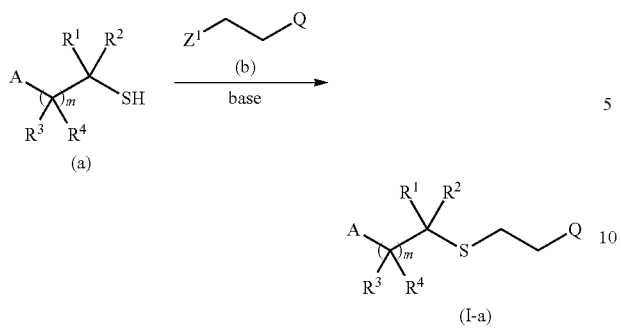

wherein A, Q, $R^1$, $R^2$, $R^3$, $R^4$ and m are as defined above; and $Z^1$ represents a leaving group such as a chlorine atom, a bromine atom, an iodine atom and a methanesulfonyl group.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydride, sodium hydroxide, potassium hydroxide and potassium carbonate; alkali metal alkoxides such as sodium methoxide and potassium tert-butoxide; and organic bases such as triethylamine, 1,4-diazabicyclo[2.2.2]octane and 1,8-diazabicyclo[5.4.0]-7-undecene. The amount of the base to be used for the reaction is usually from 1 to 10 mol per 1 mol of the compound (a).

The amount of the compound (b) to be used for the reaction is usually from 1 to 10 mol per 1 mol of the compound (a).

The reaction temperature is usually in the range from −50 to 100° C., and the reaction time is usually from 1 to 24 hours.

After the completion of the reaction, the compound (I-a) can be isolated by subjecting the reaction mixture to an operation, for example, by pouring the reaction mixture into water, extracting the resulting mixture with an organic solvent, and concentrating the organic layer. The isolated compound (I-a) can be further purified by subjecting it to chromatography, recrystallization or the like, if necessary.

Production Process 2

The compound represented by the formula (I-a) can also be prepared by reacting the compound (c) with the compound (d):

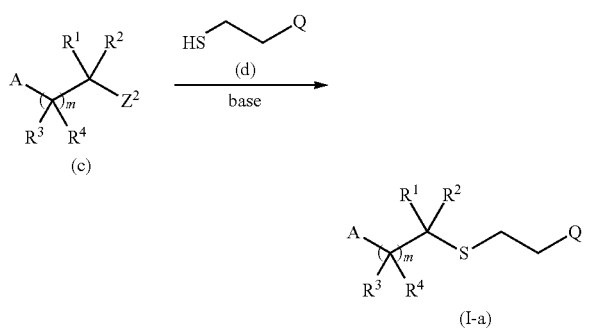

wherein A, Q, $R^1$, $R^2$, $R^3$, $R^4$ and m are as defined above; and $Z^2$ represents a leaving group such as a chlorine atom, a bromine atom, an iodine atom and a methanesulfonyl group.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydride, sodium hydroxide, potassium hydroxide and potassium carbonate; alkali metal alkoxides such as sodium methoxide and potassium tert-butoxide; and organic bases such as triethylamine, 1,4-diazabicyclo[2.2.2]octane and 1,8-diazabicyclo[5.4.0]-7-undecene. The amount of the base to be used for the reaction is usually from 1 to 10 mol per 1 mol of the compound (d).

The amount of the compound (c) to be used for the reaction is usually from 1 to 10 mol per 1 mol of the compound (d).

The reaction temperature is usually in the range from to 100° C., and the reaction time is usually from 1 to 24 hours.

After the completion of the reaction, the compound (I-a) can be isolated by subjecting the reaction mixture to an operation, for example, by pouring the reaction mixture into water, extracting the resulting mixture with an organic solvent, and concentrating the organic layer. The isolated compound (I-a) can be further purified by subjecting it to chromatography, recrystallization or the like, if necessary.

Production Process 3

The compound represented by the formula (I-a) can also be prepared from the compound (c) by the following method:

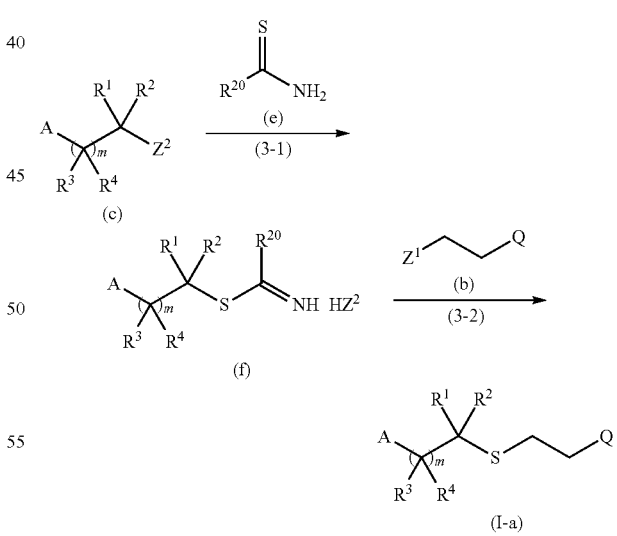

wherein A, Q, $R^1$, $R^2$, $R^3$, $R^4$, m, $Z^1$ and $Z^2$ are as defined above; and $R^{20}$ represents a methyl group or amino group.

Step (3-1)

The compound (f) can be prepared by reacting the compound (c) with the compound (e).

The reaction is usually carried out in the presence of a solvent.

Examples of the solvent to be used for the reaction include halogenated hydrocarbons such as dichloromethane and chloroform; alcohols such as methanol and ethanol; and a mixture thereof.

The amount of the compound (e) to be used for the reaction is usually from 1 to 3 mol per 1 mol of the compound (c).

The reaction temperature is usually in the range from 20 to 200° C., and the reaction time is usually from 0.5 to 24 hours.

After the completion of the reaction, the compound (f) can be isolated by subjecting the reaction mixture to an operation such as concentration. The isolated compound (f) can be served for the Step (3-2) as it is, or subjected to further purification such as recrystallization, if necessary.

Step (3-2)

The compound represented by the formula (I-a) can be prepared by reacting the compound (f) with the compound (b) in the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydroxide and potassium hydroxide; and alkali metal alkoxides such as sodium methoxide and potassium tert-butoxide.

The amount of the base to be used for the reaction is usually from 1 to 50 mol per 1 mol of the compound (f).

The amount of the compound (b) to be used for the reaction is usually from 1 to 10 mol per 1 mol of the compound (f).

This reaction can also be carried out using a phase transfer catalyst such as tetra-n-butylammonium bromide, if necessary. The amount of the phase transfer catalyst to be used for the reaction is usually from 0.05 to 1.0 mol per 1 mol of the compound (f).

The reaction temperature is usually in the range from −50 to 100° C., and the reaction time is usually from 1 to 24 hours.

After the completion of the reaction, the compound (I-a) can be isolated by subjecting the reaction mixture to an operation, for example, by pouring the reaction mixture into water, extracting the resulting mixture with an organic solvent and concentrating the organic layer. The isolated compound (I-a) can be further purified by subjecting it to chromatography, recrystallization or the like, if necessary.

Production Process 4

The compound represented by the formula (I-a) can also be prepared from a compound (c) by the following method:

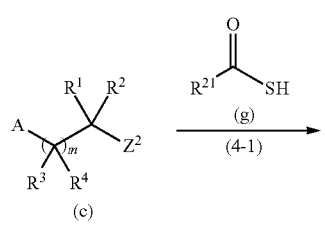

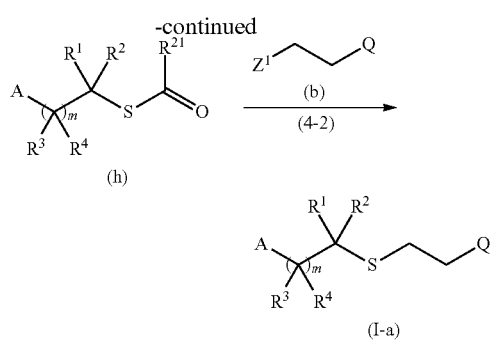

wherein A, Q, $R^1$, $R^2$, $R^3$, $R^4$, m, $Z^1$ and $Z^2$ are as defined above; and $R^{21}$ represents a methyl or phenyl group.

Step (4-1)

The compound (h) can be prepared by reacting the compound (c) with the compound (g) in the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; and a mixture thereof.

Examples of the base to be used for the reaction include inorganic bases such as sodium hydride and potassium carbonate; and organic bases such as triethylamine, 1,4-diazabicyclo[2.2.2]octane and 1,8-diazabicyclo[5.4.0]-7-undecene.

The amount of the base to be used for the reaction is usually from 1 to 10 mol per 1 mol of the compound (c).

The amount of the compound (g) to be used for the reaction is usually from 1 to 5 mol per 1 mol of the compound (c).

The reaction temperature is usually in the range from −20 to 80° C., and the reaction time is usually from 1 to 24 hours.

After the completion of the reaction, the compound (h) can be isolated by subjecting the reaction mixture to an operation, for example, by pouring the reaction mixture into acidic water (e.g., dilute hydrochloric acid), extracting the resulting mixture with an organic solvent and concentrating the organic layer. The isolated compound (h), can be further purified by subjecting it to chromatography, recrystallization or the like, if necessary.

Step (4-2)

The compound represented by the formula (I-a) can be prepared by reacting the compound (b) with the compound (h) in the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydroxide and potassium hydroxide; and alkali metal alkoxides such as sodium methoxide, sodium ethoxide and potassium tert-butoxide. The amount of the base used for the reaction is usually from 1 to 10 mol per 1 mol of the compound (h).

The amount of the compound (b) to be used for the reaction is usually from 1 to 10 mol per 1 mol of the compound (h).

The reaction temperature is usually in the range from −50 to 100° C., and the reaction time is usually from 1 to 24 hours.

After the completion of the reaction, the compound (I-a) can be isolated by subjecting the reaction mixture to an operation, for example, by pouring the reaction mixture into water, extracting the resulting mixture with an organic solvent and concentrating the organic layer. The isolated compound (I-a) can be further purified by subjecting it to chromatography, recrystallization or the like, if necessary.

Production Process 5

The compound represented by the formula (I-a) can also be prepared from the compound (b) by the following method:

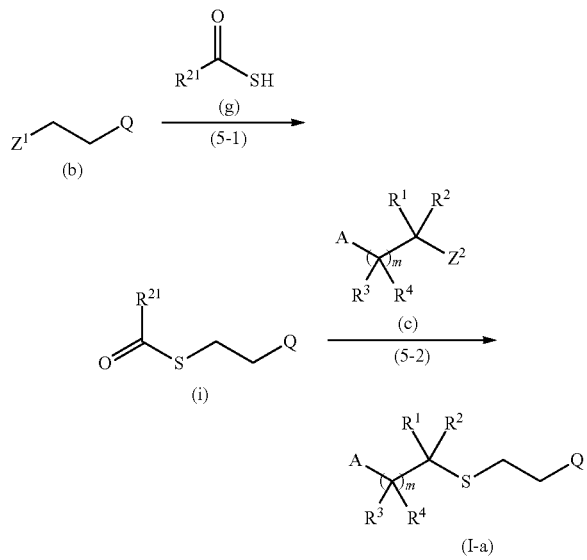

wherein A, Q, $R^1$, $R^2$, $R^3$, $R^4$, $R^{21}$, m, $Z^1$ and $Z^2$ are as defined above.

Step (5-1)

The compound (i) can be prepared by reacting the compound (b) with the compound (g) in the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; and a mixture thereof.

Examples of the base to be used for the reaction include inorganic bases such as sodium hydride and potassium carbonate; and organic bases such as triethylamine, 1,4-diazabicyclo[2.2.2]octane and 1,8-diazabicyclo[5.4.0]-7-undecene.

The amount of the base to be used for the reaction is usually from 1 to 10 mol per 1 mol of the compound (b).

The amount of the compound (g) used for the reaction is usually from 1 to 5 mol per 1 mol of the compound (b).

The reaction temperature is usually in the range from −20 to 80° C., and the reaction time is usually from 1 to 24 hours.

After the completion of the reaction, the compound (i) can be isolated by subjecting the reaction mixture to an operation, for example, by pouring the reaction mixture into acidic water (e.g., dilute hydrochloric acid), extracting the resulting mixture with an organic solvent and concentrating the organic layer. The isolated compound (i) can be further purified by subjecting it to chromatography, recrystallization or the like, if necessary.

Step (5-2)

The compound represented by the formula (I-a) can be prepared by reacting the compound (c) with the compound (i) in the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydroxide and potassium hydroxide; and alkali metal alkoxides such as sodium methoxide, sodium ethoxide and potassium tert-butoxide. The amount of the base to be used for the reaction is usually from 1 to 10 mol per 1 mol of the compound (i).

The amount of the compound (c) to be used for the reaction is usually from 1 to 10 mol per 1 mol of the compound (i).

The reaction temperature is usually in the range from −50 to 100° C., and the reaction time is usually from 1 to 24 hours.

After the completion of the reaction, the compound (I-a) can be isolated by subjecting the reaction mixture to an operation, for example, by pouring the reaction mixture into water, extracting the resulting mixture with an organic solvent and concentrating the organic layer. The isolated compound (I-a) can be further purified by subjecting it to chromatography, recrystallization or the like, if necessary.

Production Process 6

Among the compounds of the present invention, the compound represented by the formula (I), wherein $R^1$ represents —C(=O)$R^5$ or a cyano group and $R^2$ is a hydrogen atom, i.e., the compound represented by the formula (I-b), or the compound represented by the formula (I), wherein $R^1$ represents —C(=O)$R^5$ or a cyano group and $R^2$ represents a C1-C4 chain hydrocarbon group optionally substituted with a halogen atom, i.e., the compound represented by the formula (I-c) can be prepared from the compound (j) by the following method:

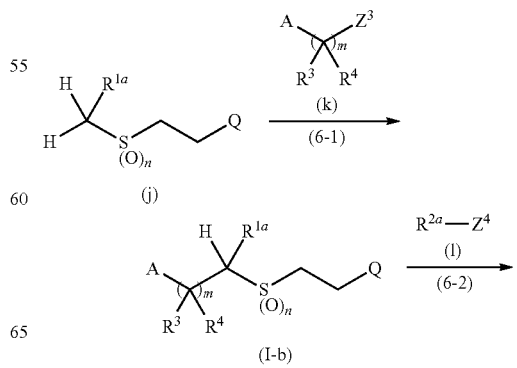

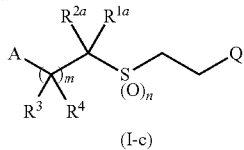

(I-c)

wherein A, Q, $R^3$, $R^4$, n and m are as defined above; $Z^3$ represents a leaving group such as a fluorine atom, a chlorine atom, a bromine atom, an iodine atom or a methanesulfonyl group; $Z^4$ represents a leaving group such as a chlorine atom, a bromine atom, an iodine atom or a methanesulfonyl group; $R^{1a}$ represents —C(=O)$R^5$ or a cyano group; and $R^{2a}$ represents a C1-C4 chain hydrocarbon group optionally substituted with a halogen atom.

Step (6-1)

The compound represented by the formula (I-b) can be prepared by reacting the compound (k) with the compound (j) in the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydride, sodium hydroxide, potassium hydroxide and potassium carbonate; alkali metal alkoxides such as sodium methoxide and potassium tert-butoxide; and organic bases such as triethylamine, 1,4-diazabicyclo[2.2.2]octane and 1,8-diazabicyclo[5.4.0]-7-undecene. The amount of the base to be used for the reaction is usually from 1 to 10 mol per 1 mol of the compound (j).

The amount of the compound (k) to be used for the reaction is usually from 1 to 10 mol per 1 mol of the compound (j).

In the case where m is 0 in the compound (j), the reaction can be carried out in the presence of a metal catalyst such as a palladium complex including tetrakis(triphenylphosphine) palladium (0) and tris(dibenzylideneacetone) dipalladium (0) chloroform complex; and a copper (I) halide salt such as copper (I) bromide and copper (I) iodide. The amount of the metal catalyst to be used is usually from 0.001 to 0.5 mol per 1 mol of the compound (j).

The reaction temperature is usually in the range from −50 to 100° C., and the reaction time is usually from 1 to 24 hours.

After the completion of the reaction, the compound (1-b) can be isolated by subjecting the reaction mixture to an operation, for example, by pouring the reaction mixture into water, extracting the resulting mixture with an organic solvent and concentrating the organic layer. The isolated compound (I-b) can be further purified by subjecting it to chromatography, recrystallization or the like, if necessary.

Step (6-2)

The compound represented by the formula (I-c) is prepared by reacting the compound (l) with the compound (I-b) in, the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydride, sodium hydroxide, potassium hydroxide and potassium carbonate; alkali metal alkoxides such as sodium methoxide and potassium tert-butoxide; and organic bases such as triethylamine, 1,4-diazabicyclo[2.2.2]octane and 1,8-diazabicyclo[5.4.0]-7-undecene. The amount of the base to be used for the reaction is usually from 1 to 10 mol per 1 mol of the compound (I-b).

The amount of the compound (1) to be used for the reaction is usually from 1 to 10 mol per 1 mol of the compound (I-b).

The reaction temperature is usually in the range from −50 to 100° C., and the reaction time is usually from 1 to 24 hours.

After the completion of the reaction, the compound (I-c) can be isolated by subjecting the reaction mixture to an operation, for example, pouring the reaction mixture into water, extracting the resulting mixture with an organic solvent and concentrating the organic layer. The isolated compound (I-c) can be further purified by subjecting it to chromatography, recrystallization or the like, if necessary.

Production Process 7

Among the compounds of the present invention, the compound represented by the formula (I),wherein $R^1$ represents —C(=O)$R^5$ or a cyano group and $R^2$ represents a C1-C4 chain hydrocarbon group optionally substituted with a halogen atom, i.e., the compound represented by the formula (I-c) can be prepared from a compound (j) by the following method:

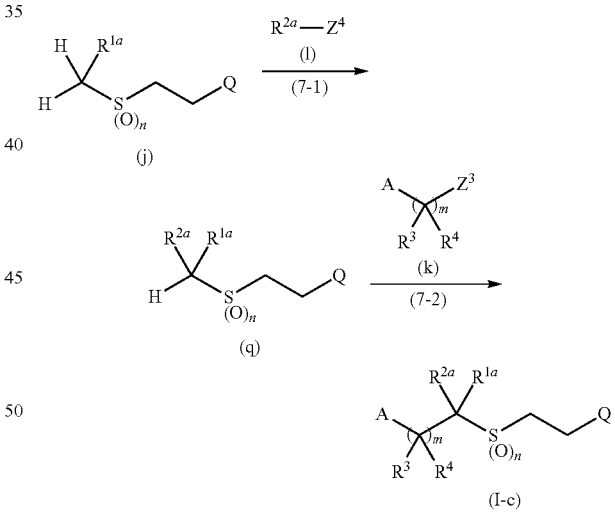

wherein A, Q, $R^{1a}$, $R^{2a}$, $R^3$, $R^4$, n, m, $Z^3$ and $Z^4$ are as defined above.

Step (7-1)

The compound (q) can be prepared by reacting the compound (1) with the compound (j) in the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydride, sodium hydroxide, potassium hydroxide and potassium carbonate; alkali metal alkoxides such as sodium methoxide and potassium tert-butoxide; and organic bases such as triethylamine, 1,4-diazabicyclo[2.2.2]octane and 1,8-diazabicyclo[5.4.0]-7-undecene. The amount of the base to be used for the reaction is usually from 1 to 10 mol per 1 mol of the compound (j).

The amount of the compound (1) to be used for the reaction is usually from 1 to 10 mol per 1 mol of the compound (j).

The reaction temperature is usually in the range from −50 to 100° C., and the reaction time is usually from 1 to 24 hours.

After the completion of the reaction, the compound (q) can be isolated by subjecting the reaction mixture to an operation, for example, by pouring the reaction mixture into water, extracting the resulting mixture with an organic solvent and concentrating the organic layer. The isolated compound (q) can be further purified by subjecting it to chromatography, recrystallization or the like, if necessary.

Step (7-2)

The compound represented by the formula (I-c) can be prepared by reacting the compound (k) with the compound (q) in the presence of a base.

The reaction is usually carried out in a solvent in the presence of a base.

Examples of the solvent to be used for the reaction include ethers such as diethylether, tetrahydrofuran and dimethoxyethane; acid amides such as N,N-dimethylformamide; organosulfurs such as dimethyl sulfoxide and sulfolane; aliphatic hydrocarbons such as hexane and heptane; aromatic hydrocarbons such as toluene and xylene; halogenated hydrocarbons such as 1,2-dichloroethane and chlorobenzene; water; and a mixture thereof.

Examples of the base to be used for the reaction include inorganic bases such as sodium hydride, sodium hydroxide, potassium hydroxide and potassium carbonate; alkali metal alkoxides such as sodium methoxide and potassium tert-butoxide; and organic bases such as triethylamine, 1,4-diazabicyclo[2.2.2]octane and 1,8-diazabicyclo[5.4.0]-7-undecene. The amount of the base to be used for the reaction is usually from 1 to 10 mol per 1 mol of the compound (q).

The amount of the compound (k) to be used for the reaction is usually from 1 to 10 mol per 1 mol of the compound (q).

In the case where m is 0 in the compound (q), the reaction can be carried out in the presence of a metal catalyst, such as a palladium complex including tetrakis(triphenylphosphine)palladium (0) and tris(dibenzylideneacetone) dipalladium (0) chloroform complex; and a copper (I) halide salt such as copper (I) bromide and copper (I) iodide. The amount of the metal catalyst to be used is usually from 0.001 to 0.5 mol per 1 mol of the compound (q).

The reaction temperature is usually in the range from −50 to 100° C., and the reaction time is usually from 1 to 24 hours.

After the completion of the reaction, the compound (I-c) can be isolated by subjecting the reaction mixture to an operation, for example, by pouring the reaction mixture into water, extracting the resulting mixture with an organic solvent and concentrating the organic layer. The isolated compound (I-c) can be further purified by subjecting it to chromatography, recrystallization or the like, if necessary.

Production Process 8

Among the compounds of the present invention, the compound represented by the formula (I), wherein $R^1$ represents —C(=O)$R^5$ or a cyano group and $R^2$ represents a halogen atom, i.e., the compound represented by the formula (I-d) can be prepared by reacting the compound (I-b) with a halogenating agent A:

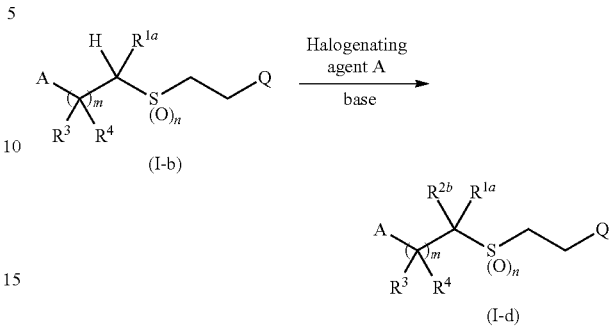

wherein A, Q, $R^{1a}$, $R^3$, $R^4$, n and m are as defined above; and $R^{2b}$ represents a halogen atom.

The reaction is usually carried out in the presence of a solvent.

Examples of the solvent to be used for the reaction include acid amides such as N,N-dimethylformamide; ethers such as diethylether and tetrahydrofuran; organosulfurs such as dimethyl sulfoxide and sulfolane; halogenated hydrocarbons such as chloroform, carbon tetrachloride, 1,2-dichloroethane, dichloromethane and dichlorobenzene; aliphatic nitriles such as acetonitrile and propionitrile; aromatic hydrocarbons such as toluene and xylene; water; and a mixture thereof.

Examples of the base to be used for the reaction include inorganic bases such as sodium hydride, sodium hydroxide, potassium hydroxide and potassium carbonate; alkali metal alkoxides such as sodium methoxide and potassium tert-butoxide; alkali metal amides such as lithium diisopropylamide; and organic bases such as triethylamine, 1,4-diazabicyclo [2.2.2]octane and 1,8-diazabicyclo[5.4.0]-7-undecene. The amount of the base to be used for the reaction is usually from 1 to 10 mol per 1 mol of the compound (I-b).

Examples of the halogenating agent A to be used for the reaction include halogenated hydrocarbons such as carbon tetrachloride and hexachloroethane; halogens such as fluorine, chlorine, bromine and iodine; N-halogenated succineimides such as N-chlorosuccinic acid imide, N-bromosuccinic acid imide and N-iodosuccinic acid imide; N-fluoropyridinium salts such as 1-fluoro-2,4,6-trimethylpyridinium, trifluoromethane sulfonate and 1,1'-difluoro-2,2'-bipyridinium bistetrafluoroborate; and inorganic salts such as copper (II) chloride and copper (II) bromide. The amount of the halogenating agent A to be used for the reaction is usually from 1 to 10 mol per 1 mol of the compound (I-b).

The reaction temperature is usually in the range from −100 to 100° C., and the reaction time is usually from 1 to 24 hours.

After the completion of the reaction, the compound (1-d) can be isolated by subjecting the reaction mixture to an operation, for example, pouring the reaction mixture into water, extracting the resulting mixture with an organic solvent and concentrating the organic layer. The isolated compound (1-d) can be further purified by subjecting it to chromatography, recrystallization or the like, if necessary.

Production Process 9

Among the compounds of the present invention, the compound represented by the formula (I-d) can be prepared by reacting the compound (I-b) with a halogenating agent B:

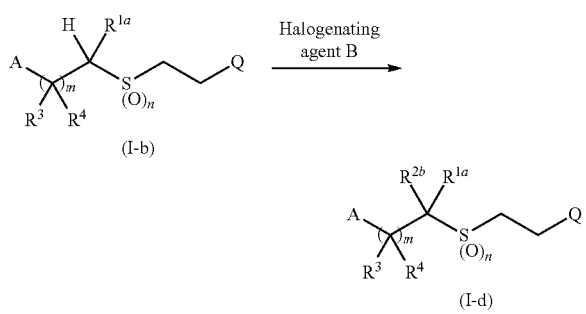

wherein A, Q, $R^{1a}$, $R^{2b}$, $R^3$, $R^4$, n and m are as defined above.

The reaction is usually carried out in the presence of a solvent.

Examples of the solvent to be used for the reaction include halogenated hydrocarbons such as chloroform, carbon tetrachloride, 1,2-dichloroethane, dichloromethane and dichlorobenzene; aliphatic nitriles such as acetonitrile and propionitrile; aromatic hydrocarbons such as toluene and xylene; aliphatic carboxylic acids such as acetic acid; and carbon disulfide; water; and a mixture thereof.

Examples of the halogenating agent B to be used for the reaction include halogens such as fluorine, chlorine, bromine and iodine; hydrogen halides such as hydrogen fluoride, hydrogen chloride, hydrogen bromide and hydrogen iodide; halogenated sulfur compounds such as thionyl chloride, thionyl bromide and sulfuryl chloride; and halogenated phosphorus compounds such as phosphorus trichloride, phosphorus tribromide, phosphorus pentachloride and phosphorus oxychloride. The amount of the halogenating agent B to be used for the reaction is usually from 1 to 10 mol per 1 mol of the compound (I-b).

The reaction temperature is usually in the range from −100 to 200° C., and the reaction time is usually from 1 to 24 hours.

After the completion of the reaction, the compound (I-d) can be isolated by subjecting the reaction mixture to an operation, for example, by pouring the reaction mixture into water, extracting the resulting mixture with an organic solvent and concentrating the organic layer. The isolated compound (I-d) can be further purified by subjecting it to chromatography, recrystallization or the like, if necessary.

Production Process 10

Among the compounds of the present invention, the compound represented by the formula (I), wherein n is 1 or 2, i.e. the compound represented by the formula (I-e) is prepared by reacting the compound (I-a) with an oxidizing agent A.

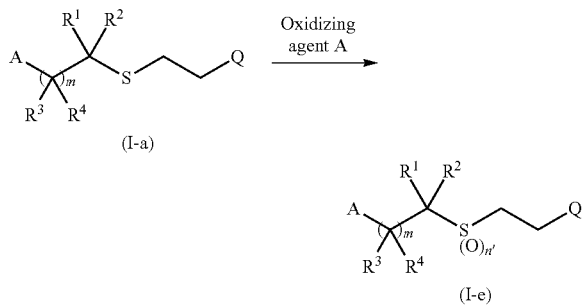

wherein A, Q, $R^1$, $R^2$, $R^3$, $R^4$ and m are as defined above; and n' represents 1 or 2.

The reaction is usually carried out in the presence of a solvent.

Examples of the solvent to be used for the reaction include alcohols such as methanol and ethanol; halogenated hydrocarbons such as dichloromethane and chloroform; aromatic hydrocarbons such as toluene and xylene; aliphatic carboxylic acids such as acetic acid and trifluoroacetic acid; water; and a mixture thereof.

Examples of the oxidizing agent A to be used for the reaction include organic peroxides such as peracetic acid, trifluoroperacetic acid and m-chloroperbenzoic acid; halogen molecules such as chlorine and bromine; halogen-containing imides such as N-chlorosuccinic acid imide; halides such as perchloric acid (or the salt) and periodic acid (or the salt); permanganates such as potassium permanganate; chromates such as potassium chromate; peroxysulfates such as potassium peroxysulfate; and hydrogen peroxide. The amount of the oxidizing agent to be used for the reaction is usually from 1 to 10 mol per 1 mol of the compound (I-a).

The reaction temperature is usually in the range from −50 to 200° C., and the reaction time is usually from 1 to 72 hours.

After the completion of the reaction, the compound (I-e) can be isolated by subjecting the reaction mixture to an operation, for example, by pouring the reaction mixture into water, extracting the resulting mixture with an organic solvent and concentrating the organic layer. The compound can be further purified by subjecting it to chromatography, recrystallization or the like, if necessary.

The compound (a), the compound (b), the compound (d), the compound (e), the compound (g), the compound (j), the compound (k) and the compound (l) are known compounds, or can be prepared by known production processes.

The compound (c) is a known compound, or can be prepared according to a known production process.

Examples of the pests against which the present compound exhibits a controlling effect include harmful insects and ticks. Specific examples thereof are as follows.

Hemiptera:

Planthoppers (Delphacidae) such as small brown planthopper (*Laodelphax Striatellus*), brown rice planthopper (*Nilaparvata lugens*), and white-backed rice planthopper (*Sogatella furcifera*); leafhoppers (Deltocephalidae) such as green rice leafhopper (*Nephotettix Cincticeps*), green rice leafhopper (*Nephotettix virescens*), and tea green leafhopper (*Empoasca Onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavatus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as Calfornia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchase*), Japanese mealybug (*Planococcus kraunhiae*), Cosmstock mealybug (*Psendococcils longispinus*), and white peach scale (*Pseudaulacaspis pentagona*); lace bugs (Tingidae); cimices such as *Cimex lectularius*; psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogate*), Indian meal moth (*Plodia interpunctella*), Ostrinia furnacalis, cabbage webworm (*Hellula undalis*), and bluegrass webworm (*Pediasia teterrellus*); owlet moths (*Noctuidae*) such as common cutworm (*Spodoptera litura*), beet annyworm (*Spodoptera exigua*), armyworm (*Pseudaletia separate*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; white butterflies (*Pieridae*) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoniella*); Carposinidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback moths (*Plutella xylostella*); gelechiid moths (Gelechiidae) such as pink bollworm (*Pectinophora gossypiella*), and potato tubewonn (*Phthorimaea operculella*); tiger moths and allies (Arctiidae) such as fall webwon̄n (*Hyphantria cunea*); tineid moths (Tineidae) such as casemaking clothes moth (*Tinea translucens*), and webbing clothes moth (*Tineola bisselliella*), etc.;

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.;

Diptera:

Culices (Calicidae) such as common mosquito (*Culex pipiens pallens*), *Culex tritaeniorhynchus*, and Southern house mosquito (*Culex quinquefasciatus*); *Aedes* spp. such as yellow fever mosquito (*Aedes aegypti*), and Asian tiger mosquito (*Aedes albopictus*); *Anopheles* spp. such as *Anopheles sinensis*; Chironomidae; Houseflies (Muscidae) such as housefly (*Musca domestica*), and false stable fly (*Muscina stabulans*); blow flies (Calliphoridae); flesh flies (Sarcophagidae); little house flies (Fanniidae); anthomyiid flies (Anthomyiidae) such as seedcorn maggot (*Delia platura*), and onion maggot (*Delia antique*); leafininer flies (Agromyzidae) such as rice leafininer (*Agromyza oryzae*), rice leafmincr (*Hydrellia griseola*), tomato leafininer (*Liriomyza sativae*), legume leafininer (*Liriomyza trifolia*), and garden pea leafininer (*Chromatomyia horticola*); gout flies (Chloropidae) such as rice stein maggot (*Chlorops oryzae*); fruit flies (Tephritidae) such as melon fly (*Dacus Cucurbitae*), and Mediterranean fruit fly (*Ceratitis capitata*); drosophila flies (Drosophilidae); humpbacked flies (Phoridae) such as *Megaselia spiracularis*; Psychodidae such as *Clogmia albipunctata*; Simuliidae; Tabanidae such as horsefly (*Tabanus trigonus*); stable flies (*Stomoxys calcitrans*), etc.;

Coleoptera:

Corn root worms (*Diabrotica* spp.) such as Western corn rootworm (*Diabrotica virgifera virgifera*), and Southern corn root worm (*Diabrotica undecimpunctata* howardi); scarabs (Scarabaeidae) such as cupreous chafer (*Anomala cuprea*), soybean beetle (*Anomala rufocuprea*), and Japanese beetle (*Popillia japonica*); weevils (Curculionidae) such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting bilibug (*Sphenophorus venatus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado beetle (*Leptinotarsa decemlineata*); dermestid beetles (Dermestidae) such as varied carpet beetle (*Anthrenus verbasci*), and hide beetle (*Dermestes maculates*); deathwatch beetles (Anobiidae) such as cigarette beetle (*Lasioderma serricorne*); *Epilachna* such as twenty-eight-spotted ladybird (*Epilachna vigintioctopunctata*); bark beetles (Scolytidae) such as powder post beetle (*Lyctus brunneus*), and pine shoot beetle (*Tomicus piniperda*); false powderpost beetles (Bostrichidae); spider beetles (Ptinidae); longhorn beetles (Cerambycidae) such as white-spotted longicorn beetle (*Anoplophora malasiaca*); click beetles (*Agriotes* spp.); *Paederus fuscipes*, etc.;

Orthoptera:

Asiatic locust (*Locusta migratoria*), African mole cricket (*Gryllotalpa africana*), rice grasshopper (*Oxya yezoensis*), rice grasshopper (*Oxya japonica*), Grylloidea, etc.;

Siphonaptera:

Cat flea (*Ctenocephalides felis*), dog flea (*Ctenocephalides canis*), human flea (*Pulex irritans*), oriental rat flea (*Xenopsylla cheopis*), etc.;

Anoplura:

Human body louse (*Pediculus humanus corporis*), crab louse (*Phthirus pubis*), short-nosed cattle louse (*Haematopinus eurysternus*), sheep louse (*Damalinia ovis*), hog louse (*Haematopinus suis*), etc.;

Hymenoptera:

Ants (Formicidae) such as *Monomorium pharaonis*, *Formica fusca japonica*, black house ant (*Ochetellus glaber*), *Pristomyrmex pungens*, *Pheidole noda*, leaf-cutting ant (*Acromyrmex* spp.), and fire ant (*Solenopsis* spp.); hornets (Vespidae); bethylid wasps (Bethylidae); sawflies (Tenthredinidae) such as Cabbage sawfly (*Athalia rosae*), and *Athalia japonica*, etc.;

Blattodea:

Cockroaches (Blattariae) such as German cockroach (*Blattella gennanica*), smokybrown cockroach (*Periplaneta fuliginosa*), American cockroach (*Periplaneta americana*), *Periplaneta brunnea*, and oriental cockroach (*Blatta orientalis*);

Isoptera:

Termites (Tennitidae) such as subterranean termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus*, *Neotermes koshunensis*, *Glyptotermes satsumensis*, *Glyptotermes nakajimai*, *Glyptotennes fuscus*, *Glyptotermes kodamai*, *Glyptotermes kushimensis*, Japanese dampwood termite (*Hodotermopsis japonica*), *Coptotennes guangzhoensis*, *Reticulitennes miyatakei*, *Reticulitennes flavipes amamianus*, *Reticulitennes kanmonensis* (*Reticulitennes* sp.), *Nasutitennes takasagoensis*, *Pericapritermes nitobei*, *Sinocapritermes inushae*, etc.;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phenicis*; Tuckerellidae; ticks (Ixodidae) such as *Haemaphysalis longicornis*, American dog tick (*Dermacentor variabilis*), *Haemaphysalis flava, Dermacentor taiwanicus*, American dog tick (*Dermacentor variabilis*), *Ixodes ovatus, Ixodes persulcatus*, black legged tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as *Sarcoptes scabiei*; follicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus, Cheyletus malaccensis*, and *Cheyletus moorei*; parasitoid mites (Dennanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.;

Chilopoda: *Thereuonema hilgendorfi, Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginatus, Limax flavus*, etc.

The pesticidal composition formulation of the present invention can be the present compound as it is. However, it is usually formulated into a form of emulsifiable concentrate, oil solution, shampoo, flowable formulation, dust, wettable powder, granule, paste, microcapsule formulation, foam, aerosol, carbon dioxide formulation, tablet or resin formulation by mixing the present compound with a solid, liquid or gaseous carrier, and adding a surfactant or other auxiliary agents for formulations if necessary. These formulations are sometimes used after processed into poison bait, mosquito coil, electric mosquito mat, smoking pesticide, fumigant or sheet.

These formulations usually contain 0.1 to 95% by weight of the present compound.

Examples of the solid carrier used for the formulation include clays (e.g., kaolin clay, diatomaceous earth, bentonite, Fubasami clay and acidic white clay), synthetic hydrated silicon oxide, talc, ceramics, other inorganic minerals (e.g., sericite, quarts, sulfur, active carbon, calcium carbonate and hydrated silica), and chemical fertilizers (e.g., ammonium sulfate, ammonium phosphate, ammonium nitrate, ammonium chloride and urea) in the form of fine powder or granule.

Examples of the liquid carrier include aromatic or aliphatic hydrocarbons (e.g., xylene, toluene, alkyl naphthalene, phenylxylylethane, kerosene, light oil, hexane and cyclohexane), halogenated hydrocarbons (e.g., chlorobenzene, dichloromethane, dichloroethane and trichloroethane), alcohols (e.g., methanol, ethanol, isopropyl alcohol, butanol, hexanol and ethylene glycol), ethers (e.g., diethylether, ethylene glycol dimethyl ether, diethylene glycol monomethyl ether, diethylene glycol monoethyl ether, propylene glycol monomethyl ether, tetrahydrofuran and dioxane), esters (e.g., ethyl acetate and butyl acetate), ketones (e.g., acetone, methyl ethyl ketone, methyl isobutyl ketone and cyclohexanone), nitriles (e.g., acetonitrile and isobutyronitrile), sulfoxides (e.g., dimethyl sulfoxide), acid amides (e.g., N,N-dimethylformamide and N,N-dimethylacetoamide), vegetable oils (e.g., soybean oil and cotton oil), vegetable essential oil (e.g., orange oil, hyssop oil and lemon oil) and water.

Examples of the gaseous carrier include butane gas, chlorofluorocarbon gas, liquefied petroleum gas (LPG), dimethyl ether and carbon dioxide.

Examples of the surfactant include alkyl sulfate ester salts, alkyl sulfonate, alkylaryl sulfonate, alkylaryl ethers, polyoxyethylenated alkylaryl ethers, polyethylene glycol ethers, polyhydric alcohol esters and sugar alcohol derivatives.

Examples of other auxiliary agents for formulations include binder, dispersant and stabilizer. Specific examples thereof include casein, gelatin, polysaccharides (e.g., starch, arabic gum, cellulose derivatives and arginic acid), lignin derivatives, bentonite, saccharides, synthetic water-soluble polymers (e.g., polyvinyl alcohol, polyvinyl pyrrolidone and polyacrylic acids), PAP (acidic isopropyl phosphate), BHT (2,6-di-t-butyl-4-methylphenol), BHA (mixture of 2-t-butyl-4-methoxyphenol and 3-t-butyl-4-methoxyphenol), plant oils, mineral oils, fatty acid and fatty acid ester.

Examples of a base material for the resin formulation include vinyl chloride-based polymers and polyurethane. The base material can be added with a plasticizer such as phthalic acid esters (e.g., dimethyl phthalate and dioctyl phthalate), adipic acid esters and stearic acid, if necessary. The resin formulation is prepared by kneading the compound of the present invention into the base material using a conventional kneading device, followed by molding it by injection molding, extrusion molding or press molding. The formulation can undergo further processes such as molding and cutting, if necessary, to be processed into a form of plate, film, tape, net or string. These resin formulations can be processed into collars for animals, ear tags for animals, sheet formulations, trap strings and horticultural supports.

Examples of a base material for poison bait include grain powder, plant oil, sucrose and crystalline cellulose, optionally added with an antioxidant such as dibutylhydroxy toluene and nordihydroguaiaretic acid, a preservative such as dehydroacetic acid, an accidental ingestion prevention agent by children and pets such as chili pepper, and a pest attractive fragrance such as peanut oil, cheese or onion flavor, as needed.

The pesticidal composition of the present invention is used by means of directly applying it to pests and/or applying it to habitats of pests (e.g., plant, animal and soil).

The pesticidal composition of the present invention can be used in crop lands such as cultivated lands, paddy fields, lawns and orchards. The pesticidal composition of the present invention can control harmful arthropods in a crop land without causing drug damage to crop plants cultivated in the crop land.

Examples of such crop plants include

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers and ornamental plants;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazE1 nut, almond, pistachio, cashew nut, macadamia nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The aforementioned crop plants include those having herbicide resistance imparted by a classical breeding method, a genetic engineering technique or the like. Examples of the herbicide to be resisted include as an HPPD inhibitor such as isoxaflutole, an ALS inhibitor such as imazethapyr or thifensulfuron-methyl; an EPSP synthesizing enzyme inhibitor; a glutamine synthesizing enzyme inhibitor; an acetyl CoA carboxylase inhibitor such as a trioxime or aryloxyphenoxypropionic acid herbicide; or bromoxynil.

Examples of the crop plant having herbicide resistance imparted by a classical breeding method include Clearfield (registered trademark) canola resistant to an imidazolinone herbicide such as imazethapyr, STS soybean resistant to a sulfonylurea ALS inhibitor herbicide such as thifensulfuron-methyl, and the like. Examples of the crop plant having resistance to an acetyl CoA carboxylase inhibitor include SR corn and the like. For example, crop plants having resistance to an acetyl CoA carboxylase inhibitor include SR corn and the like are found in Proc. Natl. Acad. Sci. USA 1990, 87, p. 7175-7179. In addition, a mutant acetyl CoA carboxylase resistant to an acetyl CoA carboxylase inhibitor is known, for example, in Weed Science 53: p. 728-746, 2005. When a gene encoding the mutant acetyl CoA carboxylase is introduced into a crop plant by a genetic engineering technique or when a mutation related to impartation of resistance is introduced into a gene encoding acetyl CoA carboxylase of a crop plant, a crop plant having the resistance to an acetyl CoA carboxylase inhibitor can be produced. Further, nucleic acids for introduction of a base substitution mutation can be introduced into the cell of a crop plant by chimeraplasty (see, Gura T. 1999, Repairing the Genome's Spelling Mistakes, Science 285: 316-318) to induce a site-directed amino acid mutation in the gene which is targeted by an acetyl CoA carboxylase inhibitor or herbicide of the crop plant, and thereby a crop plant resistant to an acetyl CoA carboxylase inhibitor or herbicide can be produced.

Examples of the crop plant having herbicide resistance imparted by a genetic engineering technique include corn cultivars having resistance to glyphosate or glufosinate. Some of such corn cultivars are sold under the trade name of RoundupReady (registered trademark), LibertyLink (registered trademark), and the like.

The aforementioned crop plants include those having an ability to produce an insecticidal toxin, for example a selective toxin, for example, a selective toxin originated from Bacillus which ability has been imparted by a genetic engineering technique.

Examples of the insecticidal toxin which is produced by such a genetically engineered plant include insecticidal proteins derived from Bacillus cereus and Bacillus popilliae; δ-endotoxins derived from Bacillus thuringiensis, such as Cry1Ab, Cry1Ac, Cry1F, Cry1Fa2, Cry2Ab, Cry3A, Cry3Bb1 and Cry9C; insecticidal proteins derived from Bacillus thuringiensis, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channE1 inhibitors such as sodium channel inhibitors and calcium channE1 inhibitors; juvenile hormone esterase; diuretic hormone receptors; stilbene synthase; bibenzyl syntase; chitinase; and glucanase.

The insecticidal toxin produced by such a genetically engineered plant also includes hybrid toxins of different insecticidal proteins, for example, δ-endotoxins such as Cry1Ab, Cry1Ac, Cry1F, Cry1Fa2, Cry2Ab, Cry3A, Cry3Bb1 and Cry9C and insecticidal proteins such as VIP 1, VIP 2, VIP 3 and VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-0 374 753, WO 93/07278, WO 95/34656, EP-A-0 427 529, EP-A-451878, WO 03/052073, and the like.

The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Heculex I (registered trademark) (a corn cultivar expressing Cry1Fa2 toxin and phosphinothricin N-acetyltransferase (PAT) for imparting resistance to gluphosinate), NuCOTN33B (registered trademark) (a cotton cultivar expressing Cry1Ac toxin), Bollgard I (registered trademark) (a cotton cultivar expressing Cry1Ac toxin), Bollgard II (registered trademark) (a cotton cultivar expressing Cry1Ac and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (registered trademark) (GA21 glyphosate-resistance character), Agrisure CB Advantage (registered trademark) (Bt11 corn borer (CB) character), Protecta (registered trademark), and the like.

The aforementioned crop plants include those to which ability to produce an anti-pathogen substance has been imparted by a genetic engineering technique.

Examples of the anti-pathogen substance includes PR proteins (PRPs described in EP-A-0 392 225); ion channel inhibitors such as sodium channE1 inhibitors, and calcium channE1 inhibitors (e.g. KP1, KP4, KP6 toxins etc. produced by viruses); stilbene synthase; bibenzyl synthase; chitinase; glucanase; substances produced by microorganisms such as peptide antibiotics, heterocycle-containing antibiotics, and protein factors involved in plant disease-resistance described in WO 03/000906; and the like. Such anti-pathogen substances and genetically engineered plants which produce the anti-pathogen substances are described in EP-A-0 392 225, WO 05/33818, EP-A-0 353 191, and the like.

When the pesticidal composition of the present invention is used for prevention of agricultural pest, the application rate is usually from 1 to 10,000 g/ha, preferably from 10 to 500 g/ha, in terms of the amount of an active ingredient. The emulsifiable concentrate, wettable powder, flowable formulation and microcapsule formulation are generally diluted with water to the concentration of the active ingredient amounts to 1 to 1000 ppm before use, and the dust and granule formulations are usually used as such. These formulations can be sprayed directly to the plants that should be protected from pests. Soil can also be treated with these formulations so as to prevent and eliminate pests inhabiting in the soil. Alternatively, these formulations can apply to a preplanting nursery bed or to a planting hole or strain root upon planting. Further, the pesticidal composition of the present invention can be applied in a sheet form, in such methods as wrapping it around a plant, placing it in the vicinity of a plant, or spreading it over a soil surface near a strain root.

In utilizing the pesticidal composition of the present invention for communicable disease control, the application rate is usually from 0.001 to 10 mg/m$^3$ in terms of the amount of the compound of the present invention when applied to space, while it is from 0.001 to 100 mg/m$^2$ when applied to plane. The emulsifiable concentrate, wettable powder, flowable formulation and the like are usually diluted with water before use so that the concentration of the compound of the present invention as the active ingredient becomes 0.01 to 10,000 ppm, while the oil solution, aerosol, smoking pesticide and poison bait are usually used as they are.

When the pesticidal composition of the present invention is used to livestock such as cows, horses, pigs, sheep, goats and chickens, and small animals such as dogs, cats, rats and mice, for the purpose of controlling external parasites, veterinary known methods are applied to the animals. Specifically, the formulation is administered by way of tablet, mixing in feed, suppository and injection (including intramuscular, subcutaneous, intravenous and intraperitoneal injections), when systemic control is intended. On the other hand, it is used by way of spraying the oil solution or aqueous solution, pour-on or spot-on treatment, washing an animal with a shampoo formulation, or putting a collar or ear tag made of the resin formulation to an animal, when non-systemic control is intended. The dosage of the compound of the present invention is usually in the range from 0.1 to 1000 mg per 1 kg of an animal body.

The pesticidal composition of the present invention can be used in combination with other insecticides, nematocides, acaricides, fungicides, herbicides, plant growth regulating substances, synergists, fertilizers, soil conditioners, animal feeds, and the like.

Examples of an active ingredient of such insecticide include (1) Organic Phosphorus Compounds:

acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) Carbamate Compounds:

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) Synthetic Pyrethroid Compounds:

acrinathrin, allethrin, beta-cyfluthrin, bifenthrin, cyclopropthrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, and the like;

(4) Nereistoxin Compounds:

cartap, bensultap, thiocyclam, monosultap, bisultap, and the like;

(5) Neonicotinoid Compounds:

imidacloprid, nitenpyram, acetamiprid, thiamethoxam, thiacloprid, dinotefuran, clothianidin, and the like;

(6) Benzoylurea Compounds:

chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole Compounds:

acetoprole, ethiprole, fipronil, vaniliprole, pyriprole, pyrafluprole, and the like;

(8) Bt Toxin Insecticides:

live spores or crystal toxins originated from *Bacillus* thuringiesis and a mixture thereof;

(9) Hydrazine Compounds:

chromafenozide, halofenozide, methoxyfenozide, tebufenozide, and the like;

(10) Organic Chlorine Compounds:
aldrin, dieldrin, dienochlor, endosulfan, methoxychlor, and the like;
(11) Natural Insecticides:
machine oil, nicotine sulfate, and the like;
(12) Other Insecticides:
avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metham-ammonium, metham-sodium, methyl bromide, potassium oleate, protrifenbute, spiromesifen, sulfur, metaflumizone, spirotetramat, pyrifluquinazone, spinetoram, chlorantraniliprole, tralopyril, a compound represented by the following formula (A):

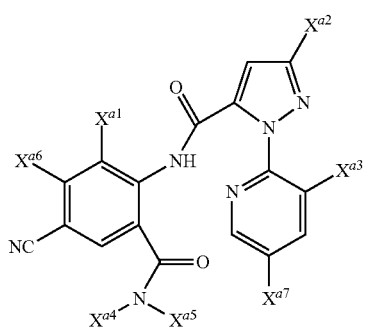

wherein $X^{a1}$ represents a methyl group, a chlorine atom, a bromine atom or a fluorine atom, $X^{a2}$ represents a fluorine atom, a chlorine atom, a bromine atom, a C1-C4 haloalkyl group or a C1-C4 haloalkoxy group, $X^{a3}$ represents a fluorine atom, a chlorine atom or a bromine atom, $X^{a4}$ represents an optionally substituted C1-C4 alkyl group, an optionally substituted C3-C4 alkenyl group, an optionally substituted C3-C4 alkynyl group, an optionally substituted C3-C5 cycloalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom;
a compound represented by the following formula (B):

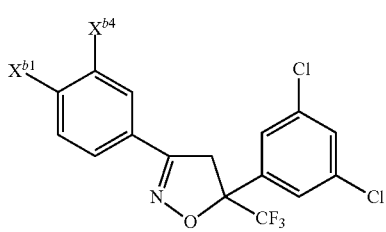

wherein $X^{b1}$ represents a $X^{b2}$—NH—C(=O) group, a $X^{b2}$—C(=O)—NH—CH$_2$— group, a $X^{b3}$—S(O) group, an optionally substituted pyrrol-1-yl group, an optionally substituted imidazol-1-yl group, an optionally substituted pyrazol-1-yl group, or an optionally substituted 1,2,4-triazol-1-yl group, $X^{b2}$ represents an optionally substituted C1-C4 haloalkyl group such as a 2,2,2-trifluoroethyl group or an optionally substituted C3-C6 cycloalkyl group such as a cyclopropyl group, $X^{b3}$ represents an optionally substituted C1-C4 alkyl group such as a methyl group, and $X^{b4}$ represents a hydrogen atom, a chlorine atom, a cyano group or a methyl group;
a compound represented by the following formula (C):

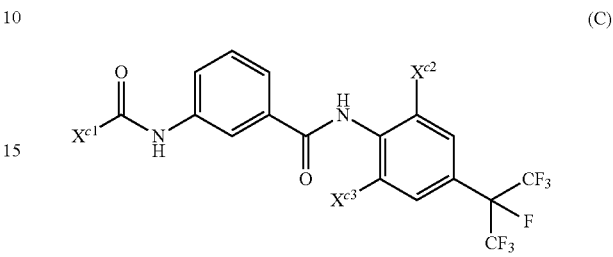

wherein $X^{c1}$ represents optionally an substituted C1-C4 alkyl group such as a 3,3,3-trifluoropropyl group, an optionally substituted C1-C4 alkoxy group such as a 2,2,2-trichloroethoxy group, an optionally substituted phenyl group such as a 4-cyanophenyl group or an optionally substituted pyridyl group such as a 2-chloro-3-pyridyl group, $X^{c2}$ represents a methyl group or a trifluoromethylthio group, and $X^{c3}$ represents a methyl group or a halogen atom; and the like.
Examples of an active ingredient of the acaricide include acequinocyl, amitraz, benzoximate, bifenazate, bromopropylate, thinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, cyenopyrafen, and the like.
Examples of the nematicide include DCIP, fosthiazate, levamisol hydrochloride, methylisothiocyanate, morantel tartarate, imicyafos, and the like.
Examples of the active ingredient for fungicides that can be used in combination include strobirulin compounds such as azoxystrobin, organic phosphorus compounds such as trichlophosmethyl, azole compounds such as triflumizole, pefurazoate and difenoconazole, fthalide, flutolanil, validamycin, probenazole, diclomezine, pencycuron, dazomet, kasugamycin, IBP, pyroquilon, oxolinic acid, tricyclazole, ferimzone, mepronil, EDDP, isoprothiolane, carpropamid, diclocymet, furametpyr, fludioxonil, procymidone and diethofencarb.
Hereinafter, the present invention will be described in more detail by way of Production Examples, Formulation Examples and Test Examples. However, the present invention is not limited thereto.
First, Production Examples of the present compound will be described.

PRODUCTION EXAMPLE 1

In 10 mL of methanol, 200 mg of 5-chloromethyl-2-trifluoromethylpyridine and 240 mg of S-(3,3,3-trifluoropropyl) benzenethioate were dissolved and 0.2 mL of sodium methoxide (28% methanol solution) was added dropwise thereto at room temperature. After stirring at the same temperature for 2 hour, 10% hydrochloric acid was added to the reaction mixture, followed by extraction with ethyl acetate. The organic layer was dried over anhydrous magnesium sulfate and concentrated under reduced pressure, and then the resulting residue was subjected to column chromatography to obtain 230 mg of 2-trifluoromethyl-5-(3,3,3-trifluoropropylsulfanylmethyl)pyridine (hereinafter referred to as the present compound (1)).
The Present Compound (1)

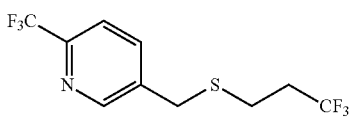

(1)

$^1$H-NMR (CDCl$_3$, TMS): δ(ppm) 8.66 (1H, d), 7.85 (1H, dd), 7.67 (1H, d), 3.80 (2H, s), 2.60-2.64 (2H, m), 2.31-2.43 (2H, m)

PRODUCTION EXAMPLE 2

In 20 mL of methanol, 300 mg of 5-chloromethyl-2-trifluoromethylpyridine and 359 mg of S-(3,3,3-trifluoropropyl)benzenethioate were dissolved and 0.3 mL of sodium methoxide (28% methanol solution) was added dropwise thereto at room temperature. After stirring at the same temperature for 18 hours, 10% hydrochloric acid was added to the reaction mixture, followed by extraction with chloroform. The organic layer was concentrated under reduced pressure and the resulting residue was dissolved in 10 mL of chloroform, and then 5 mL of peracetic acid (30% acetic acid solution) was added dropwise at room temperature. After stirring at the same temperature for 4 hours, a saturated sodium hydrogencarbonate solution was added, followed by extraction with ethyl acetate. The organic layer was dried over anhydrous magnesium sulfate and concentrated under reduced pressure, and then the resulting residue was subjected to column chromatography to obtain 180 mg of 2-trifluoromethyl-5-(3,3,3-trifluoropropanesulfonylmethyl)pyridine (hereinafter referred to as the present compound (2)).
The Present Compound (2)

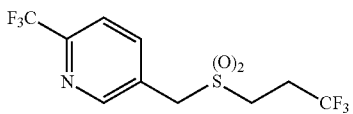

(2)

$^1$H-NMR (CDCl$_3$, TMS): δ(ppm) 8.75 (1H, d), 8.03 (1H, dd), 7.79 (1H, d), 4.38 (2H, s), 3.17-3.21 (2H, m), 2.64-2.76 (2H, m)

PRODUCTION EXAMPLE 3

In 50 mL of methanol, 1.12 g of 5-(1-bromoethyl)-2-trifluoromethylpyridine and 1.03 g of 5-(3,3,3-trifluoropropyl)benzenethioate were dissolved and 0.87 mL of sodium methoxide (28% methanol solution) was added dropwise thereto at room temperature. After stirring at the same temperature for 10 hours, 10% hydrochloric acid was added to the reaction mixture, followed by extraction with ethyl acetate. The organic layer was dried over anhydrous magnesium sulfate and concentrated under reduced pressure, and then the resulting residue was subjected to column chromatography to obtain 1.00 g of 2-trifluoromethyl-5-[1-(3,3,3-trifluoropropylsulfanyl)ethyl]pyridine (hereinafter referred to as the present compound (3)).

The Present Compound (3)

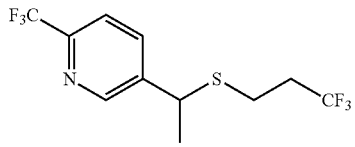

(3)

$^1$H-NMR (CDCl$_3$, TMS): δ(ppm) 8.68 (1H, s), 7.89 (1H, d), 7.68 (1H, d), 4.06 (1H, q), 2.52 (2H, t), 2.23-2.37 (2H, m), 1.63 (3H, d)

PRODUCTION EXAMPLE 4

In 30 mL of chloroform, 0.8 g of the present compound (3) was dissolved and 5 mL of peracetic acid (30% acetic acid solution) was added dropwise at room temperature. After stirring at the same temperature for 10 hours, a saturated sodium hydrogencarbonate solution was added, followed by extraction with ethyl acetate. The organic layer was dried over anhydrous magnesium sulfate and concentrated under reduced pressure, and then the resulting residue was subjected to column chromatography to obtain 0.64 g of 2-trifluoromethyl-5-[1-(3,3,3-trifluoropropanesulfonyl)ethyl]pyridine (hereinafter referred to as the present compound (4)).
The Present Compound (4)

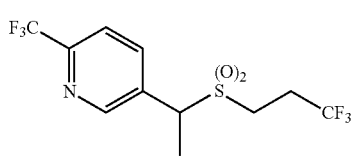

(4)

$^1$H-NMR (CDCl$_3$, TMS): δ(ppm) 8.75 (1H, s), 8.06 (1H, dd), 7.78 (1H, d), 4.35 (1H, q), 2.96-3.13 (2H, m), 2.55-2.73 (2H, m), 1.88 (3H, d)

PRODUCTION EXAMPLE 5

In 20 mL of methanol, 500 mg of 2-bromomethyl-5-chloropyridine and 567 mg of S-(3,3,3-trifluoropropyl)benzenethioate were dissolved and 0.5 mL of sodium methoxide (2'8% methanol solution) was added dropwise at room temperature. After stirring at the same temperature for 24 hours, 10% hydrochloric acid was added to the reaction mixture, followed by extraction with ethyl acetate. The organic layer was dried over anhydrous magnesium sulfate and concentrated under reduced pressure, and then the resulting residue was subjected to column chromatography to obtain 500 mg of 5-chloro-2-(3,3,3-trifluoropropylsulfanylmethyl)pyridine (hereinafter referred to as the present compound (5)).
The Present Compound (5)

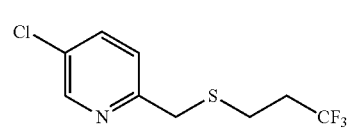

(5)

$^1$H-NMR (CDCl$_3$, TMS): δ(ppm) 8.49 (1H, d), 7.66 (1H, dd), 7.32 (1H, d), 3.83 (2H, s), 2.63-2.66 (2H, m), 2.32-2.43 (2H, m)

PRODUCTION EXAMPLE 6

In 20 mL of methanol, 435 mg of 2-(1-bromoethyl)-5-chloropyridine and 462 mg of 5-(3,3,3-trifluoropropyl)benzenethioate were dissolved and 0.4 mL of sodium methoxide (28% methanol solution) was added dropwise thereto at room temperature. After stirring at the same temperature for 10 hours, 10% hydrochloric acid was added to the reaction mixture, followed by extraction with ethyl acetate. The organic layer was dried over anhydrous magnesium sulfate and concentrated under reduced pressure, and then the resulting residue was subjected to column chromatography to obtain 300 mg of 5-chloro-2-[1-(3,3,3-trifluoropropylsulfanyl)ethyl]pyridine (hereinafter referred to as the present compound (6)).

The Present Compound (6)

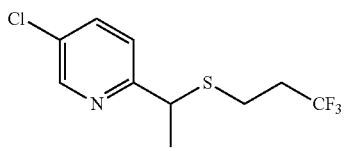

(6)

$^1$H-NMR (CDCl$_3$, TMS): δ(ppm) 8.48 (1H, d), 7.67 (1H, dd), 7.35 (1H, d), 4.09 (1H, q), 2.51-2.57 (2H, m), 2.19-2.40 (2H, m), 1.61 (3H, d)

PRODUCTION EXAMPLE 7

In 20 mL of methanol, 500 mg of 2-bromomethyl-5-trifluoromethylpyridine and 488 mg of 5-(3,3,3-trifluoropropyl)benzenethioate were dissolved and 0.4 mL of sodium methoxide (28% methanol solution) was added dropwise thereto at room temperature. After stirring at the same temperature for 10 minutes, 10% hydrochloric acid was added to the reaction mixture, followed by extraction with ethyl acetate. The organic layer was dried over anhydrous magnesium sulfate and concentrated under reduced pressure, and then the resulting residue was subjected to column chromatography to obtain 400 mg of 5-trifluoromethyl-2-(3,3,3-trifluoropropylsulfanylmethyl)pyridine (hereinafter referred to as the present compound (7)).

The Present Compound (7)

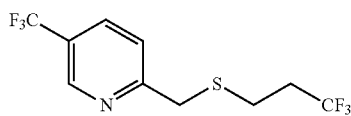

(7)

$^1$H-NMR (CDCl$_3$, TMS): δ(ppm) 8.80 (1H, s), 7.92 (1H, dd), 7.50 (1H, d), 3.91 (2H, s), 2.65-2.69 (2H, m), 2.34-2.46 (2H, m)

PRODUCTION EXAMPLE 8

In 20 mL of methanol, 452 mg of 2-(1-bromoethyl)-5-trifluoromethylpyridine and 417 mg of S-(3,3,3-trifluoropropyl)benzenethioate were dissolved and 0.4 mL of sodium methoxide (28% methanol solution) was added dropwise thereto at room temperature. After stirring at the same temperature for one hour, 10% hydrochloric acid was added to the reaction mixture, followed by extraction with ethyl acetate. The organic layer was dried over anhydrous magnesium sulfate and concentrated under reduced pressure, and then the resulting residue was subjected to column chromatography to obtain 760 mg of 5-trifluoromethyl-2-[1-(3,3,3-trifluoropropylsulfanyl)ethyl]pyridine (hereinafter referred to as the present compound (8)).

The Present Compound (8)

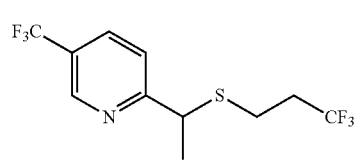

(8)

$^1$H-NMR (CDCl$_3$, TMS): δ(ppm) 8.79 (1H, d), 7.93 (1H, dd), 7.54 (1H, d), 4.17 (1H, q), 2.55-2.59 (2H, m), 2.31-2.39 (2H, m), 1.65 (3H, d)

PRODUCTION EXAMPLE 9

In 30 mL of chloroform, 680 mg of the present compound (8) was dissolved and 851 mg of meta-chloroperbenzoic acid was added thereto at room temperature. After stirring at the same temperature for 20 hours, a saturated sodium hydrogencarbonate solution was added, followed by extraction with ethyl acetate. The organic layer was dried over anhydrous magnesium sulfate and concentrated under reduced pressure, and then the resulting residue was subjected to column chromatography to obtain 580 mg of 5-trifluoromethyl-2-[1-(3,3,3-trifluoropropanesulfonyl)ethyl]pyridine (hereinafter referred to as the present compound (9)).

The Present Compound (9)

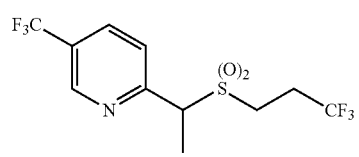

(9)

$^1$H-NMR (CDCl$_3$, TMS): δ(ppm) 8.88 (1H, s), 8.02 (1H, dd), 7.64 (1H, d), 4.52 (1H, q), 3.11-3.24 (2H, m), 2.54-2.70 (2H, m), 1.90 (3H, d)

PRODUCTION EXAMPLE 10

In 30 mL of methanol, 1.03 g of 5-bromomethyl-2-trifluoromethylpyrimidine and 1.00 g of S-(3,3,3-trifluoropropyl)benzenethioate were dissolved and 0.8 mL of sodium methoxide (28% methanol solution) was added dropwise thereto at room temperature. After stirring at the same temperature for 6 hours, 10% hydrochloric acid was added to the reaction mixture, followed by extraction with ethyl acetate. The organic layer was dried over anhydrous magnesium sulfate and concentrated under reduced pressure, and then the resulting residue was subjected to column chromatography to obtain 330 mg of 2-trifluoromethyl-5-(3,3,3-trifluoropropylsulfanylmethyl)pyrimidine (hereinafter referred to as the present compound (10)).

The Present Compound (10)

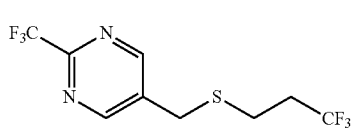

¹H-NMR (CDCl₃, TMS): δ(ppm) 8.86 (2H, s), 3.80 (2H, s), 2.65-2.69 (2H, m), 2.34-2.46 (2H, m)

PRODUCTION EXAMPLE 11

In 50 mL of methanol, 1.10 g of 2-chloro-5-bromomethylpyrimidine and 1.24 g of S-(3,3,3-trifluoropropyl)benzenethioate were dissolved and 1.0 mL of sodium methoxide (28% methanol solution) was added dropwise thereto at room temperature. After stirring at the same temperature for 4 hours, 10% hydrochloric acid was added to the reaction mixture, followed by extraction with ethyl acetate. The organic layer was dried over anhydrous magnesium sulfate and concentrated under reduced pressure, and then the resulting residue was subjected to column chromatography to obtain 90 mg of 2-chloro-5-(3,3,3-trifluoropropylsulfanylmethyl)pyrimidine (hereinafter referred to as the present compound (11)) and 260 mg of 2-methoxy-5-(3,3,3-trifluoropropylsulfanylmethyl)pyrimidine (hereinafter referred to as the present compound (12)).

The Present Compound (11)

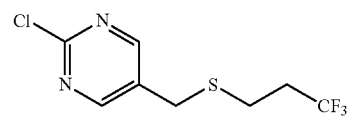

¹H-NMR (CDCl₃, TMS): δ(ppm) 8.60 (2H, s), 3.70 (2H, s), 2.63-2.67 (2H, m), 2.32-2.44 (2H, m)

The Present Compound (12)

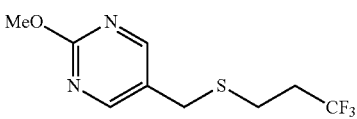

¹H-NMR (CDCl₃, TMS): δ(ppm) 8.47 (2H, s), 4.03 (3H, s), 3.67 (2H, s), 2.61-2.65 (2H, m), 2.31-2.43 (2H, m)

PRODUCTION EXAMPLE 12

In 20 mL of dimethyl sulfoxide, 635 mg of 2-chloro-5-trifluoromethylpyridine and 703 g of methyl (3,3,3-trifluoropropylsulfonyl)acetate were dissolved and 1.14 g of cesium carbonate was added thereto at room temperature, followed by stirring at 110° C. for 10 hours. To the reaction mixture was added 10% hydrochloric acid, followed by extraction with ethyl acetate. The organic layer was dried over anhydrous sodium sulfate and concentrated under reduced pressure, and then the resulting residue was subjected to silica gel column chromatography to obtain 360 mg of methyl 2-(5-trifluoromethylpyridin-2-yl)-2-(3,3,3-trifluoropropylsulfonyl)acetate (hereinafter referred to as the present compound (13)).

The Present Compound (13)

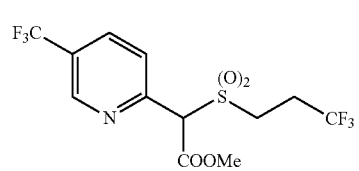

¹H-NMR (CDCl₃, TMS): δ(ppm) 8.90 (1H, m), 8.07 (1H, dd), 7, 85 (1H, d), 5.34 (1H, s), 3.87 (3H, s), 3.77 (1H, ddd), 3.46 (1H, ddd), 2.79-2.54 (2H, m)

PRODUCTION EXAMPLE 13

In 5.0 mL of N,N-dimethylformamide, 472 mg of the present compound (13) was dissolved and 244 mg of N-chlorosuccinimide was added thereto at room temperature. After stirring at the same temperature for one hour, the reaction mixture was subjected to silica gel column chromatography to obtain 410 mg of methyl 2-chloro-2-(5-trifluoromethylpyridin-2-yl)-2-(3,3,3-trifluoropropylsulfonyl)acetate (hereinafter referred to as the present compound (14)).

The Present Compound (14)

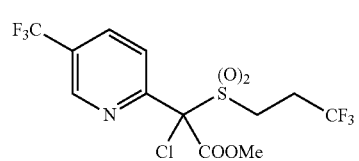

¹H-NMR (CDCl₃, TMS): δ(ppm) 8.88 (1H, m), 8.15-8.12 (2H, m), 3.99 (1H, ddd), 3.94 (3H, s), 3.58 (1H, ddd), 2.85-2.55 (2H, m)

PRODUCTION EXAMPLE 14

The present compound (14) was dissolved in 5.0 mL of methanol and 2.0 mL of ammonia water (28% aqueous solution) was added thereto at room temperature. After stirring at the same temperature for 2 hours, the solution was concentrated under reduced pressure and the resulting residue was subjected to silica gel column chromatography to obtain 352 mg of 2-[chloro-(3,3,3-trifluoropropanesulfonyl)methyl]-5-trifluoromethylpyridine (hereinafter referred to as the present compound (15)).

The Present Compound (15)

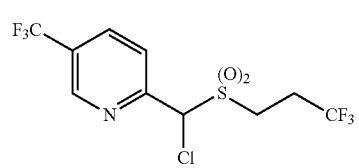

¹H-NMR (CDCl₃, TMS): δ(ppm) 8.94 (1H, s), 8.10 (1H, dd), 7.86 (1H, d), 5.86 (1H, s), 3.63-3.55 (2H, m), 2.84-2.64 (2H, m)

Specific examples of the present compounds will be shown below:

the compounds represented by (I¹)

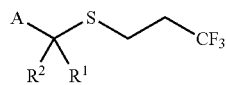
(I¹)

(wherein $R^1$, $R^2$ and A are any of combinations shown below);
the compounds represented by (I²)

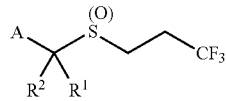
(I²)

(wherein $R^1$, $R^2$ and A are any of combinations shown below);
the compounds represented by (I³)

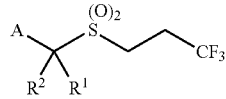
(I³)

(wherein $R^1$, $R^2$ and A are any of combinations shown below);
the compounds represented by (I⁴)

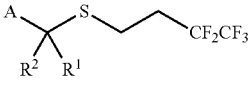
(I⁴)

(wherein $R^1$, $R^2$ and A are any of combinations shown below);
the compounds represented by (I⁵)

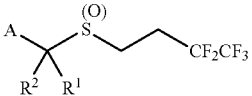
(I⁵)

(wherein $R^1$, $R^2$ and A are any of combinations shown below);
the compounds represented by (I⁶)

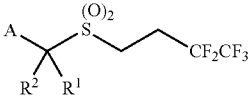
(I⁶)

(wherein $R^1$, $R^2$ and A are any of combinations shown below);
compound represented by (I⁷)

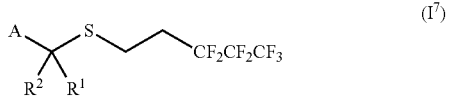
(I⁷)

(wherein $R^1$, $R^2$ and A are any of combinations shown below);
the compounds represented by (I⁸)

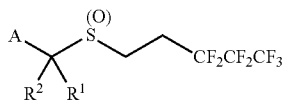
(I⁸)

(wherein $R^1$, $R^2$ and A are any of combinations shown below);
the compounds represented by (I⁹)

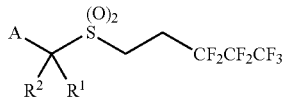
(I⁹)

(wherein $R^1$, $R^2$ and A are any of combinations shown below);
the compounds represented by (I¹⁰)

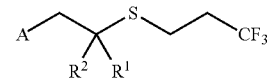
(I¹⁰)

(wherein R', $R^2$ and A are any of combinations shown below);
the compounds represented by (I¹¹)

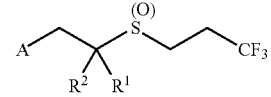
(I¹¹)

(wherein $R^1$, $R^2$ and A are any of combinations shown below);
the compounds represented by (I¹²)

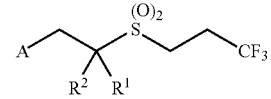
(I¹²)

(wherein R$^1$, R$^2$ and A are any of combinations shown below);
the compounds represented by (I$^{13}$)

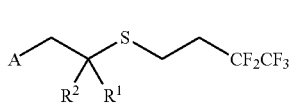
(I$^{13}$)

(wherein R$^1$, R$^2$ and A are any of combinations shown below);
the compounds represented by (I$^{14}$)

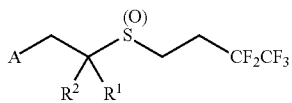
(I$^{14}$)

(wherein R$^1$, R$^2$ and A are any of combinations shown below);
the compounds represented by (I$^{15}$)

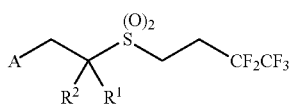
(I$^{15}$)

(wherein R$^1$, R$^2$ and A are any of combinations shown below);
the compounds represented by (I$^{16}$)

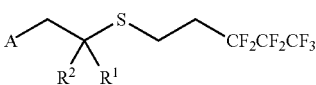
(I$^{16}$)

(wherein R$^1$, R$^2$ and A are any of combinations shown below);
the compounds represented by (I$^{17}$)

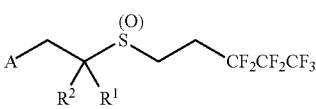
(I$^{17}$)

(wherein R$^1$, R$^2$ and A are any of combinations shown below);
the compounds represented by (I$^{18}$)

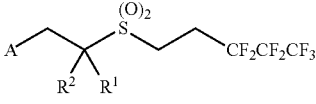
(I$^{18}$)

(wherein R$^1$, R$^2$ and A are any of combinations shown below);
the compounds represented by (I$^{19}$)

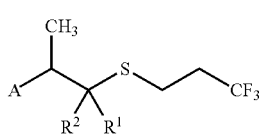
(I$^{19}$)

(wherein R$^1$, R$^2$ and A are any of combinations shown below);
the compounds represented by (I$^{20}$)

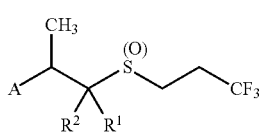
(I$^{20}$)

(wherein R$^1$, R$^2$ and A are any of combinations shown below);
the compounds represented by (I$^{21}$)

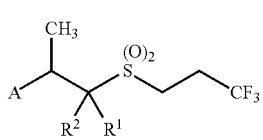
(I$^{21}$)

(wherein R$^1$, R$^2$ and A are any of combinations shown below);
the compounds represented by (I$^{22}$)

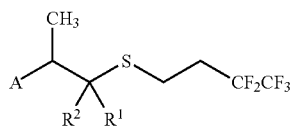
(I$^{22}$)

(wherein R$^1$, R$^2$ and A are any of combinations shown below);
the compounds represented by (I$^{23}$)

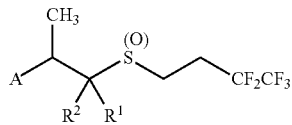
(I$^{23}$)

(wherein R$^1$, R$^2$ and A are any of combinations shown below);
the compounds represented by (I$^{24}$)

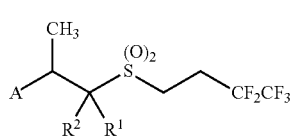
(I$^{24}$)

(wherein $R^1$, $R^2$ and A are any of combinations shown below); the compounds represented by ($I^{25}$)

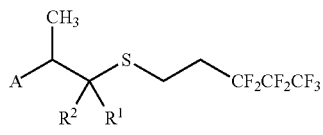
($I^{25}$)

(wherein $R^1$, $R^2$ and A are any of combinations shown below); the compounds represented by ($I^{26}$)

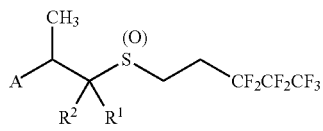
($I^{26}$)

(wherein $R^1$, $R^2$ and A are any of combinations shown below); the compounds represented by ($I^{27}$)

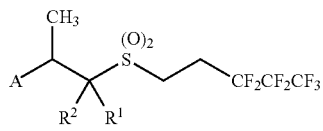
($I^{27}$)

(wherein $R^1$, $R^2$ and A are any of combinations shown below); the compounds represented by ($I^{28}$)

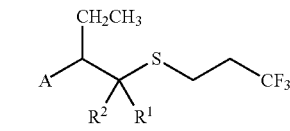
($I^{28}$)

(wherein $R^1$, $R^2$ and A are any of combinations shown below); the compounds represented by ($I^{29}$)

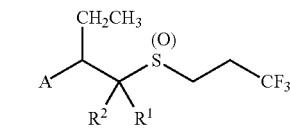
($I^{29}$)

(wherein $R^1$, $R^2$ and A are any of combinations shown below); the compounds represented by ($I^{30}$)

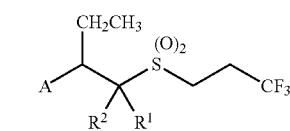
($I^{30}$)

(wherein $R^1$, $R^2$ and A are any of combinations shown below); the compounds represented by ($I^{31}$)

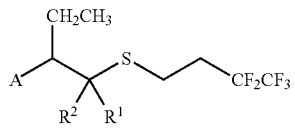
($I^{31}$)

(wherein $R^1$, $R^2$ and A are any of combinations shown below); the compounds represented by ($I^{32}$)

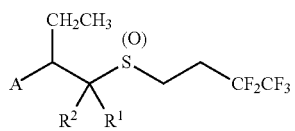
($I^{32}$)

(wherein $R^1$, $R^2$ and A are any of combinations shown below); the compounds represented by ($I^{33}$)

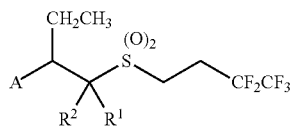
($I^{33}$)

(wherein $R^1$, $R^2$ and A are any of combinations shown below); the compounds represented by ($I^{34}$)

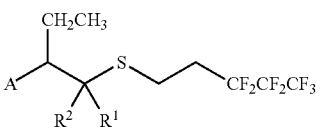
($I^{34}$)

(wherein $R^1$, $R^2$ and A are any of combinations shown below); the compounds represented by ($I^{35}$)

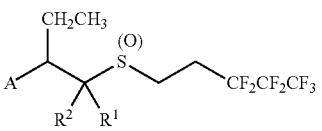
($I^{35}$)

(wherein $R^1$, $R^2$ and A are any of combinations shown below); the compounds represented by ($I^{36}$)

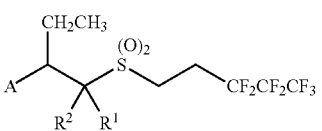
($I^{36}$)

(wherein $R^1$, $R^2$ and A are any of combinations shown below); the compounds represented by ($I^{37}$)

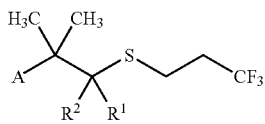

(wherein $R^1$, $R^2$ and A are any of combinations shown below); the compounds represented by ($I^{38}$)

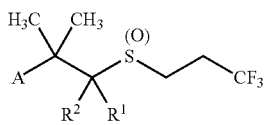

(wherein $R^1$, $R^2$ and A are any of combinations shown below); the compounds represented by ($I^{39}$)

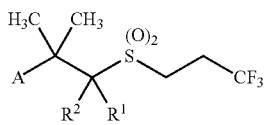

(wherein $R^1$, $R^2$ and A are any of combinations shown below); the compounds represented by ($I^{40}$)

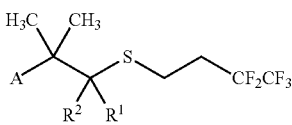

(wherein $R^1$, $R^2$ and A are any of combinations shown below); the compounds represented by ($I^{41}$)

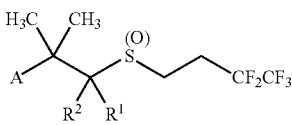

(wherein $R^1$, $R^2$ and A are any of combinations shown below); the compounds represented by ($I^{42}$).

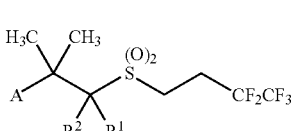

(wherein $R^1$, $R^2$ and A are any of combinations shown below); the compounds represented by ($I^{43}$)

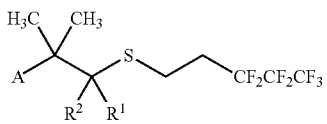

(wherein $R^1$, $R^2$ and A are any of combinations shown below); the compounds represented by ($I^{44}$)

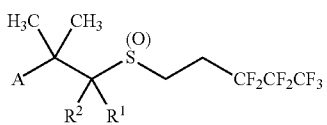

(wherein $R^1$, $R^2$ and A are any of combinations shown below); and the compounds represented by ($I^{45}$)

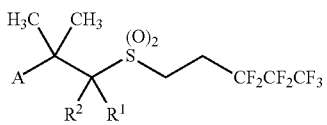

(wherein $R^1$, $R^2$ and A are any of combinations shown below).

Combinations of $R^1$, $R^2$ and A in the compounds represented by the formulas ($I^1$) to ($I^{45}$) will be described below. In the following parentheses, a branch number, a group represented by $R^1$, a group represented by $R^2$, and a group represented by A are described in this order.

[Branch number: $R^1$, $R^2$, A]=
[1:H, H, A1], [2:H, F, A1], [3:H, Cl, A1], [4:H, Br, A1], [5:H, CH$_3$, A1], [6:H, CH$_2$CH$_3$, A1], [7:F, F, A1], [8:F, Cl, A1], [9:F, Br, A1], [10:F, CH$_3$, A1], [11:F, CH$_2$CH$_3$, A1], [12:Cl, Cl, A1], [13:Cl, Br, A1], [14:Cl, CH$_3$, A1], [15:Cl, CH$_2$CH$_3$, A1], [16:Br, Br, A1], [17:Br, CH$_3$, A1], [18:Br, CH$_2$CH$_3$, A1], [19:CH$_3$, CH$_3$, A1], [20:CH$_3$, CH$_2$CH$_3$, A1], [21:CN, H, A1], [22:CN, F, A1], [23:CN, Cl, A1], [24:CN, Br, A1], [25:CN, CH$_3$, A1], [26:CN, CH$_2$CH$_3$, A1], [27:C(=O)OCH$_3$, H, A1], [28:C(=O)OCH$_3$, F, A1], [29:C(=O) OCH$_3$, Cl, A1], [30:C(=O)OCH$_3$, Br, A1], [31:C(=O)OCH$_3$, CH$_3$, A1], [32:C(=O)OCH$_3$, CH$_2$CH$_3$, A1], [33:C(=O)O(CH$_3$)$_3$, H, A1], [34:C(=O)O(CH$_3$)$_3$, F, A1], [35:C(=O)O(CH$_3$)$_3$, Cl, A1], [36:C(=O)O(CH$_3$)$_3$, Br, A1], [37:C(=O)O(CH$_3$)$_3$, CH$_3$, A1], [38:C(=O)O(CH$_3$)$_3$, CH$_2$CH$_3$, A1], [39:C(=O)NH$_2$, H, A1], [40:C(=O)NH$_2$, F, A1], [41:C(=O)NH$_2$, Cl, A1], [42:C(=O)NH$_2$, Br, A1], [43:C(=O)NH$_2$, CH$_3$, A1], [44: C(=O)NH$_2$, CH$_2$CH$_3$, A1], [45:C(=O)NH(CH$_3$), H, A1], [46:C(=O)NH(CH$_3$), F, A1], [47:C(=O)NH(CH$_3$)Cl, A1], [48:C(=O)NH(CH$_3$), Br, A1], [49:C(=O)NH(CH$_3$), CH$_3$, A1], [50:C(=O)NH(CH$_3$), CH$_2$CH$_3$, A1], [51:C(=O)NH(CH$_2$CH$_3$), H, A1], [52:C(=O)NH(CH$_2$CH$_3$), F, A1], [53:C(=O)NH(CH$_2$CH$_3$), Cl, A1], [54:C(=O)NH(CH$_2$CH$_3$), Br, A1], [55:C(=O)NH(CH$_2$CH$_3$), CH$_3$, A1], [56:C(=O)NH(CH$_2$CH$_3$), CH$_2$CH$_3$, A1], [57:C(=O)N(CH$_3$)$_2$, H, A1], [58:C(=O)N(CH$_3$)$_2$, F, A1], [59:C(=O)N(CH$_3$)$_2$, Cl, A1], [60:C(=O)N(CH$_3$)$_2$, Br, A1], [61:C (=O)N(CH₃)₂, CH₃, A1], [62:C(=O)N(CH₃)₂, CH₂CH₃, A1], [63:C(=S)OCH₃, H, A1], [64:C(=S)OCH₃, F, A1], [65:C(=S)OCH₃, Cl, A1], [66:C(=S)OCH₃, Br, A1], [67:C(=S)OCH₃, CH₃, A1], [68:C(=S)OCH₃, CH₂CH₃, A1], [69:C(=S)NH₂, H, A1], [70:C(=S)NH₂, F, A1], [71:C(=S)NH₂, Cl, A1], [72:C(=S)NH₂, Br, A1], [73:C(=S)NH₂, CH₃, A1], [74:C(=S)NH₂, CH₂CH₃, A1], [75:C(=S)NH(CH₃), H, A1], [76:C(=S)NH(CH₃), F, A1], [77:C(=S)NH(CH₃), Cl, A1], [78:C(=S)NH(CH₃), Br, A1], [79:C(=S)NH(CH₃), CH₃, A1], [80:C(=S)NH(CH₃), CH₂CH₃, A1], [81:C(=S)N(CH₃)₂, H, A1], [82:C(=S)N(CH₃)₂, F, A1], [83:C(=S)N(CH₃)₂, Cl, A1], [84:C(=S)N(CH₃)₂, Br, A1], [85:C(=S)N(CH₃)₂CH₃, A1 ], [86:C(=S)N(CH₃)₂, CH₂CH₃, A1], [87:H, H, A2], [88:H, F, A2], [89:H, Cl, A2], [90:H, Br, A2], [91:H, CH₃, A2], [92:H, CH₂CH₃, A2], [93:F, F, A2], [94:F, Cl, A2], [95:F, Br, A2], [96:F, CH₃, A2], [97:F, CH₂CH₃, A2], [98:Cl, Cl, A2], [99:Cl, Br, A2], [100:Cl, CH₃, A2], [101:Cl, CH₂CH₃, A2], [102:Br, Br, A2], [103:Br, CH₃, A2], [104:Br, CH₂CH₃, A2], [105:CH₃, CH₃, A2], [106:CH₃, CH₂CH₃, A2], [107:CN, H, A2], [108:CN, F, A2], [109:CN, Cl, A2], [110:CN, Br, A2], [111:CN, CH₃, A2], [112:CN, CH₂CH₃, A2], [113:C(=O)OCH₃, H, A2], [114:C(=O)OCH₃, F, A2], [115:C(=O)OCH₃, Cl, A2], [116:C(=O)OCH₃, Br, A2], [117:C(=O)OCH₃, CH₃, A2], [118:C(=O) OCH₃, CH₂CH₃, A2], [119:C(=O)O(CH₃)₃, H, A2], [120:C(=O)O(CH₃)₃, F, A2], [121:C(=O)O(CH₃)₃, Cl, A2], [122:C(=O)O(CH₃)₃, Br, A2], [123:C(=O)O(CH₃)₃, CH₃, A2], [124:C(=O)O(CH₃)₃, CH₂CH₃, A2], [125:C(=O)NH₂,H,A2], [126:C(=O)NH₂,F,A2], [127:C(=O)NH₂, Cl, A2], [128:C(=O)NH₂, Br, A2], [129:C(=O)NH₂, CH₃, A2], [130:C(=O)NH₂, CH₂CH₃, A2], [131:C(=O)NH(CH₃), H, A2], [132:C(=O)NH(CH₃), F, A2], [133:C(=O)NH(CH₃), Cl, A2], [134:C(=O)NH(CH₃), Br, A2], [135:C(=O)NH(CH₃), CH₃, A2], [136:C(=O)NH(CH₃), CH₂CH₃, A2], [137:C(=O)NH(CH₂CH₃), H, A2], [138:C(=O)NH(CH₂CH₃), F, A2], [139:C(=O)NH(CH₂CH₃), Cl, A2], [140:C(=O)NH(CH₂CH₃), Br, A2], [141:C(=O) (CH₂CH₃), CH₃, A2], [142:C(=O)NH(CH₂CH₃), CH₂CH₃, A2], [143:C(=O)N(CH₃)₂, H, A2], [144:C(=O)N(CH₃)₂, F, A2], [145:C(=O)N(CH₃)₂, Cl, A2], [146:C(=O)N(CH₃)₂, Br, A2], [147:C(=O)N(CH₃)₂, CH₃, A2], [148:C(=O)N(CH₃)₂, CH₂CH₃, A2], [149:C(=S)OCH₃, H, A2], [150:C(=S)OCH₃, F, A2], [151:C(=S)OCH₃, Cl, A2], [152:C(=S)OCH₃, Br, A2], [153:C(=S)OCH₃, CH₃, A2], [154:C(=S)OCH₃, CH₂CH₃, A2], [155:C(=S)NH₂, H, A2], [156:C(=S)NH₂, F, A2], [157:C(=S)NH₂, Cl, A2], [158:C(=S)NH₂, Br, A2], [159:C(=S)NH₂, CH₃, A2], [160:C(=S)NH₂, CH₂CH₃, A2], [161:C(=S)NH(CH₃), H, A2], [162:C(=S)NH(CH₃), F, A2], [163:C(=S)NH(CH₃), Cl, A2], [164:C(=S)NH(CH₃), Br, A2], [165:C(=S)NH(CH₃), CH₃, A2], [166:C(=S)NH(CH₃), CH₂CH₃, A2], [167:C(=S)N(CH₃)₂, H, A2], [168:C(=S)N(CH₃)₂, F, A2], [169:C(=S)N(CH₃)₂, Cl, A2], [170:C(=S)N(CH₃)₂, Br, A2], [171:C(=S)N(CH₃)₂, CH₃, A2], [172:C(=S)N(CH₃)₂, CH₂CH₃, A2], [173:H, H, A3], [174:H, F, A3], [175:H, Cl, A3], [176: H, Br, A3], [177:H, CH₃, A3], [178:H, CH₂CH₃, A3], [179:F, F, A3], [180: F, Cl, A3], [181:F, Br, A3], [182:F, CH₃, A3], [183:F, CH₂CH₃, A3], [184:Cl, Cl, A3], [185:Cl, Br, A3], [186:Cl, CH₃, A3], [187:Cl, CH₂CH₃, A3], [188:Br, Br, A3], [189:Br, CH₃, A3], [190: Br, CH₂CH₃, A3], [191:CH₃, CH₃, A3], [192:CH₃, CH₂CH₃, A3], [193:CN, H, A3], [194:CN, F, A3], [195:CN, Cl, A3], [196:CN, Br, A3], [197:CN, CH₃, A3], [198:CN, CH₂CH₃, A3], [199:C(=O)OCH₃, H, A3], [200:C(=O)OCH₃, F, A3], [201:C(=O)OCH₃, Cl, A3], [202:C(=O)OCH₃, Br, A3], [203:C(=O)OCH₃, CH₃, A3], [204:C(=O)OCH₃, CH₂CH₃, A3], [205:C(=O)O(CH₃)₃, H, A3], [206:C(=O)O(CH₃)₃, F, A3], [207:C(=O)O(CH₃)₃, Cl, A3], [208:C(=O)O(CH₃)₃, Br, A3], [209:C(=O)O(CH₃)₃, CH₃, A3], [210:C(=O)O(CH₃)₃, CH₂CH₃, A3], [211:C(=O)NH₂, H, A3], [212:C(=O)NH₂, F, A3], [213:C(=O)NH₂, Cl, A3], [214:C(=O)NH₂, Br, A3], [215:C(=O)NH₂, CH₃, A3], [216:C(=O)NH₂, CH₂CH₃, A3], [217:C(=O)NH(CH₃), H, A3], [218:C(=O)NH(CH₃), F, A3], [219:C(=O)NH(CH₃), Cl, A3], [220:C(=O)NH(CH₃), Br, A3], [221:C(=O)NH(CH₃), CH₃, A3], [222:C(=O)NH(CH₃), CH₂CH₃, A3], [223:C(=O)NH(CH₂CH₃), H, A3], [224:C(=O)NH(CH₂CH₃), F, A3], [225:C(=O)NH(CH₂CH₃), Cl, A3], [226:C(=O)NH(CH₂CH₃), Br, A3], [227:C(=O)NH(CH₂CH₃), CH₃, A3], [228:C(=O)NH(CH₂CH₃), CH₂CH₃, A3], [229:C(=O)N(CH₃)₂, H, A3], [230:C(=O)N(CH₃)₂, F, A3], [231:C(=O)N(CH₃)₂, Cl, A3], [232:C(=O)N(CH₃)₂, Br, A3], [233:C(=O)N(CH₃)₂, CH₃, A3], [234:C(=O)N(CH₃)₂, CH₂CH₃, A3], [235:C(=S)OCH₃, H, A3], [236:C(=S)OCH₃, F, A3], [237:C(=S)OCH₃, Cl, A3], [238:C(=S)OCH₃, Br, A3], [239:C(=S)OCH₃, CH₃, A3], [240:C(=S)OCH₃, CH₂CH₃, A3], [241:C(=S)NH₂, H, A3], [242:C(=S)NH₂, F, A3], [243:C(=S)NH₂, Cl, A3], [244:C(=S)NH₂, Br, A3], [245:C(=S)NH₂, CH₃, A3], [246:C(=S)NH₂, CH₂CH₃, A3], [247:C(=S)NH(CH₃), H, A3], [248:C(=S)NH(CH₃), F, A3], [249:C(=S)NH(CH₃), Cl, A3], [250:C(=S)NH(CH₃), Br, A3], [251:C(=S)NH(CH₃), CH₃, A3], [252:C(=S)NH(CH₃), CH₂CH₃, A3], [253:C(=S)N(CH₃)₂, H, A3], [254:C(=S)N(CH₃)₂, F, A3], [255:C(=S)N(CH₃)₂, Cl, A3], [256:C(=S)N(CH₃)₂, Br, A3], [257:C(=S)N(CH₃)₂, CH₃, A3], [258:C(=S)N(CH₃)₂, CH₂CH₃, A3], [259:H, H, A4], [260:H, F, A4], [261:H, Cl, A4], [262:H, Br, A4], [263:H, CH₃, A4], [264:H, CH₂CH₃, A4], [265:F, F, A4], [266:F, Cl, A4], [267:F, Br, A4], [268: F, CH₃, A4], [269:F, CH₂CH₃, A4], [270:Cl, Cl, A4], [271:Cl, Br, A4], [272:Cl, CH₃, A4], [273:Cl, CH₂CH₃, A4], [274:Br, Br, A4], [275:Br, CH₃, A4], [276: Br, CH₂CH₃, A4], [277:CH₃, CH₃, A4], [278:CH₃, CH₂CH₃, A4], [279:CN, H, A4], [280:CN, F, A4], [281:CN, Cl, A4], [282:CN, Br, A4], [283:CN, CH₃, A4], [284:CN, CH₂CH₃, A4], [285:C(=O)OCH₃, H, A4], [286:C(=O)OCH₃, F, A4], [287:C(=O)OCH₃, Cl, A4], [288:C(=O)OCH₃, Br, A4], [289:C(=O)OCH₃, CH₃, A4], [290:C(=O)OCH₃, CH₂CH₃, A4], [291:C(=O)O(CH₃)₃, H, A4], [292:C(=O)O(CH₃)₃, F, A4], [293:C(=O)O(CH₃)₃, Cl, A4], [294:C(=O)O(CH₃)₃, Br, A4], [295:C(=O)O(CH₃)₃, CH₃, A4], [296:C(=O)O(CH₃)₃, CH₂CH₃, A4], [297:C(=O)NH₂, H, A4], [298:C(=O)NH₂, F, A4], [299:C(=O)NH₂, Cl, A4], [300:C(=O)NH₂, Br, A4], [301:C(=O)NH₂, CH₃, A4], [302:C(=O)NH₂, CH₂CH₃, A4], [303:C(=O)NH(CH₃), H, A4], [304:C(=O)NH(CH₃), F, A4], [305:C(=O)NH(CH₃), Cl, A4], [306:C(=O)NH(CH₃), Br, A4], [307:C(=O)NH(CH₃), CH₃, A4], [308:C(=O)NH(CH₃), CH₂CH₃, A4], [309:C(=O)NH(CH₂CH₃), H, A4], [310:C(=O)NH(CH₂CH₃), F, A4], [311:C(=O)NH(CH₂CH₃), Cl, A4], [312:C(=O)NH(CH₂CH₃), Br, A4], [313:C(=O)NH(CH₂CH₃), CH₃, A4], [314:C(=O)NH(CH₂CH₃), CH₂CH₃, A4], [315:C(=O)N(CH₃)₂, H, A4], [316:C(=O)N(CH₃)₂, F, A4], [317:C(=O)N(CH₃)₂, Cl, A4], [318:C(=O)N(CH₃)₂, Br, A4], [319:C(=O)N(CH₃)₂, CH₃, A4], [320:C(=O)N(CH₃)₂, CH₂CH₃, A4], [321:C(=S)OCH₃, H, A4], [322:C(=S)OCH₃, F, A4], [323:C(=S)OCH₃, Cl, A4], [324:C(=S)OCH₃, CH₃, A4], [325:C(=S)OCH₃, Br, A4], [326:C(=S)OCH₃, CH₂CH₃, A4], [327:C(=S)NH₂, H, A4], [328:C(=S)NH₂, F, A4], [329:C(=S)NH₂, Cl, A4], [330:

C(=S)NH₂, Br, A4], [331:C(=S)NH₂, CH₃, A4], [332:C(=S)NH₂, CH₂CH₃, A4], [333:C(=S)NH(CH₃), H, A4], [334:C(=S)NH(CH₃), F, A4], [335:C(=S)NH(CH₃), Cl, A4], [336:C(=S)NH(CH₃), Br, A4], [337:C(=S)NH(CH₃), CH₃, A4], [338:C(=S)NH(CH₃), CH₂CH₃, A4], [339:C(=S)N(CH₃)₂, H, A4], [340:C(=S)N(CH₃)₂, F, A4], [341:C(=S)N(CH₃)₂, Cl, A4], [342:C(=S)N(CH₃)₂, Br, A4], [343:C(=S)N(CH₃)₂, CH₃, A4], [344:C(=S)N(CH₃)₂, CH₂CH₃, A4], [345:H, H, A5], [346:H, F, A5], [347:H, Cl, A5], [348:H, Br, A5], [349:H, CH₃, A5], [350:H, CH₂CH₃, A5], [351:F, F, A5], [352:F, Cl, A5], [353:F, Br, A5], [354:F, CH₃, A5], [355:F, CH₂CH₃, A5], [356:Cl, Cl, A5], [357:Cl, Br, A5], [358:Cl, CH₃, A5], [359:Cl, CH₂CH₃, A5], [360:Br, Br, A5], [361:Br, CH₃, A5], [362:Br, CH₂CH₃, A5], [363:CH₃, CH₃, A5], [364:CH₃, CH₂CH₃, A5], [365:CN, H, A5], [366:CN, F, A5], [367:CN, Cl, A5], [368:CN, Br, A5], [369:CN, CH₃, A5], [370:CH₂CH₃, A5], [371:C(=O)OCH₃, H, A5], [372:C(=O)OCH₃, F, A5], [373:C(=O)OCH₃, Cl, A5], [374:C(=O)OCH₃, Br, A5], [375:C(=O)OCH₃, CH₃, A5], [376:C(=O)OCH₃, CH₂CH₃, A5], [377:C(=O)O(CH₃)₃, H, A5], [378:C(=O)O(CH₃)₃, F, A5], [379:C(=O)O(CH₃)₃, Cl, A5], [380:C(=O)O(CH₃)₃, Br, A5], [381:C(=O)O(CH₃)₃, CH₃, A5], [382:C(=O)O(CH₃)₃, CH₂CH₃, A5], [383:C(=O)NH₂, H, A5], [384:C(=O)NH₂, F, A5], [385:C(=O)NH₂, Cl, A5], [386:C(=O)NH₂, Br, A5], [387:C(=O)NH₂, CH₃, A5], [388:C(=O)NH₂, CH₂CH₃, A5], [389:C(=O)NH(CH₃), H, A5], [390:C(=O)NH(CH₃), F, A5], [391:C(=O)NH(CH₃), Cl, A5], [392:C(=O)NH(CH₃), Br, A5], [393:C(=O)NH(CH₃), CH₃, A5], [394:C(=O)NH(CH₃), CH₂CH₃, A5], [395:C(=O)NH(CH₂CH₃), H, A5], [396:C(=O)NH(CH₂CH₃), F, A5], [397:C(=O)NH(CH₂CH₃), Cl, A5], [398:C(=O)NH(CH₂CH₃), Br, A5], [399:C(=O)NH(CH₂CH₃), CH₃, A5], [400:C(=O)NH(CH₂CH₃)CH₂CH₃, A5], [401:C(=O)N(CH₃)₂, H, A5], [402:C(=O)N(CH₃)₂, F, A5], [403:C(=O)N(CH₃)₂, Cl, A5], [404:C(=O)N(CH₃)₂, Br, A5], [405:C(=O)N(CH₃)₂, CH₃, A5], [406:C(=O)N(CH₃)₂, CH₂CH₃, A5], [407:C(=S)OCH₃, H, A5], [408:C(=S)OCH₃, F, A5], [409:C(=S)OCH₃, Cl, A5], [410:C(=S)OCH₃, Br, A5], [411:C(=S)OCH₃, CH₃, A5], [412:C(=S)OCH₃, CH₂CH₃, A5], [413:C(=S)NH₂, H, A5], [414:C(=S)NH₂, F, A5], [415:C(=S)NH₂, Cl, A5], [416:C(=S)NH₂, Br, A5], [417:C(=S)NH₂, CH₃, A5], [418:C(=S)NH₂, CH₂CH₃, A5], [419:C(=S)NH(CH₃), H, A5], [420:C(=S)NH(CH₃), F, A5], [421:C(=S)NH(CH₃), Cl, A5], [422:C(=S)NH(CH₃), Br, A5], [423:C(=S)NH(CH₃), CH₃, A5], [424:C(=S)NH(CH₃), CH₂CH₃, A5], [425:C(=S)N(CH₃)₂, H, A5], [426:C(=S)N(CH₃)₂, F, A5], [427:C(=S)N(CH₃)₂, Cl, A5], [428:C(=S)N(CH₃)₂, Br, A5], [429:C(=S)N(CH₃)₂, CH₃, A5], [430:C(=S)N(CH₃)₂, CH₂CH₃, A5], [431:H, H, A6], [432:H, F, A6], [433:H, Cl, A6], [434:H, Br, A6], [435:H, CH₃, A6], [436:H, CH₂CH₃, A6], [437:F, F, A6], [438:F, Cl, A6], [439:F, Br, A6], [440:F, CH₃, A6], [441:F, CH₂CH₃, A6], [442:Cl, Cl, A6], [443:Cl, Br, A6], [444:Cl, CH₃, A6], [445:Cl, CH₂CH₃, A6], [446:Br, Br, A6], [447:Br, CH₃, A6], [448:Br, CH₂CH₃, A6], [449:CH₃, CH₃, A6], [450:CH₃, CH₂CH₃, A6], [451:CN, H, A6], [452:CN, F, A6], [453:CN, Cl, A6], [454:CN, Br, A6], [455:CN, CH₃, A6], [456:CN, CH₂CH₃, A6], [457:C(=O)OCH₃, H, A6], [458:C(=O)OCH₃, F, A6], [459:C(=O)OCH₃, Cl, A6], [460:C(=O)OCH₃, Br, A6], [461:C(=O)OCH₃, CH₃, A6], [462:C(=O)OCH₃, CH₂CH₃, A6], [463:C(=O)O(CH₃)₃, H, A6], [464:C(=O)O(CH₃)₃, F, A6], [465:C(=O)O(CH₃)₃, Cl, A6], [466:C(=O)O(CH₃)₃, Br, A6], [467:C(=O)O(CH₃)₃, CH₃, A6], [468:C(=O)O(CH₃)₃, CH₂CH₃, A6], [469:C(=O)NH₂, H, A6], [470:C(=O)NH₂, F, A6], [471:C(=O)NH₂, Cl, A6], [472:C(=O)NH₂, Br, A6], [473:C(=O)NH₂, CH₃, A6], [474:C(=O)NH₂, CH₂CH₃, A6], [475:C(=O)NH(CH₃), H, A6], [476:C(=O)NH(CH₃), F, A6], [477:C(=O)NH(CH₃), Cl, A6], [478:C(=O)NH(CH₃), Br, A6], [479:C(=O)NH(CH₃), CH₃, A6], [480:C(=O)NH(CH₃), CH₂CH₃, A6], [481:C(=O)NH(CH₂CH₃), H, A6], [482:C(=O)NH(CH₂CH₃), F, A6], [483:C(=O)NH(CH₂CH₃), Cl, A6], [484:C(=O)NH(CH₂CH₃), Br, A6], [485:C(=O)NH(CH₂CH₃), CH₃, A6], [486:C(=O)NH(CH₂CH₃)CH₂CH₃, A6], [487:C(=O)N(CH₃)₂, H, A6],[488:C(=O)N(CH₃)₂, F, A6],[489:C(=O)N(CH₃)₂, Cl, A6], [490:C(=O)N(CH₃)₂, Br, A6], [491:C(=O)N(CH₃)₂, CH₃, A6], [492:C(=O)N(CH₃)₂, CH₂CH₃, A6], [493:C(=S)OCH₃, H, A6], [494:C(=S)OCH₃, F, A6], [495:C(=S)OCH₃, Cl, A6], [496:C(=S)OCH₃, Br, A6], [497:C(=S)OCH₃, CH₃, A6], [498:C(=S)OCH₃, CH₂CH₃, A6], [499:C(=S)NH₂, H, A6], [500:C(=S)NH₂, F, A6], [501:C(=S)NH₂, Cl, A6], [502:C(=S)NH₂, Br, A6], [503:C(=S)NH₂, CH₃, A6], [504:C(=S)NH₂, CH₂CH₃, A6], [505:C(=S)NH(CH₃), H, A6], [506:C(=S)NH(CH₃), F, A6], [507:C(=S)NH(CH₃), Cl, A6], [508:C(=S)NH(CH₃), Br, A6], [509:C(=S)NH(CH₃), CH₃, A6], [510:C(=S)NH(CH₃), CH₂CH₃, A6], [511:C(=S)N(CH₃)₂, H, A6], [512:C(=S)N(CH₃)₂, F, A6], [513:C(=S)N(CH₃)₂, Cl, A6], [514:C(=S)N(CH₃)₂, Br, A6], [515:C(=S)N(CH₃)₂, CH₃, A6], [516:C(=S)N(CH₃)₂, CH₂CH₃, A6], [517:H, H, A7], [518:H, F, A7], [519:H, Cl, A7], [520:H, Br, A7], [521:H, CH₃, A7], [522:H, CH₂CH₃, A7], [523:F, F, A7], [524:F, Cl, A7], [525:F, Br, A7], [526:F, CH₃, A7], [527:F, CH₂CH₃, A7], [528:Cl, Cl, A7], [529:Cl, Br, A7], [530:Cl, CH₃, A7], [531:Cl, CH₂CH₃, A7], [532:Br, Br, A7], [533:Br, CH₃, A7], [534:Br, CH₂CH₃, A7], [535:CH₃, CH₃, A7], [536:CH₃, CH₂CH₃, A7], [537:CN, H, A7], [538:CN, F, A7], [539:CN, Cl, A7], [540:CN, Br, A7], [541:CN, CH₃, A7], [542:CN, CH₂CH₃, A7], [543:C(=O)OCH₃, H, A7], [544:C(=O)OCH₃, F, A7], [545:C(=O)OCH₃, Cl, A7], [546:C(=O)OCH₃, Br, A7], [547:C(=O)OCH₃, CH₃, A7], [548:C(=O)OCH₃, CH₂CH₃, A7], [549:C(=O)O(CH₃)₃, H, A7], [550:C(=O)O(CH₃)₃, F, A7], [551:C(=O)O(CH₃)₃, Cl, A7], [552:C(=O)O(CH₃)₃, Br, A7], [553:C(=O)O(CH₃)₃, CH₃, A7], [554:C(=O)O(CH₃)₃, CH₂CH₃, A7], [555:C(=O)NH₂, H, A7], [556:C(=O)NH₂, F, A7], [557:C(=O)NH₂, Cl, A7], [558:C(=O)NH₂, Br, A7], [559:C(=O)NH₂, CH₃, A7], [560:C(=O)NH₂, CH₂CH₃, A7], [561:C(=O)NH(CH₃), H, A7], [562:C(=O)NH(CH₃), F, A7], [563:C(=O)NH(CH₃), Cl, A7], [564:C(=O)NH(CH₃), Br, A7], [565:C(=O)NH(CH₃), CH₃, A7], [566:C(=O)NH(CH₃), CH₂CH₃, A7], [567:C(=O) (CH₂CH₃), H, A7], [568:C(=O)NH(CH₂CH₃), F, A7], [569:C(=O)NH(CH₂CH₃), Cl, A7], [570:C(=O)NH(CH₂CH₃), Br, A7], [571:C(=O)NH(CH₂CH₃), CH₃, A7], [572:C(=O)NH(CH₂CH₃), CH₂CH₃, A7], [573:C(=O)N(CH₃)₂, H, A7], [574:C(=O)N(CH₃)₂, F, A7], [575:C(=O)N(CH₃)₂, Cl, A7], [576:C(=O)N(CH₃)₂, Br, A7], [577:C(=O)N(CH₃)₂, CH₃, A7], [578:C(=O)N(CH₃)₂, CH₂CH₃, A7], [579:C(=S)OCH₃, H, A7], [580:C(=S)OCH₃, F, A7], [581:C(=S)OCH₃, Cl, A7], [582:C(=S)OCH₃, Br, A7], [583:C(=S)OCH₃, CH₃, A7], [584:C(=S)OCH₃, CH₂CH₃, A7], [585:C(=S)NH₂, H, A7], [586:C(=S)NH₂, F, A7], [587:C(=S)NH₂, Cl, A7], [588:C(=S)NH₂, Br, A7], [589:C(=S)NH₂, CH₃, A7], [590:C(=S)NH₂, CH₂CH₃, A7], [591:C(=S)NH(CH₃), H, A7], [592:C(=S)NH(CH₃), F, A7], [593:C(=S)NH(CH₃), Cl, A7], [594:C(=S)NH(CH₃), Br, A7], [595:C(=S)NH(CH₃), CH₃, A7], [596:C (=S)NH(CH₃), CH₂CH₃, A7], [597:C(=S)N(CH₃)₂, H, A7], [598:C(=S)N(CH₃)₂, F, A7], [599:C(=S)N(CH₃)₂, Cl, A7], [600:C(=S)N(CH₃)₂, Br, A7], [601:C(=S)N(CH₃)₂, CH₃, A7], [602:C(=S)N(CH₃)₂, CH₂CH₃, A7], [603:H, H, A8], [604:H, F, A8], [605:H, Cl, A8], [606:H, Br, A8], [607:H, CH₃, A8], [608:H, CH₂CH₃, A8], [609:F, F, A8], [610:F, Cl, A8], [611:F, Br, A8], [612:F, CH₃, A8], [613:F, CH₂CH₃, A8], [614:Cl, Cl, A8], [615:Cl, Br, A8], [616:Cl, CH₃, A8], [617:Cl, CH₂CH₃, A8], [618:Br, Br, A8], [619:Br, CH₃, A8], [620:Br, CH₂CH₃, A8], [621:CH₃, CH₃, A8], [622:CH₃, CH₂CH₃, A8], [623:CN, H, A8], [624:CN, F, A8], [625:CN, Cl, A8], [626:CN, Br, A8], [627:CN, CH₃, A8], [628:CN, CH₂CH₃, A8], [629:C(=O)OCH₃, H, A8], [630:C(=O)OCH₃, F, A8], [631:C(=O)OCH₃, Cl, A8], [632:C(=O)OCH₃, Br, A8], [633:C(=O)OCH₃, CH₃, A8], [634:C(=O)OCH₃, CH₂CH₃, A8], [635:C(=O)O(CH₃)₃, H, A8], [636:C(=O)O(CH₃)₃, F, A8], [637:C(=O)O(CH₃)₃, Cl, A8], [638:C(=O)O(CH₃)₃, Br, A8], [639:C(=O)O(CH₃)₃, CH₃, A8], [640:C(=O)O(CH₃)₃, CH₂CH₃, A8], [641:C(=O)NH₂, H, A8], [642:C(=O)NH₂, F, A8], [643:C(=O)NH₂, Cl, A8], [644:C(=O)NH₂, Br, A8], [645:C(=O)NH₂, CH₃, A8], [646:C(=O)NH₂, CH₂CH₃, A8], [647:C(=O)NH(CH₃), H, A8], [648:C(=O)NH(CH₃), F, A8], [649:C(=O)NH(CH₃), Cl, A8], [650:C(=O)NH(CH₃), Br, A8], [651:C(=O)NH(CH₃), CH₃, A8], [652:C(=O)NH(CH₃), CH₂CH₃, A8], [653:C(=O)NH(CH₂CH₃), H, A8], [654:C(=O)NH(CH₂CH₃), F, A8], [655:C(=O)NH(CH₂CH₃), Cl, A8], [656:C(=O)NH(CH₂CH₃), Br, A8], [657:C(=O)NH(CH₂CH₃), CH₃, A8], [658:C(=O)NH(CH₂CH₃), CH₂CH₃, A8], [659:C(=O)N(CH₃)₂, H, A8], [660:C(=O)N(CH₃)₂, F, A8], [661:C(=O)N(CH₃)₂, Cl, A8], [662:C(=O)N(CH₃)₂, Br, A8], [663:C(=O)N(CH₃)₂, CH₃, A8], [664:C(=O)N(CH₃)₂, CH₂CH₃, A8], [665:C(=S)OCH₃, H, A8], [666:C(=S)OCH₃, F, A8], [667:C(=S)OCH₃, Cl, A8], [668:C(=S)OCH₃, Br, A8], [669:C(=S)OCH₃, CH₃, A8], [670:C(=S)OCH₃, CH₂CH₃, A8], [671:C(=S)NH₂, H, A8], [672:C(=S)NH₂, F, A8], [673:C(=S)NH₂, Cl, A8], [674:C(=S)NH₂, Br, A8], [675:C(=S)NH₂, CH₃, A8], [676:C(=S)NH₂, CH₂CH₃, A8], [677:C(=S)NH(CH₃), H, A8], [678:C(=S)NH(CH₃), F, A8], [679:C(=S)NH(CH₃), Cl, A8], [680:C(=S)NH(CH₃), Br, A8], [681:C(=S)NH(CH₃), CH₃, A8], [682:C(=S)NH(CH₃), CH₂CH₃, A8], [683:C(=S)N(CH₃)₂, H, A8], [684:C(=S)N(CH₃)₂, F, A8], [685:C(=S)N(CH₃)₂, Cl, A8], [686:C(=S)N(CH₃)₂, Br, A8], [687:C(=S)N(CH₃)₂, CH₃, A8], [688:C(=S)N(CH₃)₂, CH₂CH₃, A8], [689:H, H, A9], [690:H, F, A9], [691:H, Cl, A9], [692:H, Br, A9], [693:H, CH₃, A9], [694:H, CH₂CH₃, A9], [695:F, F, A9], [696:F, Cl, A9], [697:F, Br, A9], [698:F, CH₃, A9], [699:F, CH₂CH₃, A9], [700:Cl, Cl, A9], [701:Cl, Br, A9], [702:Cl, CH₃, A9], [703:Cl, CH₂CH₃, A9], [704:Br, Br, A9], [705:Br, CH₃, A9], [706:Br, CH₂CH₃, A9], [707:CH₃, CH₃, A9], [708:CH₃, CH₂CH₃, A9], [709:CN, H, A9], [710:CN, F, A9], [711:CN, Cl, A9], [712:CN, Br, A9], [713:CN, CH₃, A9], [714:CN, CH₂CH₃, A9], [715:C(=O)OCH₃, H, A9], [716:C(=O)OCH₃, F, A9], [717:C(=O)OCH₃, Cl, A9], [718:C(=O)OCH₃, Br, A9], [719:C(=O)OCH₃, CH₃, A9], [720:C(=O)OCH₃, CH₂CH₃, A9], [721:C(=O)O(CH₃)₃, H, A9], [722:C(=O)O(CH₃)₃, F, A9], [723:C(=O)O(CH₃)₃, Cl, A9], [724:C(=O)O(CH₃)₃, Br, A9], [725:C(=O)O(CH₃)₃, CH₃, A9], [726:C(=O)O(CH₃)₃, CH₂CH₃, A9], [727:C(=O)NH₂, H, A9], [728:C(=O)NH₂, F, A9], [729:C(=O)NH₂, Cl, A9], [730:C(=O)NH₂, Br, A9], [731:C(=O)NH₂, CH₃, A9], [732:C(=O)NH₂, CH₂CH₃, A9], [733:C(=O)NH(CH₃), H, A9], [734:C(=O)NH(CH₃), F, A9], [735:C(=O)NH(CH₃), Cl, A9], [736:C(=O)NH(CH₃), Br, A9], [737:C(=O)NH(CH₃), CH₃, A9], [738:C(=O)NH(CH₃), CH₂CH₃, A9], [739:C(=O)NH(CH₂CH₃), H, A9], [740:C(=O)NH(CH₂CH₃), F, A9], [741:C(=O)NH(CH₂CH₃), Cl, A9], [742:C(=O)NH(CH₂CH₃), Br, A9], [743:C(=O)NH(CH₂CH₃), CH₃, A9], [744:C(=O)NH(CH₂CH₃), CH₂CH₃, A9], [745:C(=O)N(CH₃)₂, H, A9], [746:C(=O)N(CH₃)₂, F, A9], [747:C(=O)N(CH₃)₂, Cl, A9], [748:C(=O)N(CH₃)₂, Br, A9], [749:C(=O)N(CH₃)₂, CH₃, A9], [750:C(=O)N(CH₃)₂, CH₂CH₃, A9], [751:C(=S)OCH₃, H, A9], [752:C(=S)OCH₃, F, A9], [753:C(=S)OCH₃, Cl, A9], [754:C(=S)OCH₃, Br, A9], [755:C(=S)OCH₃, CH₃, A9], [756:C(=S)OCH₃, CH₂CH₃, A9], [757:C(=S)NH₂, H, A9], [758:C(=S)NH₂, F, A9], [759:C(=S)NH₂, Cl, A9], [760:C(=S)NH₂, Br, A9], [761:C(=S)NH₂, CH₃, A9], [762:C(=S)NH₂, CH₂CH₃, A9], [763:C(=S)NH(CH₃), H, A9], [764:C(=S)NH(CH₃), F, A9], [765:C(=S)NH(CH₃), Cl, A9], [766:C(=S)NH(CH₃), Br, A9], [767:C(=S)NH(CH₃)CH₃, A9], [768:C(=S)NH(CH₃), CH₂CH₃, A9], [769:C(=S)N(CH₃)₂, H, A9], [770:C(=S)N(CH₃)₂, F, A9], [771:C(=S)N(CH₃)₂, Cl, A9], [772:C(=S)N(CH₃)₂, Br, A9], [773:C(=S)N(CH₃)₂, CH₃, A9], [774:C(=S)N(CH₃)₂, CH₂CH₃, A9], [775:H, H, A10], [776:H, F, A10], [777:H, Cl, A10], [778:H, Br, A10], [779:H, CH₃, A10], [780:H, CH₂CH₃, A10], [781:F, F, A10], [782:F, Cl, A10], [783:F, Br, A10], [784:F, CH₃, A10], [785:F, CH₂CH₃, A10], [786:Cl, Cl, A10], [787:Cl, Br, A10], [788:Cl, CH₃, A10], [789:Cl, CH₂CH₃, A10], [790:Br, Br, A10], [791:Br, CH₃, A10], [792:Br, CH₂CH₃, A10], [793:CH₃, CH₃, A10], [794:CH₃, CH₂CH₃, A10], [795:CN, H, A10], [796:CN, F, A10], [797:CN, Cl, A10], [798:CN, Br, A10], [799:CN, CH₃, A10], [800:CN, CH₂CH₃, A10], [801:C(=O)OCH₃, H, A10], [802:C(=O)OCH₃, F, A10], [803:C(=O)OCH₃, Cl, A10], [804:C(=O)OCH₃, Br, A10], [805:C(=O)OCH₃, CH₃, A10], [806:C(=O)OCH₃, CH₂CH₃, A10], [807:C(=O)O(CH₃)₃, H, A10], [808:C(=O)O(CH₃)₃, F, A10], [809:C(=O)O(CH₃)₃, Cl, A10], [810:C(=O)O(CH₃)₃, Br, A10], [811:C(=O)O(CH₃)₃, CH₃, A10], [812:C(=O)O(CH₃)₃, CH₂CH₃, A10], [813:C(=O)NH₂, H, A10], [814:C(=O)NH₂, F, A10], [815:C(=O)NH₂, Cl, A10], [816:C(=O)NH₂, Br, A10], [817:C(=O)NH₂, CH₃, A10], [818:C(=O)NH₂, CH₂CH₃, A10], [819:C(=O)NH(CH₃), H, A10], [820:C(=O)NH(CH₃), F, A10], [821:C(=O)NH(CH₃), Cl, A10], [822:C(=O)NH(CH₃), Br, A10], [823:C(=O)NH(CH₃), CH₃, A10], [824:C(=O)NH(CH₃), CH₂CH₃, A10], [825:C(=O)NH(CH₂CH₃), H, A10], [826:C(=O)NH(CH₂CH₃), F, A10], [827:C(=O)NH(CH₂CH₃), Cl, A10], [828:C(=O)NH(CH₂CH₃), Br, A10], [829:C(=O)NH(CH₂CH₃)CH₃, A10], [830:C(=O)NH(CH₂CH₃), CH₂CH₃, A10], [831:C(=O)N(CH₃)₂, H, A10], [832:C(=O)N(CH₃)₂, F, A10], [833:C(=O)N(CH₃)₂, Cl, A10], [834:C(=O)N(CH₃)₂, Br, A10], [835:C(=O)N(CH₃)₂, CH₃, A10], [836:C(=O)N(CH₃)₂, CH₂CH₃, A10], [837:C(=S)OCH₃, H, A10], [838:C(=S)OCH₃, F, A10], [839:C(=S)OCH₃, Cl, A10], [840:C(=S)OCH₃, Br, A10], [841:C(=S)OCH₃, CH₃, A10], [842:C(=S)OCH₃, CH₂CH₃, A10], [843:C(=S)NH₂, H, A10], [844:C(=S)NH₂, F, A10], [845:C(=S)NH₂, Cl, A10], [846:C(=S)NH₂, Br, A10], [847:C(=S)NH₂, CH₃, A10], [848:C(=S)NH₂, CH₂CH₃, A10], [849:C(=S)NH(CH₃), H, A10], [850:C(=S)NH(CH₃), F, A10], [851:C(=S)NH(CH₃), Cl, A10], [852:C(=S)NH(CH₃), Br A10], [853:C(=S)NH(CH₃), CH₃, A10], [854:C(=S)NH(CH₃), CH₂CH₃, A10], [855:C(=S)N(CH₃)₂, H, A10], [856:C(=S)N(CH₃)₂, F, A10], [857:C(=S)N(CH₃)₂, Cl, A10], [858:C(=S)N(CH₃)₂, Br, A10], [859:C(=S)N(CH₃)₂,

CH₃, A10], [860:C(=S)N(CH₃)₂, CH₂CH₃, A10], [861:H, H, A11], [862:H, F, A11], [863:H, Cl, A11], [864:H, Br, A11], [865:H, CH₃, A11], [866:H, CH₂CH₃, A11], [867:F, F, A11], [868:F, Cl, A11], [869:F, Br, A11], [870:F, CH₃, A11], [871:F, CH₂CH₃, A11], [872:Cl, Cl, A11], [873:Cl, Br, A11], [874:Cl, CH₃, A11], [875:Cl, CH₂CH₃, A11], [876:Br, Br, A11], [877:Br, CH₃, A11], [878:Br, CH₂CH₃, A11], [879:CH₃, CH₃, A11], [880:CH₃, CH₂CH₃, A11], [881:CN, H, A11], [882:CN, F, A11], [883:CN, Cl, A11], [884:CN, Br, A11], [885:CN, CH₃, A11], [886:CN, CH₂CH₃, A11], [887:C(=O)OCH₃, H, A11], [888:C(=O)OCH₃, F, A11], [889:C(=O)OCH₃, Cl, A11], [890:C(=O)OCH₃, Br, A11], [891:C(=O)OCH₃, CH₃, A11], [892:C(=O)OCH₃, CH₂CH₃, A11], [893:C(=O)O(CH₃)₃, H, A11], [894:C(=O)O(CH₃)₃, F, A11], [895:C(=O)O(CH₃)₃, Cl, A11], [896:C(=O)O(CH₃)₃, Br, A11], [897:C(=O)O(CH₃)₃, CH₃, A11], [898:C(=O)O(CH₃)₃, CH₂CH₃, A11], [899:C(=O)NH₂, H, A11], [900:C(=O)NH₂, F, A11], [901:C(=O)NH₂, Cl, A11], [902:C(=O)NH₂, Br, A11], [903:C(=O)NH₂, CH₃, A11], [904:C(=O)NH₂, CH₂CH₃, A11], [905:C(=O)NH(CH₃), H, A11], [906:C(=O)NH(CH₃), F, A11], [907:C(=O)NH(CH₃), Cl, A11], [908:C(=O)NH(CH₃), Br, A11], [909:C(=O)NH(CH₃), CH₃, A11], [910:C(=O)NH(CH₃), CH₂CH₃, A11], [911:C(=O)NH(CH₂CH₃), H, A11], [912:C(=O)NH(CH₂CH₃), F, A11], [913:C(=O)NH(CH₂CH₃), Cl, A11], [914:C(=O)NH(CH₂CH₃), Br, A11], [915:C(=O)NH(CH₂CH₃) CH₃, A11], [916:C(=O)NH(CH₂CH₃), CH₂CH₃, A11], [917:C(=O)N(CH₃)₂, H, A11], [918:C(=O)N(CH₃)₂, F, A11], [919:C(=O)N(CH₃)₂, Cl, A11], [920:C(=O)N(CH₃)₂, Br, A11], [921:C(=O)N(CH₃)₂, CH₃, A11], [922:C(=O)N(CH₃)₂, CH₂CH₃, A11], [923:C(=S)OCH₃, H, A11], [924:C(=S)OCH₃, F, A11], [925:C(=S)OCH₃, Cl, A11], [926:C(=S)OCH₃, Br, A11], [927:C(=S)OCH₃, CH₃, A11], [928:C(=S)OCH₃, CH₂CH₃, A11], [929:C(=S)NH₂, H, A11], [930:C(=S)NH₂, F, A11], [931:C(=S)NH₂, Cl, A11], [932:C(=S)NH₂, Br, A11], [933:C(=S)NH₂, CH₃, A11], [934:C(=S)NH₂, CH₂CH₃, A11], [935:C(=S)NH(CH₃), H, A11], [936:C(=S)NH(CH₃), F, A11], [937:C(=S)NH(CH₃), Cl, A11], [938:C(=S)NH(CH₃), Br, A11], [939:C(=S)NH(CH₃), CH₃, A11], [940:C(=S)NH(CH₃), CH₂CH₃, A11], [941:C(=S)N(CH₃)₂, H, A11], [942:C(=S)N(CH₃)₂, F, A11], [943:C(=S)N(CH₃)₂, Cl, A11], [944:C(=S)N(CH₃)₂, Br, A11], [945:C(=S)N(CH₃)₂, CH₃, A11], [946:C(=S)N(CH₃)₂, CH₂CH₃, A11], [947:H, H, A12], [948:H, F, A12], [949:H, Cl, A12], [950:H, Br, A12], [951:H, CH₃, A12], [952:H, CH₂CH₃, A12], [953:F, F, A12], [954:F, Cl, A12], [955:F, Br, A12], [956:F, CH₃, A12], [957:F, CH₂CH₃, A12], [958:Cl, Cl, A12], [959:Cl, Br, A12], [960:Cl, CH₃, A12], [961:Cl, CH₂CH₃, A12], [962:Br, Br, A12], [963:Br, CH₃, A12], [964:Br, CH₂CH₃, A12], [965:CH₃, CH₃, A12], [966:CH₃, CH₂CH₃, A12], [967:CN, H, A12], [968:CN, F, A12], [969:CN, Cl, A12], [970:CN, Br, A12], [971:CN, CH₃, A12], [972:CN, CH₂CH₃, A12], [973:C(=O)OCH₃, H, A12], [974:C(=O)OCH₃, F, A12], [975:C(=O)OCH₃, Cl, A12], [976:C(=O)OCH₃, Br, A12], [977:C(=O)OCH₃, CH₃, A12], [978:C(=O)OCH₃, CH₂CH₃, A12], [979:C(=O)O(CH₃)₃, H, A12], [980:C(=O)O(CH₃)₃, F, A12], [981:C(=O)O(CH₃)₃, Cl, A12], [982:C(=O)O(CH₃)₃, Br, A12], [983:C(=O)O(CH₃)₃, CH₃, A12], [984:C(=O)O(CH₃)₃ CH₂CH₃, A12], [985:C(=O)NH₂, H, A12], [986:C(=O)NH₂, F, A12], [987:C(=O)NH₂, Cl, A12], [988:C(=O)NH₂, Br, A12], [989:C(=O)NH₂, CH₃, A12], [990:C(=O)NH₂, CH₂CH₃, A12], [991:C(=O)NH(CH₃), H, A12], [992:C(=O)NH(CH₃), F, A12], [993:C(=O)NH(CH₃), Cl, A12], [994:C(=O)NH(CH₃), Br, A12], [995:C(=O)NH(CH₃), CH₃, A12], [996:C(=O)NH(CH₃), CH₂CH₃, A12], [997:C(=O)NH(CH₂CH₃), H, A12], [998:C(=O)NH(CH₂CH₃), F, A12], [999:C(=O)NH(CH₂CH₃), Cl, A12], [1000:C(=O)NH(CH₂CH₃), Br, A12], [1001:C(=O)NH(CH₂CH₃), CH₃, A12], [1002:C(=O)NH(CH₂CH₃), CH₂CH₃, A12], [1003:C(=O)N(CH₃)₂, H, A12], [1004:C(=O)N(CH₃)₂, F, A12], [1005:C(=O)N(CH₃)₂, Cl, A12], [1006:C(=O)N(CH₃)₂, Br, A12], [1007:C(=O)N(CH₃)₂, CH₃, A12], [1008:C(=O)N(CH₃)₂, CH₂CH₃, A12], [1009:C(=S)OCH₃, H, A12], [1010:C(=S)OCH₃, F, A12], [1011:C(=S)OCH₃, Cl, A12], [1012:C(=S)OCH₃, Br, A12], [1013:C(=S)OCH₃, CH₃, A12], [1014:C(=S)OCH₃, CH₂CH₃, A12], [1015:C(=S)NH₂, H, A12], [1016:C(=S)NH₂, F, A12], [1017:C(=S)NH₂, Cl, A12], [1018:C(=S)NH₂, Br, A12], [1019:C(=S)NH₂, CH₃, A12], [1020:C(=S)NH₂, CH₂CH₃, A12], [1021:C(=S)NH(CH₃), H, A12], [1022:C(=S)NH(CH₃), F, A12], [1023:C(=S)NH(CH₃), Cl, A12], [1024:C(=S)NH(CH₃), Br, A12], [1025:C(=S)NH(CH₃), CH₃, A12], [1026:C(=S)NH(CH₃), CH₂CH₃, A12], [1027:C(=S)N(CH₃)₂, H, A12], [1028:C(=S)N(CH₃)₂, F, A12], [1029:C(=S)N(CH₃)₂, Cl, A12], [1030:C(=S)N(CH₃)₂, Br, A12], [1031:C(=S)N(CH₃)₂, CH₃, A12], [1032:C(=S)N(CH₃)₂, CH₂CH₃, A12], [1033:H, H, A13], [1034:H, F, A13], [1035:H, Cl, A13], [1036:H, Br, A13], [1037:H, CH₃, A13], [1038:H, CH₂CH₃, A13], [1039:F, F, A13], [1040:F, Cl, A13], [1041:F, Br, A13], [1042:F, CH₃, A13], [1043:F, CH₂CH₃, A13], [1044:Cl, Cl, A13], [1045:Cl, Br, A13], [1046:Cl, CH₃, A13], [1047:Cl, CH₂CH₃, A13], [1048:Br, Br, A13], [1049:Br, CH₃, A13], [1050:Br, CH₂CH₃, A13], [1051:CH₃, CH₃, A13], [1052:CH₃, CH₂CH₃, A13], [1053:CN, H, A13], [1054:CN, F, A13], [1055:CN, Cl, A13], [1056:CN, Br, A13], [1057:CN, CH₃, A13], [1058:CN, CH₂CH₃, A13], [1059:C(=O)OCH₃, H, A13], [1060:C(=O)OCH₃, F, A13], [1061:C(=O)OCH₃, Cl, A13], [1062:C(=O)OCH₃, Br, A13], [1063:C(=O)OCH₃, CH₃, A13], [1064:C(=O)OCH₃, CH₂CH₃, A13], [1065:C(=O)O(CH₃)₃, H, A13], [1066:C(=O)O(CH₃)₃, F, A13], [1067:C(=O)O(CH₃)₃, Cl, A13], [1068:C(=O)O(CH₃)₃, Br, A13], [1069:C(=O)O(CH₃)₃, CH₃, A13], [1070:C(=O)O(CH₃)₃, CH₂CH₃, A13], [1071:C(=O)NH₂, H, A13], [1072:C(=O)NH₂, F, A13], [1073:C(=O)NH₂, Cl, A13], [1074:C(=O)NH₂, Br, A13], [1075:C(=O)NH₂, CH₃, A13], [1076:C(=O)NH₂, CH₂CH₃, A13], [1077:C(=O)NH(CH₃), H, A13], [1078:C(=O)NH(CH₃), F, A13], [1079:C(=O)NH(CH₃), Cl, A13], [1080:C(=O)NH(CH₃), Br, A13], [1081:C(=O)NH(CH₃), CH₃, A13], [1082:C(=O)NH(CH₃), CH₂CH₃, A13], [1083:C(=O)NH(CH₂CH₃), H, A13], [1084:C(=O)NH(CH₂CH₃), F, A13], [1085:C(=O)NH(CH₂CH₃), Cl, A13], [1086:C(=O)NH(CH₂CH₃), Br, A13], [1087:C(=O)NH(CH₂CH₃), CH₃, A13], [1088:C(=O)NH(CH₂CH₃), CH₂CH₃, A13], [1089:C(=O)N(CH₃)₂, H, A13], [1090:C(=O)N(CH₃)₂, F, A13], [1091:C(=O)N(CH₃)₂, Cl, A13], [1092:C(=O)N(CH₃)₂, Br, A13], [1093:C(=O)N(CH₃)₂, CH₃, A13], [1094:C(=O)N(CH₃)₂, CH₂CH₃, A13], [1095:C(=S)OCH₃, H, A13], [1096:C(=S)OCH₃, F, A13], [1097:C(=S)OCH₃, Cl, A13], [1098:C(=S)OCH₃, Br, A13], [1099:C(=S)OCH₃, CH₃, A13], [1100:C(=S)OCH₃, CH₂CH₃, A13], [1101:C(=S)NH₂, H, A13], [1102:C(=S)NH₂, F, A13], [1103:C(=S)NH₂, Cl, A13], [1104:C(=S)NH₂, Br, A13], [1105:C(=S)NH₂, CH₃, A13], [1106:C(=S)NH₂, CH₂CH₃, A13], [1107:C(=S)NH(CH₃), H, A13], [1108:C(=S)NH(CH₃), F, A13], [1109:C(=S)NH(CH₃), Cl, A13], [1110:C(=S)NH(CH₃), Br, A13], [1111:C(=S)NH(CH₃), CH₃,

A13], [1112:C(=S)NH(CH₃), CH₂CH₃, A13], [1113:C(=S)N(CH₃)₂, H, A13], [1114:C(=S)N(CH₃)₂, F, A13], [1115:C(=S)N(CH₃)₂, Cl, A13], [1116:C(=S)N(CH₃)₂, Br, A13], [1117:C(=S)N(CH₃)₂, CH₃, A13], [1118:C(=S)N(CH₃)₂, CH₂CH₃, A13], [1119:H, H, A14], [1120: H, F, A14], [1121:H, Cl, A14], [1122:H, Br, A14], [1123:H, CH₃, A14], [1124:H, CH₂CH₃, A14], [1125:F, F, A14], [1126:F, Cl, A14], [1127:F, Br, A14], [1128:F, CH₃, A14], [1129:F, CH₂CH₃, A14], [1130:Cl, Cl, A14], [1131:Cl, Br, A14], [1132:Cl, CH₃, A14], [1133:Cl, CH₂CH₃, A14], [1134:Br, Br, A14], [1135:Br, CH₃, A14], [1136:Br, CH₂CH₃, A14], [1137:CH₃, CH₃, A14], [1138:CH₃, CH₂CH₃, A14], [1139:CN, H, A14], [1140:CN, F, A14], [1141:CN, Cl, A14], [1142:CN, Br, A14], [1143:CN, CH₃, A14], [1144:CN, CH₂CH₃, A14], [1145:C(=O)OCH₃, H, A14], [1146:C(=O)OCH₃, F, A14], [1147:C(=O) OCH₃, Cl, A14], [1148:C(=O)OCH₃, Br, A14], [1149:C(=O)OCH₃, CH₃, A14], [1150:C(=O)OCH₃, CH₂CH₃, A14], [1151:C(=O)O(CH₃)₃, H, A14], [1152:C(=O)O(CH₃)₃, F, A14], [1153:C(=O)O(CH₃)₃, Cl, A14], [1154:C(=O)O(CH₃)₃, Br, A14], [1155:C(=O)O(CH₃)₃, CH₃, A14], [1156:C(=O)O(CH₃)₃, CH₂CH₃, A14], [1157:C(=O)NH₂, H, A14], [1158:C(=O)NH₂, F, A14], [1159:C(=O)NH₂, Cl, A14], [1160:C(=O)NH₂, Br, A14], [1161:C(=O)NH₂, CH₃, A14], [1162:C(=O)NH₂, CH₂CH₃, A14], [1163:C(=O)NH(CH₃), H, A14], [1164:C(=O)NH(CH₃), F, A14], [1165:C(=O)NH(CH₃), Cl, A14], [1166:C(=O)NH(CH₃), Br, A14], [1167:C(=O)NH(CH₃), CH₃, A14], [1168:C(=O)NH(CH₃), CH₂CH₃, A14], [1169:C(=O)NH(CH₂CH₃), H, A14], [1170:C(=O)NH(CH₂CH₃), F, A14], [1171:C(=O)NH(CH₂CH₃), Cl, A14], [1172:C(=O)NH(CH₂CH₃), Br, A14], [1173:C(=O)NH(CH₂CH₃), CH₃, A14], [1174:C(=O)NH(CH₂CH₃), CH₂CH₃, A14], [1175:C(=O)N(CH₃)₂, H, A14], [1176:C(=O)N(CH₃)₂, F, A14], [1177:C(=O)N(CH₃)₂, Cl, A14], [1178:C(=O)N(CH₃)₂, Br, A14], [1179:C(=O)N(CH₃)₂, CH₃, A14], [1180:C(=O)N(CH₃)₂, CH₂CH₃, A14], [1181:C(=S)OCH₃, H, A14], [1182:C(=S)OCH₃, F, A14], [1183:C(=S)OCH₃, Cl, A14], [1184:C(=S)OCH₃, Br, A14], [1185:C(=S)OCH₃, CH₃, A14], [1186:C(=S)OCH₃, CH₂CH₃, A14], [1187:C(=S)NH₂, H, A14], [1188:C(=S)NH₂, F, A14], [1189:C(=S)NH₂, Cl, A14], [1190:C(=S)NH₂, Br, A14], [1191:C(=S)NH₂, CH₃, A14], [1192:C(=S)NH₂, CH₂CH₃, A14], [1193:C(=S)NH(CH₃), H, A14], [1194:C(=S)NH(CH₃), F, A14], [1195:C(=S)NH(CH₃), Cl, A14], [1196:C(=S)NH(CH₃), Br, A14], [1197:C(=S)NH(CH₃), CH₃, A14], [1198:C(=S)NH(CH₃), CH₂CH₃, A14], [1199:C(=S)N(CH₃)₂, H, A14], [1200:C(=S)N(CH₃)₂, F, A14], [1201:C(=S)N(CH₃)₂, Cl, A14], [1202:C(=S)N(CH₃)₂, Br, A14], [1203:C(=S)N(CH₃)₂, CH₃, A14], [1204:C(=S)N(CH₃)₂, CH₂CH₃, A14], [1205:H, H, A15], [1206: H, F, A15], [1207:H, Cl, A15], [1208:H, Br, A15], [1209:H, CH₃, A15], [1210:H, CH₂CH₃, A15], [1211:F, F, A15], [1212:F, Cl, A15], [1213:F, Br, A15], [1214:F, CH₃, A15], [1215:F, CH₂CH₃, A15], [1216:Cl, Cl, A15], [1217:Cl, Br, A15], [1218:Cl, CH₃, A15], [1219:Cl, CH₂CH₃, A15], [1220:Br, Br, A15], [1221:Br, CH₃, A15], [1222:Br, CH₂CH₃, A15], [1223:CH₃, CH₃, A15], [1224:CH₃, CH₂CH₃, A15], [1225:CN, H, A15], [1226:CN, F, A15], [1227:CN, Cl, A15], [1228:CN, Br, A15], [1229:CN, CH₃, A15], [1230:CN, CH₂CH₃, A15], [1231:C(=O)OCH₃, H, A15], [1232:C(=O)OCH₃, F, A15], [1233:C(=O)OCH₃, Cl, A15], [1234:C(=O)OCH₃, Br, A15], [1235:C(=O)OCH₃, CH₃, A15], [1236:C(=O)OCH₃, CH₂CH₃, A15], [1237:C(=O)O(CH₃)₃, H, A15], [1238:C(=O)O(CH₃)₃, F, A15], [1239:C(=O)O(CH₃)₃, Cl, A15], [1240:C(=O)O(CH₃)₃, Br, A15], [1241:C(=O)O(CH₃)₃, CH₃, A15], [1242:C(=O)O(CH₃)₃, CH₂CH₃, A15], [1243:C(=O)NH₂, H, A15], [1244:C(=O)NH₂, F, A15], [1245:C(=O)NH₂, Cl, A15], [1246:C(=O)NH₂, Br, A15], [1247:C(=O)NH₂, CH₃, A15], [1248:C(=O)NH₂, CH₂CH₃, A15], [1249:C(=O)NH(CH₃), H, A15], [1250:C(=O)NH(CH₃), F, A15], [1251:C(=O)NH(CH₃), Cl, A15], [1252:C(=O)NH(CH₃), Br, A15], [1253:C(=O)NH(CH₃), CH₃, A15], [1254:C(=O)NH(CH₃), CH₂CH₃, A15], [1255:C(=O)NH(CH₂CH₃), H, A15], [1256:C(=O)NH(CH₂CH₃), F, A15], [1257:C(=O)NH(CH₂CH₃), Cl, A15], [1258:C(=O)NH(CH₂CH₃), Br, A15], [1259:C(=O)NH(CH₂CH₃), CH₃, A15], [1260:C(=O)NH(CH₂CH₃), CH₂CH₃, A15], [1261:C(=O)N(CH₃)₂, H, A15], [1262:C(=O)N(CH₃)₂, F, A15], [1263:C(=O)N(CH₃)₂, Cl, A15], [1264:C(=O)N(CH₃)₂, Br, A15], [1265:C(=O)N(CH₃)₂, CH₃, A15], [1266:C(=O)N(CH₃)₂, CH₂CH₃, A15], [1267:C(=S)OCH₃, H, A15], [1268:C(=S)OCH₃, F, A15], [1269:C(=S)OCH₃, Cl, A15], [1270:C(=S)OCH₃, Br, A15], [1271:C(=S)OCH₃, CH₃, A15], [1272:C(=S)OCH₃, CH₂CH₃, A15], [1273:C(=S)NH₂, H, A15], [1274:C(=S)NH₂, F, A15], [1275:C(=S)NH₂, Cl, A15], [1276:C(=S)NH₂, Br, A15], [1277:C(=S)NH₂, CH₃, A15], [1278:C(=S)NH₂, CH₂CH₃, A15], [1279:C(=S)NH(CH₃), H, A15], [1280:C(=S)NH(CH₃), F, A15], [1281:C(=S)NH(CH₃), Cl, A15], [1282:C(=S)NH(CH₃), Br, A15], [1283:C(=S)NH(CH₃), CH₃, A15], [1284:C(=S)NH(CH₃), CH₂CH₃, A15], [1285:C(=S)N(CH₃)₂, H, A15], [1286:C(=S)N(CH₃)₂, F, A15], [1287:C(=S)N(CH₃)₂, Cl, A15], [1288:C(=S)N(CH₃)₂, Br, A15], [1289:C(=S)N(CH₃)₂, CH₃, A15], [1290:C(=S)N(CH₃)₂, CH₂CH₃, A15], [1291:H, H, A16], [1292: H, F, A16], [1293:H, Cl, A16], [1294:H, Br, A16], [1295:H, CH₃, A16], [1296:H, CH₂CH₃, A16], [1297:F, F, A16], [1298:F, Cl, A16], [1299:F, Br, A16], [1300:F, CH₃, A16], [1301:F, CH₂CH₃, A16], [1302:Cl, Cl, A16], [1303:Cl, Br, A16], [1304:Cl, CH₃, A16], [1305:Cl, CH₂CH₃, A16], [1306:Br, Br, A16], [1307:Br, CH₃, A16], [1308:Br, CH₂CH₃, A16], [1309:CH₃, CH₃, A16], [1310:CH₃, CH₂CH₃, A16], [1311:CN, H, A16], [1312:CN, F, A16], [1313:CN, Cl, A16], [1314:CN, Br, A16], [1315:CN, CH₃, A16], [1316:CN, CH₂CH₃, A16], [1317:C(=O)OCH₃, H, A16], [1318:C(=O)OCH₃, F, A16], [1319:C(=O)OCH₃, Cl, A16], [1320:C(=O)OCH₃, Br, A16], [1321:C(=O)OCH₃, CH₃, A16], [1322:C(=O)OCH₃, CH₂CH₃, A16], [1323:C(=O)O(CH₃)₃, H, A16], [1324:C(=O)O(CH₃)₃, F, A16], [1325:C(=O)O(CH₃)₃, Cl, A16], [1326:C(=O)O(CH₃)₃, Br, A16], [1327:C(=O)O(CH₃)₃, CH₃, A16], [1328:C(=O)O(CH₃)₃, CH₂CH₃, A16], [1329:C(=O)NH₂, H, A16], [1330:C(=O)NH₂, F, A16], [1331:C(=O)NH₂, Cl, A16], [1332:C(=O)NH₂, Br, A16], [1333:C(=O)NH₂, CH₃, A16], [1334:C(=O)NH₂, CH₂CH₃, A16], [1335:C(=O)NH(CH₃), H, A16], [1336:C(=O)NH(CH₃), F, A16], [1337:C(=O)NH(CH₃), Cl, A16], [1338:C(=O)NH(CH₃), Br, A16], [1339:C(=O)NH(CH₃), CH₃, A16], [1340:C(=O)NH(CH₃), CH₂CH₃, A16], [1341:C(=O)NH(CH₂CH₃), H, A16], [1342:C(=O)NH(CH₂CH₃), F, A16], [1343:C(=O)NH(CH₂CH₃), Cl, A16], [1344:C(=O)NH(CH₂CH₃), Br, A16], [1345:C(=O)NH(CH₂CH₃), CH₃, A16], [1346:C(=O)NH(CH₂CH₃), CH₂CH₃, A16], [1347:C(=O)N(CH₃)₂, H, A16], [1348:C(=O)N(CH₃)₂, F, A16], [1349:C(=O)N(CH₃)₂, Cl, A16], [1350:C(=O)N(CH₃)₂, Br, A16], [1351:C(=O)N(CH₃)₂, CH₃, A16], [1352:C(=O)N(CH₃)₂, CH₂CH₃, A16], [1353:C(=S)OCH₃, H, A16], [1354:C(=S)OCH₃, F, A16], [1355:C(=S)OCH₃, Cl, A16], [1356:C(=S)OCH₃, Br, A16], [1357:C(=S)OCH₃,

CH₃, A16], [1358:C(=S)OCH₃, CH₂CH₃, A16], [1359:C(=S)NH₂, H, A16], [1360:C(=S)NH₂, F, A16], [1361:C(=S)NH₂, Cl, A16], [1362:C(=S)NH₂, Br, A16], [1363:C(=S)NH₂, CH₃, A16], [1364:C(=S)NH₂, CH₂CH₃, A16], [1365:C(=S)NH(CH₃), H, A16], [1366:C(=S)NH(CH₃), F, A16], [1367:C(=S)NH(CH₃), Cl, A16], [1368:C(=S)NH(CH₃), Br, A16], [1369:C(=S)NH(CH₃), CH₃, A16], [1370:C(=S)NH(CH₃), CH₂CH₃, A16], [1371:C(=S)N(CH₃)₂, H, A16], [1372:C(=S)N(CH₃)₂, F, A16], [1373:C(=S)N(CH₃)₂, Cl, A16], [1374:C(=S)N(CH₃)₂, Br, A16], [1375:C(=S)N(CH₃)₂, CH₃, A16], [1376:C(=S)N(CH₃)₂, CH₂CH₃, A16], [1377:H, H, A17], [1378:H, F, A17], [1379:H, Cl, A17], [1380:H, Br, A17], [1381:H, CH₃, A17], [1382:H, CH₂CH₃, A17], [1383:F, F, A17], [1384:F, Cl, A17], [1385:F, Br, A17], [1386:F, CH₃, A17], [1387:F, CH₂CH₃, A17], [1388:Cl, Cl, A17], [1389:Cl, Br, A17], [1390:Cl, CH₃, A17], [1391:Cl, CH₂CH₃, A17], [1392:Br, Br, A17], [1393:Br, CH₃, A17], [1394:Br, CH₂CH₃, A17], [1395:CH₃, CH₃, A17], [1396:CH₃, CH₂CH₃, A17], [1397:CN, H, A17], [1398:CN, F, A17], [1399:CN, Cl, A17], [1400:CN, Br, A17], [1401:CN, CH₃, A17], [1402:CN, CH₂CH₃, A17], [1403:C(=O)OCH₃, H, A17], [1404:C(=O)OCH₃, F, A17], [1405:C(=O)OCH₃, Cl, A17], [1406:C(=O)OCH₃, Br, A17], [1407:C(=O)OCH₃, CH₃, A17], [1408:C(=O)OCH₃, CH₂CH₃, A17], [1409:C(=O)O(CH₃)₃, H, A17], [1410:C(=O)O(CH₃)₃, F, A17], [1411:C(=O)O(CH₃)₃, Cl, A17], [1412:C(=O)O(CH₃)₃, Br, A17], [1413:C(=O)O(CH₃)₃, CH₃, A17], [1414:C(=O)O(CH₃)₃, CH₂CH₃, A17], [1415:C(=O)NH₂, H, A17], [1416:C(=O)NH₂, F, A17], [1417:C(=O)NH₂, Cl, A17], [1418:C(=O)NH₂, Br, A17], [1419:C(=O)NH₂, CH₃, A17], [1420:C(=O)NH₂, CH₂CH₃, A17], [1421:C(=O)NH(CH₃), H, A17], [1422:C(=O)NH(CH₃), F, A17], [1423:C(=O)NH(CH₃), Cl, A17], [1424:C(=O)NH(CH₃), Br, A17], [1425:C(=O)NH(CH₃), CH₃, A17], [1426:C(=O)NH(CH₃), CH₂CH₃, A17], [1427:C(=O)NH(CH₂CH₃), H, A17], [1428:C(=O)NH(CH₂CH₃), F, A17], [1429:C(=O)NH(CH₂CH₃), Cl, A17], [1430:C(=O)NH(CH₂CH₃), Br, A17], [1431:C(=O)NH(CH₂CH₃), CH₃, A17], [1432:C(=O)NH(CH₂CH₃), CH₂CH₃, A17], [1433:C(=O)N(CH₃)₂, H, A17], [1434:C(=O)N(CH₃)₂, F, A17], [1435:C(=O)N(CH₃)₂, Cl, A17], [1436:C(=O)N(CH₃)₂, Br, A17], [1437:C(=O)N(CH₃)₂, CH₃, A17], [1438:C(=O)N(CH₃)₂, CH₂CH₃, A17], [1439:C(=S)OCH₃, H, A17], [1440:C(=S)OCH₃, F, A17], [1441:C(=S)OCH₃, Cl, A17], [1442:C(=S)OCH₃, Br, A17], [1443:C(=S)OCH₃, CH₃, A17], [1444:C(=S)OCH₃, CH₂CH₃, A17], [1445:C(=S)NH₂, H, A17], [1446:C(=S)NH₂, F, A17], [1447:C(=S)NH₂, Cl, A17], [1448:C(=S)NH₂, Br, A17], [1449:C(=S)NH₂, CH₃, A17], [1450:C(=S)NH₂, CH₂CH₃, A17], [1451:C(=S)NH(CH₃), H, A17], [1452:C(=S)NH(CH₃), F, A17], [1453:C(=S)NH(CH₃), Cl, A17], [1454:C(=S)NH(CH₃), Br, A17], [1455:C(=S)NH(CH₃), CH₃, A17], [1456:C(=S)NH(CH₃), CH₂CH₃, A17], [1457:C(=S)N(CH₃)₂, H, A17], [1458:C(=S)N(CH₃)₂, F, A17], [1459:C(=S)N(CH₃)₂, Cl, A17], [1460:C(=S)N(CH₃)₂, Br, A17], [1461:C(=S)N(CH₃)₂, CH₃, A17], [1462:C(=S)N(CH₃)₂, CH₂CH₃, A17], [1463:H, H, A18], [1464:H, F, A18], [1465:H, Cl, A18], [1466:H, Br, A18], [1467:H, CH₃, A18], [1468:H, CH₂CH₃, A18], [1469:F, F, A18], [1470:F, Cl, A18], [1471:F, Br, A18], [1472:F, CH₃, A18], [1473:F, CH₂CH₃, A18], [1474:Cl, Cl, A18], [1475:Cl, Br, A18], [1476:Cl, CH₃, A18], [1477:Cl, CH₂CH₃, A18], [1478:Br, Br, A18], [1479:Br, CH₃, A18], [1480:Br, CH₂CH₃, A18], [1481:CH₃, CH₃, A18], [1482:CH₃, CH₂CH₃, A18], [1483:CN, H, A18], [1484:CN, F, A18], [1485:CN, Cl, A18], [1486:CN, Br, A18], [1487:CN, CH₃, A18], [1488:CN, CH₂CH₃, A18], [1489:C(=O)OCH₃, H, A18], [1490:C(=O)OCH₃, F, A18], [1491:C(=O)OCH₃, Cl, A18], [1492:C(=O)OCH₃, Br, A18], [1493:C(=O)OCH₃, CH₃, A18], [1494:C(=O)OCH₃, CH₂CH₃, A18], [1495:C(=O)O(CH₃)₃, H, A18], [1496:C(=O)O(CH₃)₃, F, A18], [1497:C(=O)O(CH₃)₃, Cl, A18], [1498:C(=O)O(CH₃)₃, Br, A18], [1499:C(=O)O(CH₃)₃, CH₃, A18], [1500:C(=O)O(CH₃)₃, CH₂CH₃, A18], [1501:C(=O)NH₂, H, A18], [1502:C(=O)NH₂, F, A18], [1503:C(=O)NH₂, Cl, A18], [1504:C(=O)NH₂, Br, A18], [1505:C(=O)NH₂, CH₃, A18], [1506:C(=O)NH₂, CH₂CH₃, A18], [1507:C(=O)NH(CH₃), H, A18], [1508:C(=O)NH(CH₃), F, A18], [1509:C(=O)NH(CH₃), Cl, A18], [1510:C(=O)NH(CH₃), Br, A18], [1511:C(=O)NH(CH₃)CH₃, A18], [1512:C(=O)NH(CH₃), CH₂CH₃, A18], [1513:C(=O)NH(CH₂CH₃), H, A18], [1514:C(=O)NH(CH₂CH₃), F, A18], [1515:C(=O)NH(CH₂CH₃), Cl, A18], [1516:C(=O)NH(CH₂CH₃), Br, A18], [1517:C(=O)NH(CH₂CH₃), CH₃, A18], [1518:C(=O)NH(CH₂CH₃), CH₂CH₃, A18], [1519:C(=O)N(CH₃)₂, H, A18], [1520:C(=O)N(CH₃)₂, F, A18], [1521:C(=O)N(CH₃)₂, Cl, A18], [1522:C(=O)N(CH₃)₂, Br, A18], [1523:C(=O)N(CH₃)₂, CH₃, A18], [1524:C(=O)N(CH₃)₂, CH₂CH₃, A18], [1525:C(=S)OCH₃, H, A18], [1526:C(=S)OCH₃, F, A18], [1527:C(=S)OCH₃, Cl, A18], [1528:C(=S)OCH₃, Br, A18], [1529:C(=S)OCH₃, CH₃, A18], [1530:C(=S)OCH₃, CH₂CH₃, A18], [1531:C(=S)NH₂, H, A18], [1532:C(=S)NH₂, F, A18], [1533:C(=S)NH₂, Cl, A18], [1534:C(=S)NH₂, Br, A18], [1535:C(=S)NH₂, CH₃, A18], [1536:C(=S)NH₂, CH₂CH₃, A18], [1537:C(=S)NH(CH₃), H, A18], [1538:C(=S)NH(CH₃), F, A18], [1539:C(=S)NH(CH₃), Cl, A18], [1540:C(=S)NH(CH₃), Br, A18], [1541:C(=S)NH(CH₃), CH₃, A18], [1542:C(=S)NH(CH₃), CH₂CH₃, A18], [1543:C(=S)N(CH₃)₂, H, A18], [1544:C(=S)N(CH₃)₂, F, A18], [1545:C(=S)N(CH₃)₂, Cl, A18], [1546:C(=S)N(CH₃)₂, Br, A18], [1547:C(=S)N(CH₃)₂, CH₃, A18], [1548:C(=S)N(CH₃)₂, CH₂CH₃, A18], [1549:H, H, A19], [1550:H, F, A19], [1551:H, Cl, A19], [1552:H, Br, A19], [1553:CH₃, A19], [1554:CH₂CH₃, A19], [1555:F, A19], [1556:F, Cl, A19], [1557:F, Br, A19], [1558:F, CH₃, A19], [1559:F, CH₂CH₃, A19], [1560:Cl, Cl, A19], [1561:Cl, Br, A19], [1562:Cl, CH₃, A19], [1563:Cl, CH₂CH₃, A19], [1564:Br, Br, A19], [1565:Br, CH₃, A19], [1566:Br, CH₂CH₃, A19], [1567:CH₃, CH₃, A19], [1568:CH₃, CH₂CH₃, A19], [1569:CN, H, A19], [1570:CN, F, A19], [1571:CN, Cl, A19], [1572:CN, Br, A19], [1573:CN, CH₃, A19], [1574:CN, CH₂CH₃, A19], [1575:C(=O)OCH₃, H, A19], [1576:C(=O)OCH₃, F, A19], [1577:C(=O)OCH₃, Cl, A19], [1578:C(=O)OCH₃, Br, A19], [1579:C(=O)OCH₃, CH₃, A19], [1580:C(=O)OCH₃, CH₂CH₃, A19], [1581:C(=O)O(CH₃)₃, H, A19], [1582:C(=O)O(CH₃)₃, F, A19], [1583:C(=O)O(CH₃)₃, Cl, A19], [1584:C(=O)O(CH₃)₃, Br, A19], [1585:C(=O)O(CH₃)₃, CH₃, A19], [1586:C(=O)O(CH₃)₃, CH₂CH₃, A19], [1587:C(=O)NH₂, H, A19], [1588:C(=O)NH₂, F, A19], [1589:C(=O)NH₂, Cl, A19], [1590:C(=O)NH₂, Br, A19], [1591:C(=O)NH₂, CH₃, A19], [1592:C(=O)NH₂, CH₂CH₃, A19], [1593:C(=O)NH(CH₃), H, A19], [1594:C(=O)NH(CH₃), F, A19], [1595:C(=O)NH(CH₃), Cl, A19], [1596:C(=O)NH(CH₃), Br, A19], [1597:C(=O)NH(CH₃), CH₃, A19], [1598:C(=O)NH(CH₃), CH₂CH₃, A19], [1599:C(=O)NH(CH₂CH₃), H, A19], [1600:C(=O)NH(CH₂CH₃), F, A19], [1601:C(=O)NH(CH₂CH₃), Cl, A19], [1602:C(=O)NH(CH₂CH₃), Br, A19], [1603:C(=O)NH(CH₂CH₃), CH₃, A19], [1604:C(=O)NH(CH₂CH₃),

CH₂CH₃, A19], [1605:C(=O)N(CH₃)₂, H, A19], [1606:C(=O)N(CH₃)₂, F, A19], [1607:C(=O)N(CH₃)₂, Cl, A19], [1608:C(=O)N(CH₃)₂, Br, A19], [1609:C(=O)N(CH₃)₂, CH₃, A19], [1610:C(=O)N(CH₃)₂, CH₂CH₃, A19], [1611:C(=S)OCH₃, H, A19], [1612:C(=S)OCH₃, F, A19], [1613:C(=S)OCH₃, Cl, A19], [1614:C(=S)OCH₃, Br, A19], [1615:C(=S)OCH₃, CH₃, A19], [1616:C(=S)OCH₃, CH₂CH₃, A19], [1617:C(=S)NH₂, H, A19], [1618:C(=S)NH₂, F, A19], [1619:C(=S)NH₂, Cl, A19], [1620:C(=S)NH₂, Br, A19], [1621:C(=S)NH₂, CH₃, A19], [1622:C(=S)NH₂, CH₂CH₃, A19], [1623:C(=S)NH(CH₃), H, A19], [1624:C(=S)NH(CH₃), F, A19], [1625:C(=S)NH(CH₃), Cl, A19], [1626:C(=S)NH(CH₃), Br, A19], [1627:C(=S)NH(CH₃), CH₃, A19], [1628:C(=S)NH(CH₃), CH₂CH₃, A19], [1629:C(=S)N(CH₃)₂, H, A19], [1630:C(=S)N(CH₃)₂, F, A19], [1631:C(=S)N(CH₃)₂, Cl, A19], [1632:C(=S)N(CH₃)₂, Br, A19], [1633:C(=S)N(CH₃)₂, CH₃, A19], [1634:C(=S)N(CH₃)₂, CH₂CH₃, A19], [1635:H, H, A20], [1636:H, F, A20], [1637:H, Cl, A20], [1638:H, Br, A20], [1639:H, CH₃, A20], [1640:H, CH₂CH₃, A20], [1641:F, F, A20], [1642:F, Cl, A20], [1643:F, Br, A20], [1644:F, CH₃, A20], [1645:F, CH₂CH₃, A20], [1646:Cl, Cl, A20], [1647:Cl, Br, A20], [1648:Cl, CH₃, A20], [1649:Cl, CH₂CH₃, A20], [1650:Br, Br, A20], [1651:Br, CH₃, A20], [1652:Br, CH₂CH₃, A20], [1653:CH₃, CH₃, A20], [1654:CH₃, CH₂CH₃, A20], [1655:CN, H, A20], [1656:CN, F, A20], [1657:CN, Cl, A20], [1658:CN, Br, A20], [1659:CN, CH₃, A20], [1660:CN, CH₂CH₃, A20], [1661:C(=O)OCH₃, H, A20], [1662:C(=O)OCH₃, F, A20], [1663:C(=O)OCH₃, Cl, A20], [1664:C(=O)OCH₃, Br, A20], [1665:C(=O)OCH₃, CH₃, A20], [1666:C(=O)OCH₃, CH₂CH₃, A20], [1667:C(=O)O(CH₃)₃, H, A20], [1668:C(=O)O(CH₃)₃, F, A20], [1669:C(=O)O(CH₃)₃, Cl, A20], [1670:C(=O)O(CH₃)₃, Br, A20], [1671:C(=O)O(CH₃)₃, CH₃, A20], [1672:C(=O)O(CH₃)₃, CH₂CH₃, A20], [1673:C(=O)NH₂, H, A20], [1674:C(=O)NH₂, F, A20], [1675:C(=O)NH₂, Cl, A20], [1676:C(=O)NH₂, Br, A20], [1677:C(=O)NH₂, CH₃, A20], [1678:C(=O)NH₂, CH₂CH₃, A20], [1679:C(=O)NH(CH₃), H, A20], [1680:C(=O)NH(CH₃), F, A20], [1681:C(=O)NH(CH₃), Cl, A20], [1682:C(=O)NH(CH₃), Br, A20], [1683:C(=O)NH(CH₃), CH₃, A20], [1684:C(=O)NH(CH₃), CH₂CH₃, A20], [1685:C(=O)NH(CH₂CH₃), H, A20], [1686:C(=O)NH(CH₂CH₃), F, A20], [1687:C(=O)NH(CH₂CH₃), Cl, A20], [1688:C(=O)(CH₂CH₃), Br, A20], [1689:C(=O)NH(CH₂CH₃), CH₃, A20], [1690:C(=O)NH(CH₂CH₃), CH₂CH₃, A20], [1691:C(=O)N(CH₃)₂, H, A20], [1692:C(=O)N(CH₃)₂, F, A20], [1693:C(=O)N(CH₃)₂, Cl, A20], [1694:C(=O)N(CH₃)₂, Br, A20], [1695:C(=O)N(CH₃)₂, CH₃, A20], [1696:C(=O)N(CH₃)₂, CH₂CH₃, A20], [1697:C(=S)OCH₃, H, A20], [1698:C(=S)OCH₃, F, A20], [1699:C(=S)OCH₃, Cl, A20], [1700:C(=S)OCH₃, Br, A20], [1701:C(=S)OCH₃, CH₃, A20], [1702:C(=S)OCH₃, CH₂CH₃, A20], [1703:C(=S)NH₂, H, A20], [1704:C(=S)NH₂, F, A20], [1705:C(=S)NH₂, Cl, A20], [1706:C(=S)NH₂, Br, A20], [1707:C(=S)NH₂, CH₃, A20], [1708:C(=S)NH₂, CH₂CH₃, A20], [1709:C(=S)NH(CH₃), H, A20], [1710:C(=S)NH(CH₃), F, A20], [1711:C(=S)NH(CH₃), Cl, A20], [1712:C(=S)NH(CH₃), Br, A20], [1713:C(=S)NH(CH₃), CH₃, A20], [1714:C(=S)NH(CH₃), CH₂CH₃, A20], [1715:C(=S)N(CH₃)₂, H, A20], [1716:C(=S)N(CH₃)₂, F, A20], [1717:C(=S)N(CH₃)₂, Cl, A20], [1718:C(=S)N(CH₃)₂, Br, A20], [1719:C(=S)N(CH₃)₂, CH₃, A20], [1720:C(=S)N(CH₃)₂, CH₂CH₃, A20], [1721:H, H, A21], [1722:H, F, A21], [1723:H, Cl, A21], [1724:H, Br, A21], [1725:H, CH₃, A21], [1726:H, CH₂CH₃, A21], [1727:F, F, A21], [1728:F, Cl, A21], [1729:F, Br, A21], [1730:F, CH₃, A21], [1731:F, CH₂CH₃, A21], [1732:Cl, Cl, A21], [1733:Cl, Br, A21], [1734:Cl, CH₃, A21], [1735:Cl, CH₂CH₃, A21], [1736:Br, Br, A21], [1737:Br, CH₃, A21], [1738:Br, CH₂CH₃, A21], [1739:CH₃, CH₃, A21], [1740:CH₃, CH₂CH₃, A21], [1741:CN, H, A21], [1742:CN, F, A21], [1743:CN, Cl, A21], [1744:CN, Br, A21], [1745:CN, CH₃, A21], [1746:CN, CH₂CH₃, A21], [1747:C(=O)OCH₃, H, A21], [1748:C(=O)OCH₃, F, A21], [1749:C(=O)OCH₃, Cl, A21], [1750:C(=O)OCH₃, Br, A21], [1751:C(=O)OCH₃, CH₃, A21], [1752:C(=O)OCH₃, CH₂CH₃, A21], [1753:C(=O)O(CH₃)₃, H, A21], [1754:C(=O)O(CH₃)₃, F, A21], [1755:C(=O)O(CH₃)₃, Cl, A21], [1756:C(=O)O(CH₃)₃, Br, A21], [1757:C(=O)O(CH₃)₃, CH₃, A21], [1758:C(=O)O(CH₃)₃, CH₂CH₃, A21], [1759:C(=O)NH₂, H, A21], [1760:C(=O)NH₂, F, A21], [1761:C(=O)NH₂, Cl, A21], [1762:C(=O)NH₂, Br, A21], [1763:C(=O)NH₂, CH₃, A21], [1764:C(=O)NH₂, CH₂CH₃, A21], [1765:C(=O)NH(CH₃), H, A21], [1766:C(=O)NH(CH₃), F, A21], [1767:C(=O)NH(CH₃), Cl, A21], [1768:C(=O)NH(CH₃), Br, A21], [1769:C(=O)NH(CH₃), CH₃, A21], [1770:C(=O)NH(CH₃), CH₂CH₃, A21], [1771:C(=O)NH(CH₂CH₃), H, A21], [1772:C(=O)NH(CH₂CH₃), F, A21], [1773:C(=O)NH(CH₂CH₃), Cl, A21], [1774:C(=O)NH(CH₂CH₃), Br, A21], [1775:C(=O)NH(CH₂CH₃), CH₃, A21], [1776:C(=O)NH(CH₂CH₃), CH₂CH₃, A21], [1777:C(=O)N(CH₃)₂, H, A21], [1778:C(=O)N(CH₃)₂, F, A21], [1779:C(=O)N(CH₃)₂, Cl, A21], [1780:C(=O)N(CH₃)₂, Br, A21], [1781:C(=O)N(CH₃)₂, CH₃, A21], [1782:C(=O)N(CH₃)₂, CH₂CH₃, A21], [1783:C(=S)OCH₃, H, A21], [1784:C(=S)OCH₃, F, A21], [1785:C(=S)OCH₃, Cl, A21], [1786:C(=S)OCH₃, Br, A21], [1787:C(=S)OCH₃, CH₃, A21], [1788:C(=S)OCH₃, CH₂CH₃, A21], [1789:C(=S)NH₂, H, A21], [1790:C(=S)NH₂, F, A21], [1791:C(=S)NH₂, Cl, A21], [1792:C(=S)NH₂, Br, A21], [1793:C(=S)NH₂, CH₃, A21], [1794:C(=S)NH₂, CH₂CH₃, A21], [1795:C(=S)NH(CH₃), H, A21], [1796:C(=S)NH(CH₃), F, A21], [1797:C(=S)NH(CH₃), Cl, A21], [1798:C(=S)NH(CH₃), Br, A21], [1799:C(=S)NH(CH₃), CH₃, A21], [1800:C(=S)NH(CH₃), CH₂CH₃, A21], [1801:C(=S)N(CH₃)₂, H, A21], [1802:C(=S)N(CH₃)₂, F, A21], [1803:C(=S)N(CH₃)₂, Cl, A21], [1804:C(=S)N(CH₃)₂, Br, A21], [1805:C(=S)N(CH₃)₂, CH₃, A21], [1806:C(=S)N(CH₃)₂, CH₂CH₃, A21], [1807:H, H, A22], [1808:H, F, A22], [1809:H, Cl, A22], [1810:H, Br, A22], [1811:H, CH₃, A22], [1812:H, CH₂CH₃, A22], [1813:F, F, A22], [1814:F, Cl, A22], [1815:F, Br, A22], [1816:F, CH₃, A22], [1817:F, CH₂CH₃, A22], [1818:Cl, Cl, A22], [1819:Cl, Br, A22], [1820:Cl, CH₃, A22], [1821:Cl, CH₂CH₃, A22], [1822:Br, Br, A22], [1823:Br, CH₃, A22], [1824:Br, CH₂CH₃, A22], [1825:CH₃, CH₃, A22], [1826:CH₃, CH₂CH₃, A22], [1827:CN, H, A22], [1828:CN, F, A22], [1829:CN, Cl, A22], [1830:CN, Br, A22], [1831:CN, CH₃, A22], [1832:CN, CH₂CH₃, A22], [1833:C(=O)OCH₃, H, A22], [1834:C(=O)OCH₃, F, A22], [1835:C(=O)OCH₃, Cl, A22], [1836:C(=O)OCH₃, Br, A22], [1837:C(=O)OCH₃, CH₃, A22], [1838:C(=O)OCH₃, CH₂CH₃, A22], [1839:C(=O)O(CH₃)₃, H, A22], [1840:C(=O)O(CH₃)₃, F, A22], [1841:C(=O)O(CH₃)₃, Cl, A22], [1842:C(=O)O(CH₃)₃, Br, A22], [1843:C(=O)O(CH₃)₃, CH₃, A22], [1844:C(=O)O(CH₃)₃, CH₂CH₃, A22], [1845:C(=O)NH₂, H, A22], [1846:C(=O)NH₂, F, A22], [1847:C(=O)NH₂, Cl, A22], [1848:C(=O)NH₂, Br, A22], [1849:C(=O)NH₂, CH₃, A22], [1850:C(=O)NH₂, CH₂CH₃, A22], [1851:C(=O)NH(CH₃), H, A22], [1852:C(=O)

(CH₃), F, A22], [1853:C(=O)NH(CH₃), Cl, A22], [1854: C(=O)NH(CH₃), Br, A22], [1855:C(=O)NH(CH₃), CH₃, A22], [1856:C(=O)NH(CH₃), CH₂CH₃, A22], [1857:C(=O)NH(CH₂CH₃), H, A22], [1858:C(=O)NH (CH₂CH₃), F, A22], [1859:C(=O)NH(CH₂CH₃), Cl, A22], [1860:C(=O)NH(CH₂CH₃), Br, A22], [1861:C (=O)NH(CH₂CH₃), CH₃, A22], [1862:C(=O)NH (CH₂CH₃), CH₂CH₃, A22], [1863:C(=O)N(CH₃)₂, H, A22], [1864:C(=O)N(CH₃)₂, F, A22], [1865:C(=O)N (CH₃)₂, Cl, A22], [1866:C(=O)N(CH₃)₂, Br, A22], [1867: C(=O)N(CH₃)₂, CH₃, A22], [1868:C(=O)N(CH₃)₂, CH₂CH₃, A22], [1869:C(=S)OCH₃, H, A22], [1870:C (=S)OCH₃, F, A22], [1871:C(=S)OCH₃, Cl, A22], [1872:C(=S)OCH₃, Br, A22], [1873:C(=S)OCH₃, CH₃, A22], [1874:C(=S)OCH₃, CH₂CH₃, A22], [1875:C(=S) NH₂, H, A22], [1876:C(=S)NH₂, F, A22], [1877:C(=S) NH₂, Cl, A22], [1878:C(=S)NH₂, Br, A22], [1879:C(=S) NH₂, CH₃, A22], [1880:C(=S)NH₂, CH₂CH₃, A22], [1881:C(=S)NH(CH₃), H, A22], [1882:C(=S)NH(CH₃), F, A22], [1883:C(=S)NH(CH₃), Cl, A22], [1884:C(=S) NH(CH₃), Br, A22], [1885:C(=S)NH(CH₃), CH₃, A22], [1886:C(=S)NH(CH₃), CH₂CH₃, A22], [1887:C(=S)N (CH₃)₂, H, A22], [1888:C(=S)N(CH₃)₂, F, A22], [1889: C(=S)N(CH₃)₂, Cl, A22], [1890:C(=S)N(CH₃)₂, Br, A22], [1891:C(=S)N(CH₃)₂, CH₃, A22], [1892:C(=S)N (CH₃)₂, CH₂CH₃, A22], [1893:H, H, A23], [1894:H, F, A23], [1895:H, Cl, A23], [1896:H, Br, A23], [1897:H, CH₃, A23], [1898:H, CH₂CH₃, A23], [1899:F, F, A23], [1900:F, Cl, A23], [1901:F, Br, A23], [1902:F, CH₃, A2 3], [1903:F, CH₂CH₃, A23], [1904:Cl, Cl, A23], [1905:Cl, Br, A23], [1906:Cl, CH₃, A23], [1907:Cl, CH₂CH₃, A23], [1908:Br, Br, A23], [1909:Br, CH₃, A23], [1910:Br, CH₂CH₃, A23], [1911:CH₃, CH₃, A23], [1912:CH₃, CH₂CH₃, A23], [1913:CN, H, A23], [1914:CN, F, A23], [1915:CN, Cl, A23], [1916:CN, Br, A23], [1917:CN, CH₃, A23], [1918:CN, CH₂CH₃, A23], [1919:C(=O)OCH₃, H, A23], [1920:C(=O)OCH₃, F, A23], [1921:C(=O)OCH₃, Cl, A23], [1922:C(=O)OCH₃, Br, A23], [1923:C(=O) OCH₃, CH₃, A23], [1924:C(=O)OCH₃, CH₂CH₃, A23], [1925:C(=O)O(CH₃)₃, H, A23], [1926:C(=O)O(CH₃), F, A23], [1927:C(=O)O(CH₃)₃, Cl, A23], [1928:C(=O) O(CH₃)₃, Br, A23], [1929:C(=O)O(CH₃)₃, CH₃, A23], [1930:C(=O)O(CH₃)₃, CH₂CH₃, A23], [1931:C(=O) NH₂, H, A23], [1932:C(=O)NH₂, F, A23], [1933:C(=O) NH₂, Cl, A23], [1934:C(=O)NH₂, Br, A23], [1935:C (=O)NH₂, CH₃, A23], [1936:C(=O)NH₂, CH₂CH₃, A23], [1937:C(=O)NH(CH₃), H, A23], [1938:C(=O) NH(CH₃), F, A23], [1939:C(=O)NH(CH₃), Cl, A23], [1940:C(=O)NH(CH₃), Br, A23], [1941:C(=O)NH (CH₃), CH₃, A23], [1942:C(=O)NH(CH₃), CH₂CH₃, A23], [1943:C(=O)NH(CH₂CH₃), H, A23], [1944:C (=O)NH(CH₂CH₃), F, A23], [1945:C(=O)NH (CH₂CH₃), Cl, A23], [1946:C(=O)NH(CH₂CH₃), Br, A23], [1947:C(=O)NH(CH₂CH₃), CH₃, A23], [1948:C (=O)NH(CH₂CH₃), CH₂CH₃, A23], [1949:C(=O)N (CH₃)₂, H, A23], [1950:C(=O)N(CH₃)₂, F, A23], [1951: C(=O)N(CH₃)₂, Cl, A23], [1952:C(=O)N(CH₃)₂, Br, A23], [1953:C(=O)N(CH₃)₂, CH₃, A23], [1954:C(=O) N(CH₃)₂, CH₂CH₃, A23], [1955:C(=S)OCH₃, H, A23], [1956:C(=S)OCH₃, F, A23], [1957:C(=S)OCH₃, Cl, A23], [1958:C(=S)OCH₃, Br, A23], [1959:C(=S)OCH₃, CH₃, A23], [1960:C(=S)OCH₃, CH₂CH₃, A23], [1961:C (=S)NH₂, H, A23], [1962:C(=S)NH₂, F, A23], [1963:C (=S)NH₂, Cl, A23], [1964:C(=S)NH₂, Br, A23], [1965: C(=S)NH₂, CH₃, A23], [1966:C(=S)NH₂, CH₂CH₃, A23], [1967:C(=S)NH(CH₃), H, A23], [1968:C(=S)NH (CH₃), F, A23], [1969:C(=S)NH(CH₃), Cl, A23], [1970: C(=S)NH(CH₃), Br, A23], [1971:C(=S)NH(CH₃), CH₃, A23], [1972:C(=S)NH(CH₃CH₂CH₃, A23], [1973:C (=S)N(CH₃)₂, H, A23], [1974:C(=S)N(CH₃)₂, F, A23], [1975:C(=S)N(CH₃)₂, Cl, A23], [1976:C(=S)N(CH₃)₂, Br, A23], [1977:C(=S)N(CH₃)₂, CH₃, A23], [1978:C (=S)N(CH₃)₂, CH₂CH₃, A23], [1979:H, H, A24], [1980: H, F, A24], [1981:H, Cl, A24], [1982:H, Br, A24], [1983:H, CH₃, A24], [1984:H, CH₂CH₃, A24], [1985:F, F, A24], [1986:F, Cl, A24], [1987:F, Br, A24], [1988:F, CH₃, A24], [1989:F, CH₂CH₃, A24], [1990:Cl, Cl, A24], [1991:Cl, Br, A24], [1992:Cl, CH₃, A24], [1993:Cl, CH₂CH₃, A24], [1994:Br, Br, A24], [1995:Br, CH₃, A24], [1996:Br, CH₂CH₃, A24], [1997:CH₃, CH₃, A24], [1998:CH₃, CH₂CH₃, A24], [1999:CN, H, A24], [2000:CN, F, A24], [2001:CN, Cl, A24], [2002:CN, Br, A24], [2003:CN, CH₃, A24], [2004:CN, CH₂CH₃, A24], [2005:C(=O)OCH₃, H, A24], [2006:C(=O)OCH₃, F, A24], [2007:C(=O)OCH₃, Cl, A24], [2008:C(=O)OCH₃, Br, A24], [2009:C(=O) OCH₃, CH₃, A24], [2010:C(=O)OCH₃, CH₂CH₃, A24], [2011:C(=O)O(CH₃)₃, H, A24], [2012:C(=O)O(CH₃)₃, F, A24], [2013:C(=O)O(CH₃)₃, Cl, A24], [2014:C(=O) O(CH₃)₃, Br, A24], [2015:C(=O)O(CH₃)₃, CH₃, A24], [2016:C(=O)O(CH₃)₃, CH₂CH₃, A24], [2017:C(=O) NH₂, H, A24], [2018:C(=O)NH₂, F, A24], [2019:C(=O) NH₂, Cl, A24], [2020:C(=O)NH₂, Br, A24], [2021:C (=O)NH₂, CH₃, A24], [2022:C(=O)NH₂, CH₂CH₃, A24], [2023:C(=O)NH(CH₃), H, A24], [2024:C(=O) NH(CH₃), F, A24], [2025:C(=O)NH(CH₃), Cl, A24], [2026:C(=O)NH(CH₃), Br, A24], [2027:C(=O)NH (CH₃), CH₃, A24], [2028:C(=O)NH(CH₃), CH₂CH₃, A24], [2029:C(=O)NH(CH₂CH₃), H, A24], [2030:C (=O)NH(CH₂CH₃), F, A24], [2031:C(=O)NH (CH₂CH₃), Cl, A24], [2032:C(=O)NH(CH₂CH₃), Br, A24], [2033:C(=O)NH(CH₂CH₃), CH₃, A24], [2034:C (=O)NH(CH₂CH₃), CH₂CH₃, A24], [2035:C(=O)N (CH₃)₂, H, A24], [2036:C(=O)N(CH₃)₂, F, A24], [2037: C(=O)N(CH₃)₂, Cl, A24], [2038:C(=O)N(CH₃)₂, Br, A24], [2039:C(=O)N(CH₃)₂, CH₃, A24], [2040:C(=O) N(CH₃)₂, CH₂CH₃, A24], [2041:C(=S)OCH₃, H, A24], [2042:C(=S)OCH₃, F, A24], [2043:C(=S)OCH₃, Cl, A24], [2044:C(=S)OCH₃, Br, A24], [2045:C(=S)OCH₃, CH₃, A24], [2046:C(=S)OCH₃, CH₂CH₃, A24], [2047:C (=S)NH₂, H, A24], [2048:C(=S)NH₂, F, A24], [2049:C (=S)NH₂, Cl, A24], [2050:C(=S)NH₂, Br, A24], [2051: C(=S)NH₂, CH₃, A24], [2052:C(=S)NH₂, CH₂CH₃, A24], [2053:C(=S)NH(CH₃), H, A24], [2054:C(=S)NH (CH₃), F, A24], [2055:C(=S)NH(CH₃), Cl, A24], [2056: C(=S)NH(CH₃), Br, A24], [2057:C(=S)NH(CH₃), CH₃, A24], [2058:C(=S)NH(CH₃), CH₂CH₃, A24], [2059:C (=S)N(CH₃)₂, H, A24], [2060:C(=S)N(CH₃)₂, F, A24], [2061:C(=S)N(CH₃)₂, Cl, A24], [2062:C(=S)N(CH₃)₂, Br, A24], [2063:C(=S)N(CH₃)₂, CH₃, A24], [2064:C (=S)N(CH₃)₂, CH₂CH₃, A24], [2065:H, H, A25], [2066: H, F, A25], [2067:H, Cl, A25], [2068:H, Br, A25], [2069:H, CH₃, A25], [2070:H, CH₂CH₃, A25], [2071:F, F, A25], [2072:F, Cl, A25], [2073:F, Br, A25], [2074:F, CH₃, A25], [2075:F, CH₂CH₃, A25], [2076:Cl, Cl, A25], [2077:Cl, Br, A25], [2078:Cl, CH₃, A25], [2079:Cl, CH₂CH₃, A25], [2080:Br, Br, A25], [2081:Br, CH₃, A25], [2082:Br, CH₂CH₃, A25], [2083:CH₃, CH₃, A25], [2084:CH₃, CH₂CH₃, A25], [2085:CN, H, A25], [2086:CN, F, A25], [2087:CN, Cl, A25], [2088:CN, Br, A25], [2089:CN, CH₃, A25], [2090:CN, CH₂CH₃, A25], [2091:C(=O)OCH₃, H, A25], [2092:C(=O)OCH₃, F, A25], [2093:C(=O)OCH₃, Cl, A25], [2094:C(=O)OCH₃, Br, A25], [2095:C(=O) OCH₃, CH₃, A25], [2096:C(=O)OCH₃, CH₂CH₃, A25], [2097:C(=O)O(CH₃)₃, H, A25], [2098:C(=O)O(CH₃)₃,

F, A25], [2099:C(=O)O(CH₃)₃, Cl, A 25], [2100:C(=O) O(CH₃)₃, Br, A25], [2101:C(=O)O(CH₃)₃, CH₃, A25], [2102:C(=O)O(CH₃)₃, CH₂CH₃, A25], [2103:C(=O) NH₂, H, A25], [2104:C(=O)NH₂, F, A25], [2105:C(=O) NH₂, Cl, A25], [2106:C(=O)NH₂, Br, A25], [2107:C(=O)NH₂, CH₃, A25], [2108:C(=O)NH₂, CH₂CH₃, A25], [2109:C(=O)NH(CH₃), H, A25], [2110:C(=O) NH(CH₃), F, A25], [2111:C(=O)NH(CH₃), Cl, A25], [2112:C(=O)NH(CH₃), Br, A25], [2113:C(=O)NH(CH₃), CH₃, A25], [2114:C(=O)NH(CH₃), CH₂CH₃, A25], [2115:C(=O)NH(CH₂CH₃), H, A25], [2116:C(=O)NH(CH₂CH₃), F, A25], [2117:C(=O)NH(CH₂CH₃), Cl, A25], [2118:C(=O)NH(CH₂CH₃), Br, A25], [2119:C(=O)NH(CH₂CH₃), CH₃, A25], [2120:C(=O)NH(CH₂CH₃), CH₂CH₃, A25], [2121:C(=O)N(CH₃)₂, H, A25], [2122:C(=O)N(CH₃)₂, F, A25], [2123:C(=O)N(CH₃)₂, Cl, A25], [2124:C(=O)N(CH₃)₂, Br, A25], [2125:C(=O)N(CH₃)₂, CH₃, A25], [2126:C(=O)N(CH₃)₂, CH₂CH₃, A25], [2127:C(=S)OCH₃, H, A25], [2128:C(=S)OCH₃, F, A25], [2129:C(=S)OCH₃, Cl, A25], [2130:C(=S)OCH₃, Br, A25], [2131:C(=S)OCH₃, CH₃, A25], [2132:C(=S)OCH₃, CH₂CH₃, A25], [2133:C(=S)NH₂, H, A25], [2134:C(=S)NH₂, F, A25], [2135:C(=S)NH₂, Cl, A25], [2136:C(=S)NH₂, Br, A25], [2137:C(=S)NH₂, CH₃, A25], [2138:C(=S)NH₂, CH₂CH₃, A25], [2139:C(=S)NH(CH₃), A25], [2140:C(=S)NH(CH₃), F, A25], [2141:C(=S)NH(CH₃), Cl, A25], [2142:C(=S)NH(CH₃), Br, A25], [2143:C(=S)NH(CH₃), CH₃, A25], [2144:C(=S)NH(CH₃), CH₂CH₃, A25], [2145:C(=S)N(CH₃)₂, H, A25], [2146:C(=S)N(CH₃)₂, F, A25], [2147:C(=S)N(CH₃)₂, Cl, A25], [2148:C(=S)N(CH₃)₂, Br, A25], [2149:C(=S)N(CH₃)₂/CH₃, A25], [2150:C(=S)N(CH₃)₂, CH₂CH₃, A25], [2151:H, H, A26], [2152:H, A26], [2153:H, Cl, A26], [2154:H, Br, A26], [2155:H, CH₃, A26], [2156:H, CH₂CH₃, A26], [2157:F, F, A26], [2158:F, Cl, A26], [2159:F, Br, A26], [2160:F, CH₃, A26], [2161:F, CH₂CH₃, A26], [2162:Cl, Cl, A26], [2163:Cl, Br, A26], [2164:Cl, CH₃, A26], [2165:Cl, CH₂CH₃, A26], [2166:Br, Br, A26], [2167 Br, CH₃, A26], [2168:Br, CH₂CH₃, A26], [2169:CH₃, CH₃, A26], [2170:CH₃, CH₂CH₃, A26], [2171:CN, H, A26], [2172:CN, F, A26], [2173:CN, Cl, A26], [2174:CN, Br, A26], [2175:CN, CH₃, A26], [2176:CN, CH₂CH₃, A26], [2177:C(=O)OCH₃, H, A26], [2178:C(=O)OCH₃, F, A26], [2179:C(=O)OCH₃, Cl, A26], [2180:C(=O)OCH₃, Br, A26], [2181:C(=O) OCH₃, CH₃, A26], [2182:C(=O)OCH₃, CH₂CH₃, A26], [2183:C(=O)O(CH₃)₃, H, A26], [2184:C(=O)O(CH₃)₃, F, A26], [2185:C(=O)O(CH₃)₃, Cl, A26], [2186:C(=O) O(CH₃)₃, Br, A26], [2187:C(=O)O(CH₃)₃, CH₃, A26], [2188:C(=O)O(CH₃)₃, CH₂CH₃, A26], [2189:C(=O) NH₂, H, A26], [2190:C(=O)NH₂, F, A26], [2191:C(=O) NH₂, Cl, A26], [2192:C(=O)NH₂, Hr, A26], [2193:C(=O)NH₂, CH₃, A26], [2194:C(=O)NH₂, CH₂CH₃, A26], [2195:C(=O)NH(CH₃), H, A26], [2196:C(=O) NH(CH₃), F, A26], [2197:C(=O)NH(CH₃), Cl, A26], [2198:C(=O)NH(CH₃), Br, A26], [2199:C(=O)NH(CH₃), CH₃, A26], [2200:C(=O)NH(CH₃), CH₂CH₃, A26], [2201:C(=O)NH(CH₂CH₃), H, A26], [2202:C(=O)NH(CH₂CH₃), F, A26], [2203:C(=O)NH(CH₂CH₃), Cl, A26], [2204:C(=O)NH(CH₂CH₃), Br, A26], [2205:C(=O)NH(CH₂CH₃), CH₃, A26], [2206:C(=O)NH(CH₂CH₃), CH₂CH₃, A26], [2207:C(=O)N(CH₃)₂, H, A26], [2208:C(=O)N(CH₃)₂, F, A26], [2209:C(=O)N(CH₃)₂, Cl, A26], [2210:C(=O)N(CH₃)₂, Br, A26], [2211:C(=O)N(CH₃)₂, CH₃, A26], [2212:C(=O)N(CH₃)₂, CH₂CH₃, A26], [2213:C(=S)OCH₃, H, A26], [2214:C(=S)OCH₃, F, A26], [2215:C(=S)OCH₃, Cl, A26], [2216:C(=S)OCH₃, Br, A26], [2217:C(=S)OCH₃, CH₃, A26], [2218:C(=S)OCH₃, CH₂CH₃, A26], [2219:C(=S)NH₂, H, A26], [2220:C(=S)NH₂, F, A26], [2221:C(=S)NH₂, Cl, A26], [2222:C(=S)NH₂, Br, A26], [2223:C(=S)NH₂, CH₃, A26], [2224:C(=S)NH₂, CH₂CH₃, A26], [2225:C(=S)NH(CH₃), H, A26], [2226:C(=S)NH(CH₃), F, A26], [2227:C(=S)NH(CH₃), Cl, A26], [2228:C(=S)NH(CH₃), Br, A26], [2229:C(=S)NH(CH₃), CH₃, A26], [2230:C(=S)NH(CH₃), CH₂CH₃, A26], [2231:C(=S)N(CH₃)₂, H, A26], [2232:C(=S)N(CH₃)₂, F, A26], [2233:C(=S)N(CH₃)₂, Cl, A26], [2234:C(=S)N(CH₃)₂, Br, A26], [2235:C(=S)N(CH₃)₂, CH₃, A26], [2236:C(=S)N(CH₃)₂, CH₂CH₃, A26], [2237:H, H, A27], [2238:H, F, A27], [2239:H, Cl, A27], [2240:H, Br, A27], [2241:H, CH₃, A27], [2242:H, CH₂CH₃, A27], [2243:F, F, A27], [2244:F, Cl, A27], [2245:F, Br, A27], [2246:F, CH₃, A27], [2247:F, CH₂CH₃, A27], [2248:Cl, Cl, A27], [2249:Cl, Br, A27], [2250:Cl, CH₃, A27], [2251:Cl, CH₂CH₃, A27], [2252:Br, Br, A27], [2253:Br, CH₃, A27], [2254:Br, CH₂CH₃, A27], [2255:CH₃, CH₃, A27], [2256:CH₃, CH₂CH₃, A27], [2257:CN, H, A27], [2258:CN, F, A27], [2259:CN, Cl, A27], [2260:CN, Br, A27], [2261:CN, CH₃, A27], [2262:CN, CH₂CH₃, A27], [2263:C(=O)OCH₃, H, A27], [2264:C(=O)OCH₃, F, A27], [2265:C(=O)OCH₃, Cl, A27], [2266:C(=O)OCH₃, Br, A27], [2267:C(=O)OCH₃, CH₃, A27], [2268:C(=O)OCH₃, CH₂CH₃, A27], [2269:C(=O)O(CH₃)₃, H, A27], [2270:C(=O)O(CH₃)₃, F, A27], [2271:C(=O)O(CH₃)₃, Cl, A27], [2272:C(=O) O(CH₃)₃, Br, A27], [2273:C(=O)O(CH₃)₃, CH₃, A27], [2274:C(=O)O(CH₃)₃, CH₂CH₃, A27], [2275:C(=O) NH₂, H, A27], [2276:C(=O)NH₂, F, A27], [2277:C(=O) NH₂, Cl, A27], [2278:C(=O)NH₂, Br, A27], [2279:C(=O)NH₂, CH₃, A27], [2280:C(=O)NH₂, CH₂CH₃, A27], [2281:C(=O)NH(CH₃), H, A27], [2282:C(=O) NH(CH₃), F, A27], [2283:C(=O)NH(CH₃), Cl, A27], [2284:C(=O)NH(CH₃), Br, A27], [2285:C(=O)NH(CH₃), CH₃, A27], [2286:C(=O)NH(CH₃), CH₂CH₃, A27], [2287:C(=O)NH(CH₂CH₃), H, A27], [2288:C(=O)NH(CH₂CH₃), F, A27], [2289:C(=O)NH(CH₂CH₃), Cl, A27], [2290:C(=O)NH(CH₂CH₃), Br, A27], [2291:C(=O)NH(CH₂CH₃), CH₃, A27], [2292:C(=O)NH(CH₂CH₃), CH₂CH₃, A27], [2293:C(=O)N(CH₃)₂, H, A27], [2294:C(=O)N(CH₃)₂, F, A27], [2295:C(=O)N(CH₃)₂, Cl, A27], [2296:C(=O)N(CH₃)₂, Br, A27], [2297:C(=O)N(CH₃)₂, CH₃, A27], [2298:C(=O)N(CH₃)₂, CH₂CH₃, A27], [2299:C(=S)OCH₃, H, A27], [2300:C(=S)OCH₃, F, A27], [2301:C(=S)OCH₃, Cl, A27], [2302:C(=S)OCH₃, Br, A27], [2303:C(=S)OCH₃, CH₃, A27], [2304:C(=S)OCH₃, CH₂CH₃, A27], [2305:C(=S)NH₂, H, A27], [2306:C(=S)NH₂, F, A27], [2307:C(=S)NH₂, Cl, A27], [2308:C(=S)NH₂, Br, A27], [2309:C(=S)NH₂, CH₃, A27], [2310:C(=S)NH₂, CH₂CH₃, A27], [2311:C(=S)NH(CH₃), H, A27], [2312:C(=S)NH(CH₃), F, A27], [2313:C(=S)NH(CH₃), Cl, A27], [2314:C(=S)NH(CH₃), Br, A27], [2315:C(=S)NH(CH₃), CH₃, A27], [2316:C(=S)NH(CH₃), CH₂CH₃, A27], [2317:C(=S)N(CH₃)₂, H, A27], [2318:C(=S)N(CH₃)₂, F, A27], [2319:C(=S)N(CH₃)₂, Cl, A27], [2320:C(=S)N(CH₃)₂, Br, A27], [2321:C(=S)N(CH₃)₂, CH₃, A27], [2322:C(=S)N(CH₃)₂, CH₂CH₃, A27], [2323:H, H, A28], [2324:H, F, A28], [2325:H, Cl, A28], [2326:H, Br, A28], [2327:H, CH₃, A28], [2328:H, CH₂CH₃, A28], [2329:F, F, A28], [2330:F, Cl, A28], [2331:F, Br, A28], [2332:F, CH₃, A28], [2333:F, CH₂CH₃, A28], [2334:Cl, Cl, A28], [2335:Cl, Br, A28], [2336:Cl, CH₃, A28], [2337:Cl, CH₂CH₃, A28], [2338:Br, Br, A28], [2339:Br, CH₃, A28], [2340:Br, CH₂CH₃, A28], [2341:CH₃, CH₃, A28], [2342:CH₃,

CH₂CH₃, A28], [2343:CN, H, A28], [2344:CN, F, A28], [2345:CN, Cl, A28], [2346:CN, Br, A28], [2347:CN, CH₃, A28], [2348:CN, CH₂CH₃, A28], [2349:C(=O)OCH₃, H, A28], [2350:C(=O)OCH₃, F, A28], [2351:C(=O)OCH₃, Cl, A28], [2352:C(=O)OCH₃, Br, A28], [2353:C(=O)OCH₃, CH₃, A28], [2354:C(=O)OCH₃, CH₂CH₃, A28], [2355:C(=O)O(CH₃)₃, H, A28], [2356:C(=O)O(CH₃)₃, F, A28], [2357:C(=O)O(CH₃)₃, Cl, A28], [2358:C(=O)O(CH₃)₃, Br, A28], [2359:C(=O)O(CH₃)₃, CH₃, A28], [2360:C(=O)O(CH₃)₃, CH₂CH₃, A28], [2361:C(=O)NH₂, H, A28], [2362:C(=O)NH₂, F, A28], [2363:C(=O)NH₂, Cl, A28], [2364:C(=O)NH₂, Br, A28], [2365:C(=O)NH₂, CH₃, A28], [2366:C(=O)NH₂, CH₂CH₃, A28], [2367:C(=O)NH(CH₃), H, A28], [2368:C(=O)NH(CH₃), F, A28], [2369:C(=O)NH(CH₃), Cl, A28], [2370:C(=O)NH(CH₃), Br, A28], [2371:C(=O)NH(CH₃), CH₃, A28], [2372:C(=O)NH(CH₃), CH₂CH₃, A28], [2373:C(=O)NH(CH₂CH₃), H, A28], [2374:C(=O)NH(CH₂CH₃), F, A28], [2375:C(=O)NH(CH₂CH₃), Cl, A28], [2376:C(=O)NH(CH₂CH₃), Br, A28], [2377:C(=O)NH(CH₂CH₃), CH₃, A28], [2378:C(=O)NH(CH₂CH₃), CH₂CH₃, A28], [2379:C(=O)N(CH₃)₂, H, A28], [2380:C(=O)N(CH₃)₂, F, A28], [2381:C(=O)N(CH₃)₂, Cl, A28], [2382:C(=O)N(CH₃)₂, Br, A28], [2383:C(=O)N(CH₃)₂, CH₃, A28], [2384:C(=O)N(CH₃)₂, CH₂CH₃, A28], [2385:C(=S)OCH₃, H, A28], [2386:C(=S)OCH₃, F, A28], [2387:C(=S)OCH₃, Cl, A28], [2388:C(=S)OCH₃, Br, A28], [2389:C(=S)OCH₃, CH₃, A28], [2390:C(=S)OCH₃, CH₂CH₃, A28], [2391:C(=S)NH₂, H, A28], [2392:C(=S)NH₂, F, A28], [2393:C(=S)NH₂, Cl, A28], [2394:C(=S)NH₂, Br, A28], [2395:C(=S)NH₂, CH₃, A28], [2396:C(=S)NH₂, CH₂CH₃, A28], [2397:C(=S)NH(CH₃), H, A28], [2398:C(=S)NH(CH₃), F, A28], [2399:C(=S)NH(CH₃), Cl, A28], [2400:C(=S)NH(CH₃), Br, A28], [2401:C(=S)NH(CH₃), CH₃, A28], [2402:C(=S)NH(CH₃), CH₂CH₃, A28], [2403:C(=S)N(CH₃)₂, H, A28], [2404:C(=S)N(CH₃)₂, F, A28], [2405:C(=S)N(CH₃)₂, Cl, A28], [2406:C(=S)N(CH₃)₂, Br, A28], [2407:C(=S)N(CH₃)₂, CH₃, A28], [2408:C(=S)N(CH₃)₂, CH₂CH₃, A28], [2409:H, H, A29], [2410:H, F, A29], [2411:H, Cl, A29], [2412:H, Br, A29], [2413:H, CH₃, A29], [2414:H, CH₂CH₃, A29], [2415:F, F, A29], [2416:F, Cl, A29], [2417:F, Br, A29], [2418:F, CH₃, A29], [2419:F, CH₂CH₃, A29], [2420:Cl, Cl, A29], [2421:Cl, Br, A29], [2422:Cl, CH₃, A29], [2423:Cl, CH₂CH₃, A29], [2424:Br, Br, A29], [2425:Br, CH₃, A29], [2426:Br, CH₂CH₃, A29], [2427:CH₃, CH₃, A29], [2428:CH₃, CH₂CH₃, A29], [2429:CN, H, A29], [2430:CN, F, A29], [2431:CN, Cl, A29], [2432:CN, Br, A29], [2433:CH₃, A29], [2434:CN, CH₂CH₃, A29], [2435:C(=O)OCH₃, H, A29], [2436:C(=O)OCH₃, F, A29], [2437:C(=O)OCH₃, Cl, A29], [2438:C(=O)OCH₃, Br, A29], [2439:C(=O)OCH₃, CH₃, A29], [2440:C(=O)OCH₃, CH₂CH₃, A29], [2441:C(=O)O(CH₃)₃, H, A29], [2442:C(=O)O(CH₃)₃, F, A29], [2443:C(=O)O(CH₃)₃, Cl, A29], [2444:C(=O)O(CH₃)₃, Br, A29], [2445:C(=O)O(CH₃)₃, CH₃, A29], [2446:C(=O)O(CH₃)₃, CH₂CH₃, A29], [2447:C(=O)NH₂, H, A29], [2448:C(=O)NH₂, F, A29], [2449:C(=O)NH₂, Cl, A29], [2450:C(=O)NH₂, Br, A29], [2451:C(=O)NH₂, CH₃, A29], [2452:C(=O)NH₂, CH₂CH₃, A29], [2453:C(=O)NH(CH₃), H, A29], [2454:C(=O)NH(CH₃), F, A29], [2455:C(=O)NH(CH₃), Cl, A29], [2456:C(=O)NH(CH₃), Br, A29], [2457:C(=O)NH(CH₃), CH₃, A29], [2458:C(=O)NH(CH₃), CH₂CH₃, A29], [2459:C(=O)NH(CH₂CH₃), H, A29], [2460:C(=O)NH(CH₂CH₃), F, A29], [2461:C(=O)NH(CH₂CH₃), Cl, A29], [2462:C(=O)NH(CH₂CH₃), Br, A29], [2463:C(=O)NH(CH₂CH₃), CH₃, A29], [2464:C(=O)NH(CH₂CH₃), CH₂CH₃, A29], [2465:C(=O)N(CH₃)₂, H, A29], [2466:C(=O)N(CH₃)₂, F, A29], [2467:C(=O)N(CH₃)₂, Cl, A29], [2468:C(=O)N(CH₃)₂, Br, A29], [2469:C(=O)N(CH₃)₂, CH₃, A29], [2470:C(=O)N(CH₃)₂, CH₂CH₃, A29], [2471:C(=S)OCH₃, H, A29], [2472:C(=S)OCH₃, F, A29], [2473:C(=S)OCH₃, Cl, A29], [2474:C(=S)OCH₃, Br, A29], [2475:C(=S)OCH₃, CH₃, A29], [2476:C(=S)OCH₃, CH₂CH₃, A29], [2477:C(=S)NH₂, H, A29], [2478:C(=S)NH₂, F, A29], [2479:C(=S)NH₂, Cl, A29], [2480:C(=S)NH₂, Br, A29], [2481:C(=S)NH₂, CH₃, A29], [2482:C(=S)NH₂, CH₂CH₃, A29], [2483:C(=S)NH(CH₃), H, A29], [2484:C(=S)NH(CH₃), F, A29], [2485:C(=S)NH(CH₃), Cl, A29], [2486:C(=S)NH(CH₃), Br, A29], [2487:C(=S)NH(CH₃), CH₃, A29], [2488:C(=S)NH(CH₃), CH₂CH₃, A29], [2489:C(=S)N(CH₃)₂, H, A29], [2490:C(=S)N(CH₃)₂, F, A29], [2491:C(=S)N(CH₃)₂, Cl, A29], [2492:C(=S)N(CH₃)₂, Br, A29], [2493:C(=S)N(CH₃)₂, CH₃, A29], [2494:C(=S)N(CH₃)₂, CH₂CH₃, A29], [2495:H, H, A30], [2496:H, F, A30], [2497:H, Cl, A30], [2498:H, Br, A30], [2499:H, CH₃, A30], [2500:H, CH₂CH₃, A30], [2501:F, F, A30], [2502:F, Cl, A30], [2503:F, Br, A30], [2504:F, CH₃, A30], [2505:F, CH₂CH₃, A30], [2506:Cl, Cl, A30], [2507:Cl, Br, A30], [2508:Cl, CH₃, A30], [2509:Cl, CH₂CH₃, A30], [2510:Br, Br, A30], [2511:Br, CH₃, A30], [2512:Br, CH₂CH₃, A30], [2513:CH₃, CH₃, A30], [2514:CH₃, CH₂CH₃, A30], [2515:CN, H, A30], [2516:CN, F, A30], [2517:CN, Cl, A30], [2518:CN, Br, A30], [2519:CN, CH₃, A30], [2520:CN, CH₂CH₃, A30], [2521:C(=O)OCH₃, H, A30], [2522:C(=O)OCH₃, F, A30], [2523:C(=O)OCH₃, Cl, A30], [2524:C(=O)OCH₃, Br, A30], [2525:C(=O)OCH₃, CH₃, A30], [2526:C(=O)OCH₃, CH₂CH₃, A30], [2527:C(=O)O(CH₃)₃, H, A30], [2528:C(=O)O(CH₃), F, A30], [2529:C(=O)(CH₃)₃, Cl, A30], [2530:C(=O)O(CH₃)₃, Br, A30], [2531:C(=O)O(CH₃)₃, CH₃, A30], [2532:C(=O)O(CH₃)₃, CH₂CH₃, A30], [2533:C(=O)NH₂, H, A30], [2534:C(=O)NH₂, F, A30], [2535:C(=O)NH₂, Cl, A30], [2536:C(=O)NH₂, Br, A30], [2537:C(=O)NH₂, CH₃, A30], [2538:C(=O)NH₂, CH₂CH₃, A30], [2539:C(=O)NH(CH₃), H, A30], [2540:C(=O)NH(CH₃), F, A30], [2541:C(=O)NH(CH₃), Cl, A30], [2542:C(=O)NH(CH₃), Br, A30], [2543:C(=O)NH(CH₃), CH₃, A30], [2544:C(=O)NH(CH₃), CH₂CH₃, A30], [2545:C(=O)NH(CH₂CH₃), H, A30], [2546:C(=O)NH(CH₂CH₃), F, A30], [2547:C(=O)NH(CH₂CH₃), Cl, A30], [2548:C(=O)NH(CH₂CH₃), Br, A30], [2549:C(=O)NH(CH₂CH₃), CH₃, A30], [2550:C(=O)NH(CH₂CH₃), CH₂CH₃, A30], [2551:C(=O)N(CH₃)₂, H, A30], [2552:C(=O)N(CH₃)₂, F, A30], [2553:C(=O)N(CH₃)₂, Cl, A30], [2554:C(=O)N(CH₃)₂, Br, A30], [2555:C(=O)N(CH₃)₂, CH₃, A30], [2556:C(=O)N(CH₃)₂, CH₂CH₃, A30], [2557:C(=S)OCH₃, H, A30], [2558:C(=S)OCH₃, F, A30], [2559:C(=S)OCH₃, Cl, A30], [2560:C(=S)OCH₃, Br, A30], [2561:C(=S)OCH₃, CH₃, A30], [2562:C(=S)OCH₃CH₂CH₃, A30], [2563:C(=S)NH₂, H, A30], [2564:C(=S)NH₂, F, A30], [2565:C(=S)NH₂, Cl, A30], [2566:C(=S)NH₂, Br, A30], [2567:C(=S)NH₂, CH₃, A30], [2568:C(=S)NH₂, CH₂CH₃, A30], [2569:C(=S)NH(CH₃), H, A30], [2570:C(=S)NH(CH₃), F, A30], [2571:C(=S)NH(CH₃), Cl, A30], [2572:C(=S)NH(CH₃), Br, A30], [2573:C(=S)NH(CH₃), CH₃, A30], [2574:C(=S)NH(CH₃), CH₂CH₃, A30], [2575:C(=S)N(CH₃)₂, H, A30], [2576:C(=S)N(CH₃)₂, F, A30], [2577:C(=S)N(CH₃)₂, Cl, A30], [2578:C(=S)N(CH₃)₂, Br, A30], [2579:C(=S)N(CH₃)₂, CH₃, A30], [2580:C(=S)N(CH₃)₂, CH₂CH₃, A30], [2581:H, H, A31], [2582:

H, F, A31], [2583:H, Cl, A31], [2584:H, Br, A31], [2585:H, CH₃, A31], [2586:H, CH₂CH₃, A31], [2587:F, F, A31], [2588:F, Cl, A31], [2589:F, Br, A31], [2590:F, CH₃, A31], [2591:F, CH₂CH₃, A31], [2592:Cl, Cl, A31], [2593:Cl, Br, A31], [2594:Cl, CH₃, A31], [2595:Cl, CH₂CH₃, A31], [2596:Br, Br, A31], [2597:Br, CH₃, A31], [2598:Br, CH₂CH₃, A31], [2599:CH₃, CH₃, A31], [2600:CH₃, CH₂CH₃, A31], [2601:CN, H, A31], [2602:CN, F, A31], [2603:CN, Cl, A31], [2604:CN, Br, A31], [2605:CN, CH₃, A31], [2606:CN, CH₂CH₃, A31], [2607:C(=O)OCH₃, H, A31], [2608:C(=O)OCH₃, F, A31], [2609:C(=O)OCH₃, Cl, A31], [2610:C(=O)OCH₃, Br, A31], [2611:C(=O)OCH₃, CH₃, A31], [2612:C(=O)OCH₃, CH₂CH₃, A31], [2613:C(=O)O(CH₃)₃, H, A31], [2614:C(=O)O(CH₃)₃, F, A31], [2615:C(=O)O(CH₃)₃, Cl, A31], [2616:C(=O)O(CH₃)₃, Br, A31], [2617:C(=O)O(CH₃)₃, CH₃, A31], [2618:C(=O)O(CH₃)₃, CH₂CH₃, A31], [2619:C(=O)NH₂, H, A31], [2620:C(=O)NH₂, F, A31], [2621:C(=O)NH₂, Cl, A31], [2622:C(=O)NH₂, Br, A31], [2623:C(=O)NH₂, CH₃, A31], [2624:C(=O)NH₂, CH₂CH₃, A31], [2625:C(=O)NH(CH₃), H, A31], [2626:C(=O)NH(CH₃), F, A31], [2627:C(=O)NH(CH₃), Cl, A31], [2628:C(=O)NH(CH₃), Br, A31], [2629:C(=O)NH(CH₃), CH₃, A31], [2630:C(=O)NH(CH₃), CH₂CH₃, A31], [2631:C(=O)NH(CH₂CH₃), H, A31], [2632:C(=O)NH(CH₂CH₃), F, A31], [2633:C(=O)NH(CH₂CH₃), Cl, A31], [2634:C(=O)NH(CH₂CH₃), Br, A31], [2635:C(=O)NH(CH₂CH₃), CH₃, A31], [2636:C(=O)NH(CH₂CH₃)CH₂CH₃, A31], [2637:C(=O)N(CH₃)₂, H, A31], [2638:C(=O)N(CH₃)₂, F, A31], [2639:C(=O)N(CH₃)₂, Cl, A31], [2640:C(=O)N(CH₃)₂, Br, A31], [2641:C(=O)N(CH₃)₂, CH₃, A31], [2642:C(=O)N(CH₃)₂, CH₂CH₃, A31], [2643:C(=S)OCH₃, H, A31], [2644:C(=S)OCH₃, F, A31], [2645:C(=S)OCH₃, Cl, A31], [2646:C(=S)OCH₃, Br, A31], [2647:C(=S)OCH₃, CH₃, A31], [2648:C(=S)OCH₃, CH₂CH₃, A31], [2649:C(=S)NH₂, H, A31], [2650:C(=S)NH₂, F, A31], [2651:C(=S)NH₂, Cl, A31], [2652:C(=S)NH₂, Br, A31], [2653:C(=S)NH₂, CH₃, A31], [2654:C(=S)NH₂, CH₂CH₃, A31], [2655:C(=S)NH(CH₃), H, A31], [2656:C(=S)NH(CH₃), F, A31], [2657:C(=S)NH(CH₃), Cl, A31], [2658:C(=S)NH(CH₃), Br, A31], [2659:C(=S)NH(CH₃), CH₃, A31], [2660:C(=S)NH(CH₃), CH₂CH₃, A31], [2661:C(=S)N(CH₃)₂, H, A31], [2662:C(=S)N(CH₃)₂, F, A31], [2663:C(=S)N(CH₃)₂, Cl, A31], [2664:C(=S)N(CH₃)₂, Br, A31], [2665:C(=S)N(CH₃)₂, CH₃, A31], [2666:C(=S)N(CH₃)₂, CH₂CH₃, A31], [2667:H, H, A32], [2668:H, F, A32], [2669:H, Cl, A32], [2670:H, Br, A32], [2671:H, CH₃, A32], [2672:H, CH₂CH₃, A32], [2673:F, F, A32], [2674:F, Cl, A32], [2675:F, Br, A32], [2676:F, CH₃, A32], [2677:F, CH₂CH₃, A32], [2678:Cl, Cl, A32], [2679:Cl, Br, A32], [2680:Cl, CH₃, A32], [2681:Cl, CH₂CH₃, A32], [2682:Br, Br, A32], [2683:Br, CH₃, A32], [2684:Br, CH₂CH₃, A32], [2685:CH₃, CH₃, A32], [2686:CH₃, CH₂CH₃, A32], [2687:CN, H, A32], [2688:CN, F, A32], [2689:CN, Cl, A32], [2690:CN, Br, A32], [2691:CN, CH₃, A32], [2692:CN, CH₂CH₃, A32], [2693:C(=O)OCH₃, H, A32], [2694:C(=O)OCH₃, F, A32], [2695:C(=O)OCH₃, Cl, A32], [2696:C(=O)OCH₃, Br, A32], [2697:C(=O)OCH₃, CH₃, A32], [2698:C(=O)OCH₃, CH₂CH₃, A32], [2699:C(=O)O(CH₃)₃, H, A32], [2700:C(=O)O(CH₃)₃, F, A32], [2701:C(=O)O(CH₃)₃, Cl, A32], [2702:C(=O)O(CH₃)₃, Br, A32], [2703:C(=O)O(CH₃)₃, CH₃, A32], [2704:C(=O)O(CH₃)₃, CH₂CH₃, A32], [2705:C(=O)NH₂, H, A32], [2706:C(=O)NH₂, F, A32], [2707:C(=O)NH₂, Cl, A32], [2708:C(=O)NH₂, Br, A32], [2709:C(=O)NH₂, CH₃, A32], [2710:C(=O)NH₂, CH₂CH₃, A32], [2711:C(=O)NH(CH₃), H, A32], [2712:C(=O)NH(CH₃), F, A32], [2713:C(=O)NH(CH₃), Cl, A32], [2714:C(=O)NH(CH₃), Br, A32], [2715:C(=O)NH(CH₃), CH₃, A32], [2716:C(=O)NH(CH₃), CH₂CH₃, A32], [2717:C(=O)NH(CH₂CH₃), H, A32], [2718:C(=O)NH(CH₂CH₃), F, A32], [2719:C(=O)NH(CH₂CH₃), Cl, A32], [2720:C(=O)NH(CH₂CH₃), Br, A32], [2721:C(=O)NH(CH₂CH₃), CH₃, A32], [2722:C(=O)NH(CH₂CH₃), CH₂CH₃, A32], [2723:C(=O)N(CH₃)₂, H, A32], [2724:C(=O)N(CH₃)₂, F, A32], [2725:C(=O)N(CH₃)₂, Cl, A32], [2726:C(=O)N(CH₃)₂, Br, A32], [2727:C(=O)N(CH₃)₂, CH₃, A32], [2728:C(=O)N(CH₃)₂, CH₂CH₃, A32], [2729:C(=S)OCH₃, H, A32], [2730:C(=S)OCH₃, F, A32], [2731:C(=S)OCH₃, Cl, A32], [2732:C(=S)OCH₃, Br, A32], [2733:C(=S)OCH₃, CH₃, A32], [2734:C(=S)OCH₃, CH₂CH₃, A32], [2735:C(=S)NH₂, H, A32], [2736:C(=S)NH₂, F, A32], [2737:C(=S)NH₂, Cl, A32], [2738:C(=S)NH₂, Br, A32], [2739:C(=S)NH₂, CH₃, A32], [2740:C(=S)NH₂, CH₂CH₃, A32], [2741:C(=S)NH(CH₃), H, A32], [2742:C(=S)NH(CH₃), F, A32], [2743:C(=S)NH(CH₃), Cl, A32], [2744:C(=S)NH(CH₃), Br, A32], [2745:C(=S)NH(CH₃), CH₃, A32], [2746:C(=S)NH(CH₃), CH₂CH₃, A32], [2747:C(=S)N(CH₃)₂, H, A32], [2748:C(=S)N(CH₃)₂, F, A32], [2749:C(=S)N(CH₃)₂, Cl, A32], [2750:C(=S)N(CH₃)₂, Br, A32], [2751:C(=S)N(CH₃)₂, CH₃, A32], [2752:C(=S)N(CH₃)₂, CH₂CH₃, A32], [2753:H, H, A33], [2754:H, F, A33], [2755:H, Cl, A33], [2756:H, Br, A33], [2757:H, CH₃, A33], [2758:H, CH₂CH₃, A33], [2759:F, F, A33], [2760:F, Cl, A33], [2761:F, Br, A33], [2762:F, CH₃, A33], [2763:F, CH₂CH₃, A33], [2764:Cl, Cl, A33], [2765:Cl, Br, A33], [2766:Cl, CH₃, A33], [2767:Cl, CH₂CH₃, A33], [2768:Br, Br, A33], [2769:Br, CH₃, A33], [2770:Br, CH₂CH₃, A33], [2771:CH₃, CH₃, A33], [2772:CH₃, CH₂CH₃, A33], [2773:CN, H, A33], [2774:CN, F, A33], [2775:CN, Cl, A33], [2776:CN, Br, A33], [2777:CN, CH₃, A33], [2778:CN, CH₂CH₃, A33], [2779:C(=O)OCH₃, H, A33], [2780:C(=O)OCH₃, F, A33], [2781:C(=O)OCH₃, Cl, A33], [2782:C(=O)OCH₃, Br, A33], [2783:C(=O)OCH₃, CH₃, A33], [2784:C(=O)OCH₃, CH₂CH₃, A33], [2785:C(=O)O(CH₃)₃, H, A33], [2786:C(=O)O(CH₃)₃, F, A33], [2787:C(=O)O(CH₃)₃, Cl, A33], [2788:C(=O)O(CH₃)₃, Br, A33], [2789:C(=O)O(CH₃)₃, CH₃, A33], [2790:C(=O)O(CH₃)₃, CH₂CH₃, A33], [2791:C(=O)NH₂, H, A33], [2792:C(=O)NH₂, F, A33], [2793:C(=O)NH₂, Cl, A33], [2794:C(=O)NH₂, Br, A33], [2795:C(=O)NH₂, CH₃, A33], [2796:C(=O)NH₂, CH₂CH₃, A33], [2797:C(=O)NH(CH₃), H, A33], [2798:C(=O)NH(CH₃), F, A33], [2799:C(=O)NH(CH₃), Cl, A33], [2800:C(=O)NH(CH₃), Br, A33], [2801:C(=O)NH(CH₃), CH₃, A33], [2802:C(=O)NH(CH₃), CH₂CH₃, A33], [2803:C(=O)NH(CH₂CH₃), H, A33], [2804:C(=O)NH(CH₂CH₃), F, A33], [2805:C(=O)NH(CH₂CH₃), Cl, A33], [2806:C(=O)NH(CH₂CH₃), Br, A33], [2807:C(=O)NH(CH₂CH₃), CH₃, A33], [2808:C(=O)NH(CH₂CH₃), CH₂CH₃, A33], [2809:C(=O)N(CH₃)₂, H, A33], [2810:C(=O)N(CH₃)₂, F, A33], [2811:C(=O)N(CH₃)₂, Cl, A33], [2812:C(=O)N(CH₃)₂, Br, A33], [2813:C(=O)N(CH₃)₂, CH₃, A33], [2814:C(=O)N(CH₃)₂, CH₂CH₃, A33], [2815:C(=S)OCH₃, H, A33], [2816:C(=S)OCH₃, F, A33], [2817:C(=S)OCH₃, Cl, A33], [2818:C(=S)OCH₃, Br, A33], [2819:C(=S)OCH₃, CH₃, A33], [2820:C(=S)OCH₃, CH₂CH₃, A33], [2821:C(=S)NH₂, H, A33], [2822:C(=S)NH₂, F, A33], [2823:C(=S)NH₂, Cl, A33], [2824:C(=S)NH₂, Br, A33], [2825:C(=S)NH₂, CH₃, A33], [2826:C(=S)NH₂, CH₂CH₃, A33], [2827:C(=S)NH(CH₃), H, A33], [2828:C(=S)NH (CH₃), F, A33], [2829:C(=S)NH(CH₃), Cl, A33], [2830:C(=S)NH(CH₃), Br, A33], [2831:C(=S)NH(CH₃), CH₃, A33], [2832:C(=S)NH(CH₃), CH₂CH₃, A33], [2833:C(=S)N(CH₃)₂, H, A33], [2834:C(=S)N(CH₃)₂, F, A33], [2835:C(=S)N(CH₃)₂, Cl, A33], [2836:C(=S)N(CH₃)₂, Br, A33], [2837:C(=S)N(CH₃)₂, CH₃, A33], [2838:C(=S)N(CH₃)₂, CH₂CH₃, A33], [2839:H, H, A34], [2840:H, F, A34], [2841:H, Cl, A34], [2842:H, Br, A34], [2843:H, CH₃, A34], [2844:H, CH₂CH₃, A34], [2845:F, F, A34], [2846:F, Cl, A34], [2847:F, Br, A34], [2848:F, CH₃, A34], [2849:F, CH₂CH₃, A34], [2850:Cl, Cl, A34], [2851:Cl, Br, A34], [2852:Cl, CH₃, A34], [2853:Cl, CH₂CH₃, A34], [2854:Br, Br, A34], [2855:Br, CH₃, A34], [2856:Br, CH₂CH₃, A34], [2857:CH₃, CH₃, A34], [2858:CH₃, CH₂CH₃, A34], [2859:CN, H, A34], [2860:CN, F, A34], [2861:CN, Cl, A34], [2862:CN, Br, A34], [2863:CN, CH₃, A34], [2864:CN, CH₂CH₃, A34], [2865:C(=O)OCH₃, H, A34], [2866:C(=O)OCH₃, F, A34], [2867:C(=O)OCH₃, Cl, A34], [2868:C(=O)OCH₃, Br, A34], [2869:C(=O)OCH₃, CH₃, A34], [2870:C(=O)OCH₃, CH₂CH₃, A34], [2871:C(=O)O(CH₃)₃, H, A34], [2872:C(=O)O(CH₃)₃, F, A34], [2873:C(=O)O(CH₃)₃, Cl, A34], [2874:C(=O)O(CH₃)₃, Br, A34], [2875:C(=O)O(CH₃), CH₃, A34], [2876:C(=O)O(CH₃)₃, CH₂CH₃, A34], [2877:C(=O)NH₂, H, A34], [2878:C(=O)NH₂, F, A34], [2879:C(=O)NH₂, Cl, A34], [2880:C(=O)NH₂, Br, A34], [2881:C(=O)NH₂, CH₃, A34], [2882:C(=O)NH₂, CH₂CH₃, A34], [2883:C(=O)NH(CH₃), H, A34], [2884:C(=O)NH(CH₃), F, A34], [2885:C(=O)NH(CH₃), Cl, A34], [2886:C(=O)NH(CH₃), Br, A34], [2887:C(=O)NH(CH₃), CH₃, A34], [2888:C(=O)NH(CH₃), CH₂CH₃, A34], [2889:C(=O)NH(CH₂CH₃), H, A34], [2890:C(=O)NH(CH₂CH₃), F, A34], [289:C(=O)NH(CH₂CH₃), Cl, A34], [2892:C(=O)NH(CH₂CH₃), Br, A34], [2893:C(=O)NH(CH₂CH₃), CH₃, A34], [2894:C(=O)NH(CH₂CH₃), CH₂CH₃, A34], [2895:C(=O)N(CH₃)₂, H, A34], [2896:C(=O)N(CH₃)₂, F, A34], [2897:C(=O)N(CH₃)₂, Cl, A34], [2898:C(=O)N(CH₃)₂, Br, A34], [2899:C(=O)N(CH₃)₂, CH₃, A34], [2900:C(=O)N(CH₃)₂, CH₂CH₃, A34], [2901:C(=S)OCH₃, H, A34], [2902:C(=S)OCH₃, F, A34], [2903:C(=S)OCH₃, Cl, A34], [2904:C(=S)OCH₃, Br, A34], [2905:C(=S)OCH₃, CH₃, A34], [2906:C(=S)OCH₃, CH₂CH₃, A34], [2907:C(=S)NH₂, H, A34], [2908:C(=S)NH₂, F, A34], [2909:C(=S)NH₂, Cl, A34], [2910:C(=S)NH₂, Br, A34], [2911:C(=S)NH₂, CH₃, A34], [2912:C(=S)NH₂, CH₂CH₃, A34], [2913:C(=S)NH(CH₃), H, A34], [2914:C(=S)NH(CH₃), F, A34], [2915:C(=S)NH(CH₃), Cl, A34], [2916:C(=S)NH(CH₃), Br, A34], [2917:C(=S)NH(CH₃), CH₃, A34], [2918:C(=S)NH(CH₃), CH₂CH₃, A34], [2919:C(=S)N(CH₃)₂, H, A34], [2920:C(=S)N(CH₃)₂, F, A34], [2921:C(=S)N(CH₃)₂, Cl, A34], [2922:C(=S)N(CH₃)₂, Br, A34], [2923:C(=S)N(CH₃)₂, CH₃, A34], [2924:C(=S)N(CH₃)₂, CH₂CH₃, A34], [2925:H, H, A35], [2926:H, F, A35], [2927:H, Cl, A35], [2928:H, Br, A35], [2929:H, CH₃, A35], [2930:H, CH₂CH₃, A35], [2931:F, F, A35], [2932:F, Cl, A35], [2933:F, Br, A35], [2934:F, CH₃, A35], [2935:F, CH₂CH₃, A35], [2936:Cl, Cl, A35], [2937:Cl, Br, A35], [2938:CH₃, A35], [2939:CH₂CH₃, A35], [2940:Br, Br, A35], [2941:Br, CH₃, A35], [2942:Br, CH₂CH₃, A35], [2943:CH₃, CH₃, A35], [2944:CH₃, CH₂CH₃, A35], [2945:CN, H, A35], [2946:CN, F, A35], [2947:CN, Cl, A35], [2948:CN, Br, A35], [2949:CN, CH₃, A35], [2950:CN, CH₂CH₃, A35], [2951:C(=O)OCH₃, H, A35], [2952:C(=O)OCH₃, F, A35], [2953:C(=O)OCH₃, Cl, A35], [2954:C(=O)OCH₃, Br, A35], [2955:C(=O)OCH₃, CH₃, A35], [2956:C(=O)OCH₃, CH₂CH₃, A35], [2957:C(=O)O(CH₃)₃, H, A35], [2958:C(=O)O(CH₃)₃, F, A35], [2959:C(=O)O(CH₃)₃, Cl, A35], [2960:C(=O)O(CH₃)₃, Br, A35], [2961:C(=O)O(CH₃)₃, CH₃, A35], [2962:C(=O)O(CH₃)₃, CH₂CH₃, A35], [2963:C(=O)NH₂, H, A35], [2964:C(=O)NH₂, F, A35], [2965:C(=O)NH₂, Cl, A35], [2966:C(=O)NH₂, Br, A35], [2967:C(=O)NH₂, CH₃, A35], [2968:C(=O)NH₂, CH₂CH₃, A35], [2969:C(=O)NH(CH₃), H, A35], [2970:C(=O)NH(CH₃), F, A35], [2971:C(=O)NH(CH₃), Cl, A35], [2972:C(=O)NH(CH₃), Br, A35], [2973:C(=O)NH(CH₃), CH₃, A35], [2974:C(=O)NH(CH₃), CH₂CH₃, A35], [2975:C(=O)NH(CH₂CH₃), H, A35], [2976:C(=O)NH(CH₂CH₃), F, A35], [2977:C(=O)NH(CH₂CH₃), Cl, A35], [2978:C(=O)NH(CH₂CH₃), Br, A35], [2979:C(=O)NH(CH₂CH₃), CH₃, A35], [2980:C(=O)NH(CH₂CH₃), CH₂CH₃, A35], [2981:C(=O)N(CH₃)₂, H, A35], [2982:C(=O)N(CH₃)₂, F, A35], [2983:C(=O)N(CH₃)₂, Cl, A35], [2984:C(=O)N(CH₃)₂, Br, A35], [2985:C(=O)N(CH₃)₂, CH₃, A35], [2986:C(=O)N(CH₃)₂, CH₂CH₃, A35], [2987:C(=S)OCH₃, H, A35], [2988:C(=S)OCH₃, F, A35], [2989:C(=S)OCH₃, Cl, A35], [2990:C(=S)OCH₃, Br, A35], [2991:C(=S)OCH₃, CH₃, A35], [2992:C(=S)OCH₃, CH₂CH₃, A35], [2993:C(=S)NH₂, H, A35], [2994:C(=S)NH₂, F, A35], [2995:C(=S)NH₂, Cl, A35], [2996:C(=S)NH₂, Br, A35], [2997:C(=S)NH₂, CH₃, A35], [2998:C(=S)NH₂, CH₂CH₃, A35], [2999:C(=S)NH(CH₃), H, A35], [3000:C(=S)NH(CH₃), F, A35], [3001:C(=S)NH(CH₃), Cl, A35], [3002:C(=S)NH(CH₃), Br, A35], [3003:C(=S)NH(CH₃), CH₃, A35], [3004:C(=S)NH(CH₃), CH₂CH₃, A35], [3005:C(=S)N(CH₃)₂, H, A35], [3006:C(=S)N(CH₃)₂, F, A35], [3007:C(=S)N(CH₃)₂, Cl, A35], [3008:C(=S)N(CH₃)₂, Br, A35], [3009:C(=S)N(CH₃)₂, CH₃, A35], [3010:C(=S)N(CH₃)₂, CH₂CH₃, A35], [3011:H, H, A36], [3012:H, F, A36], [3013:H, Cl, A36], [3014:H, Br, A36], [3015:H, CH₃, A36], [3016:H, CH₂CH₃, A36], [3017:F, F, A36], [3018:F, Cl, A36], [3019:F, Br, A36], [3020:F, CH₃, A36], [3021:F, CH₂CH₃, A36], [3022:Cl, Cl, A36], [3023:Cl, Br, A36], [3024:Cl, CH₃, A36], [3025:Cl, CH₂CH₃, A36], [3026:Br, Br, A36], [3027:Br, CH₃, A36], [3028:Br, CH₂CH₃, A36], [3029:CH₃, CH₃, A36], [3030:CH₃, CH₂CH₃, A36], [3031:CN, H, A36], [3032:CN, F, A36], [3033:CN, Cl, A36], [3034:CN, Br, A36], [3035:CN, CH₃, A36], [3036:CN, CH₂CH₃, A36], [3037:C(=O)OCH₃, H, A36], [3038:C(=O)OCH₃, F, A36], [3039:C(=O)OCH₃, Cl, A36], [3040:C(=O)OCH₃, Br, A36], [3041:C(=O)OCH₃, CH₃, A36], [3042:C(=O)OCH₃, CH₂CH₃, A36], [3043:C(=O)O(CH₃)₃, H, A36], [3044:C(=O)O(CH₃)₃, F, A36], [3045:C(=O)O(CH₃)₃, Cl, A36], [3046:C(=O)O(CH₃)₃, Br, A36], [3047:C(=O)O(CH₃)₃, CH₃, A36], [3048:C(=O)O(CH₃)₃, CH₂CH₃, A36], [3049:C(=O)NH₂, H, A36], [3050:C(=O)NH₂, F, A36], [3051:C(=O)NH₂, Cl, A36], [3052:C(=O)NH₂, Br, A36], [3053:C(=O)NH₂, CH₃, A36], [3054:C(=O)NH₂, CH₂CH₃, A36], [3055:C(=O)NH(CH₃), H, A36], [3056:C(=O)NH(CH₃), F, A36], [3057:C(=O)NH(CH₃), Cl, A36], [3058:C(=O)NH(CH₃), Br, A36], [3059:C(=O)NH(CH₃), CH₃, A36], [3060:C(=O)NH(CH₃), CH₂CH₃, A36], [3061:C(=O)NH(CH₂CH₃), H, A36], [3062:C(=O)NH(CH₂CH₃), F, A36], [3063:C(=O)NH(CH₂CH₃), Cl, A36], [3064:C(=O)NH(CH₂CH₃), Br, A36], [3065:C(=O)NH(CH₂CH₃), CH₃, A36], [3066:C(=O)NH(CH₂CH₃), CH₂CH₃, A36], [3067:C(=O)N(CH₃)₂, H, A36], [3068:C(=O)N(CH₃)₂, F, A36], [3069:C(=O)N(CH₃)₂, Cl, A36], [3070:C(=O)N(CH₃)₂, Br, A36], [3071:C(=O)N(CH₃)₂, CH₃, A36], [3072:C(=O)N(CH₃)₂, CH₂CH₃, A36], [3073:C(=S)OCH₃, H, A36],

[3074:C(=S)OCH₃, F, A36], [3075:C(=S)OCH₃, Cl, A36], [3076:C(=S)OCH₃, Br, A36], [3077:C(=S)OCH₃, CH₃, A36], [3078:C(=S)OCH₃, CH₂CH₃, A36], [3079:C(=S)NH₂, H, A36], [3080:C(=S)NH₂, F, A36], [3081:C(=S)NH₂, Cl, A36], [3082:C(=S)NH₂, Br, A36], [3083:C(=S)NH₂, CH₃, A36], [3084:C(=S)NH₂, CH₂CH₃, A36], [3085:C(=S)NH(CH₃), H, A36], [3086:C(=S)NH(CH₃), F, A36], [3087:C(=S)NH(CH₃), Cl, A36], [3088:C(=S)NH(CH₃), Br, A36], [3089:C(=S)NH(CH₃), CH₃, A36], [3090:C(=S)NH(CH₃), CH₂CH₃, A36], [3091:C(=S)N(CH₃)₂, H, A36], [3092:C(=S)N(CH₃)₂, F, A36], [3093:C(=S)N(CH₃)₂, Cl, A36], [3094:C(=S)N(CH₃)₂, Br, A36], [3095:C(=S)N(CH₃)₂, CH₃, A36], [3096:C(=S)N(CH₃)₂, CH₂CH₃, A36].

In the above combinations, symbols A1 to A36 represent the following 6-membered aromatic heterocyclic groups.

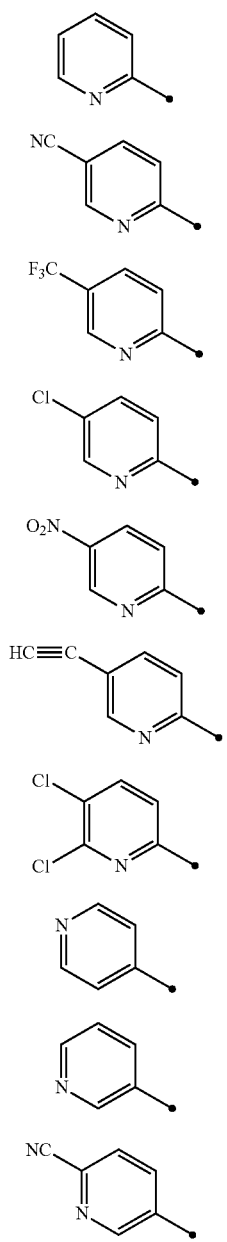

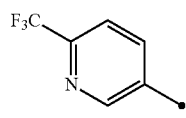 A11

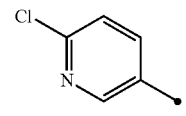 A12

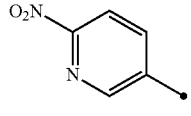 A13

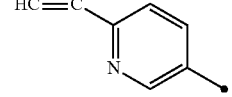 A14

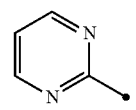 A15

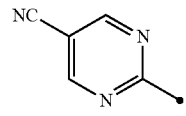 A16

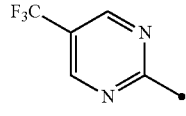 A17

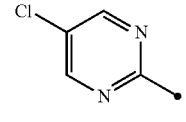 A18

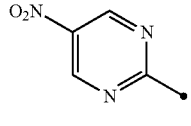 A19

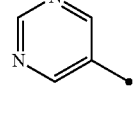 A20

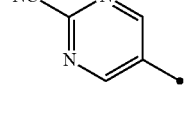 A21

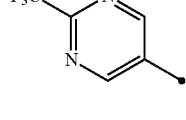 A22

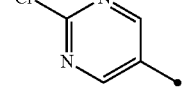 A23

-continued

A24 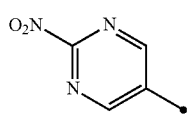

A25 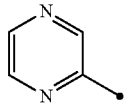

A26 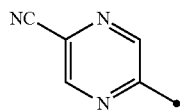

A27 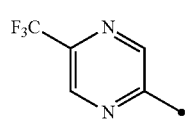

A28 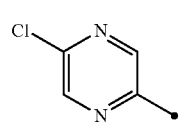

A28 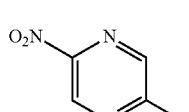

A29 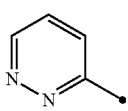

A30 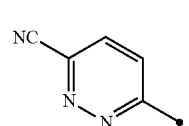

A31 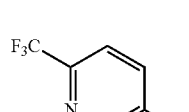

A32 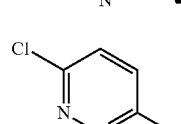

A33 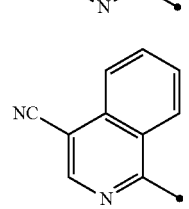

A34 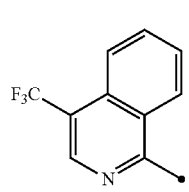

-continued

A35 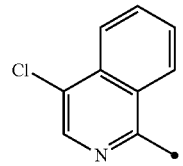

A36 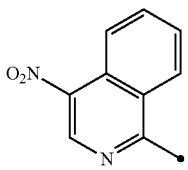

Among the compounds defined by combinations of the above formulas ($I^1$) to ($I^{45}$) with $R^1$, $R^2$ and A, the compound ($I^1$-19) and the compound ($I^{12}$-2259) show the following compounds.

($I^1$-19)

($I^{12}$-2259)

Production Examples of intermediates of the present compound are shown as Reference Production Examples.

REFERENCE PRODUCTION EXAMPLE 1

In 50 mL of tetrahydrofuran, 1.00 g of 2-trifluoromethylpyridine-5-carboaldehyde was dissolved and 6.9 mL of methyl magnesium bromide (1M tetrahydrofuran solution) was added dropwise thereto at −78° C. After stirring at the same temperature for 2 hours and heating to room temperature, the solution was further stirred for 10 hours. To the reaction mixture was added 10% hydrochloric acid, followed by extraction with ethyl acetate. The organic layer was dried over anhydrous magnesium sulfate and concentrated under reduced pressure, and then the resulting residue was dissolved in 20 mL of tetrahydrofuran. 0.5 mL of methanesulfonyl chloride and 0.8 mL of triethylamine were added at room temperature. After stirring at the same temperature for one hour, 10% hydrochloric acid was added, followed by extraction with ethyl acetate. The organic layer was dried over anhydrous magnesium sulfate and concentrated under reduced pressure, and then the resulting residue was dissolved in 20 mL of N,N-dimethylformamide. To the solution was added 1.0 g of lithium bromide at room temperature. After stirring at the same temperature for 3 hours, 10% hydrochloric acid was added, followed by extraction with ethyl acetate. The organic layer was dried over anhydrous magnesium sulfate and concentrated under reduced pressure, and then the resulting residue was subjected to column chromatography to obtain 0.22 g of 5-(1-bromoethyl)-2-trifluoromethylpyridine.

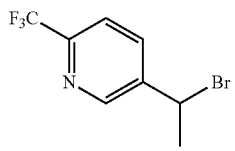

$^1$H-NMR (CDCl$_3$, TMS): δ(ppm) 8.75 (1H, s), 7.96 (1H, d), 7.69 (1H, d), 5.14 (1H, q), 1.89 (3H, d)

REFERENCE PRODUCTION EXAMPLE 2

In 70 mL of tetrahydrofuran, 4.44 g of (5-trifluoromethylpyridin-2-yl)methanol was dissolved and 1.9 mL of methanesulfonyl chloride and 3.5 mL of triethylamine were added dropwise at 0° C. After stirring at the same temperature for 0.5 hours, 10% hydrochloric acid was added, followed by extraction with ethyl acetate. The organic layer was dried over anhydrous magnesium sulfate and concentrated under reduced pressure, and then the resulting residue was dissolved in 30 mL of N,N-dimethylformamide.

To the solution was added 4.4 g of lithium bromide at room temperature. The reaction mixture was heated to 90° C. and, after stirring for 10 minutes and returning to room temperature, 10% hydrochloric acid was added, followed by extraction with ethyl acetate. The organic layer was dried over anhydrous magnesium sulfate and concentrated under reduced pressure, and then the resulting residue was subjected to column chromatography to obtain 1.68 g of 2-bromomethyl-5-trifluoromethylpyridine.

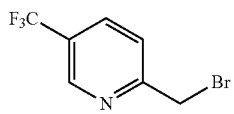

$^1$H-NMR (CDCl$_3$, TMS): δ(ppm) 8.84 (1H, s), 7.94 (1H, dd), 7.59 (1H, d), 4.59 (2H, s)

REFERENCE PRODUCTION EXAMPLE 3

In 50 mL of methanol, 243 mg of sodium borohydride was suspended and 1.00 g of 2-acetyl-5-chloropyridine was added thereto at room temperature. After stirring at the same temperature for 2 hours, 10% hydrochloric acid was added, followed by extraction with ethyl acetate. The organic layer was dried over anhydrous magnesium sulfate and concentrated under reduced pressure, and then the resulting residue was dissolved in 50 mL of tetrahydrofuran. To the solution were added dropwise 0.5 mL of methanesulfonyl chloride and 0.9 mL of triethylamine at room temperature. After stirring at the same temperature for 2 hours, 10% hydrochloric acid was added, followed by extraction with ethyl acetate. The organic layer was dried over anhydrous magnesium sulfate and concentrated under reduced pressure, and then the resulting residue was dissolved in 50 mL of N,N-dimethylformamide. To the solution was added 1.12 g of lithium bromide at room temperature. After stirring at the same temperature for 6 hours, 10% hydrochloric acid was added, followed by extraction with ethyl acetate. The organic layer was dried over anhydrous magnesium sulfate and concentrated under reduced pressure, and then the resulting residue was subjected to column chromatography to obtain 368 mg of 2-(1-bromoethyl)-5-chloropyridine.

$^1$H-NMR (CDCl$_3$, TMS): δ(ppm) 8.25 (1H, s), 7.66 (1H, d), 7.42 (1H, d), 5.12 (1H, q), 1.87 (3H, d)

FORMULATION EXAMPLE 1

Nine parts of any one of the present compounds (1) to (15) is dissolved in 37.5 parts of xylene and 37.5 parts of dimethylformamide, and 10 parts of polyoxyethylene styryl phenyl ether and 6 parts of calcium dodecylbenzene sulfonate are added thereto, followed by thoroughly mixing to obtain an emulsifiable concentrate.

FORMULATION EXAMPLE 2

Five parts of the present compound (1) and 4 parts of a compound selected from the following group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

The group [A]:

aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos;

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb;

acrinathrin, allethrin, beta-cyfluthrin, bifenthrin, cycloprothrin, cyfluthrin, cyhalothrin, empenthrin, deltamethrin, esfenvalerate, ethofenprox, fenvalerate, flucythrinate, flufenoprox, flumethrin, fluvalinate, halfenprox, imiprothrin, prallethrin, pyrethrins, resmethrin, sigma-cypermethrin, silafluofen, tefluthrin, tralomethrin, transfluthrin, tetramethrin, lambda-cyhalothrin, gamma-cyhalothrin, furamethrin, tau-fluvalinate, 2,3,5,6-tetrafluoro-4-methylbenzyl2,2-dimethyl-3-(1-propenyl)cyclopropanecarboxylate, 2,3,5,6-tetrafluoro-4-(methoxymethyl)benzyl2,2-dimethyl-3-(2-methyl-1-propenyl) cyclopropanecarboxylate, 2,3,5,6-tetrafluoro-4-(methoxymethyl)benzyl2,2-dimethyl-3-(2-cyano-1-propenyl)cyclopropanecarboxylate, 2,3,5,6-tetrafluoro-4-(methoxymethyl)benzyl2,2,3,3-tetramethylcyclopropanecarboxylate;

cartap, bensultap, thiocyclam, monosultap, bisultap;

imidacloprid, nitenpyram, acetamiprid, thiamethoxam, thiacloprid;

chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron;

acetoprole, fipronil, vaniliprole, pyriprole, pyrafluprole, and the like;

chromafenozide, halofenozide, methoxyfenozide, tebufenozide;

aldrin, dieldrin, dienochlor, endosulfan, methoxychlor;

nicotine sulfate;

avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide; potassium oleate, protrifenbute, spiromesifen, sulfur, metaflumizone, spirotetramat, pyrifluquinazone, chlorantraniliprole, tralopyril, a compound represented by the following formula (A):

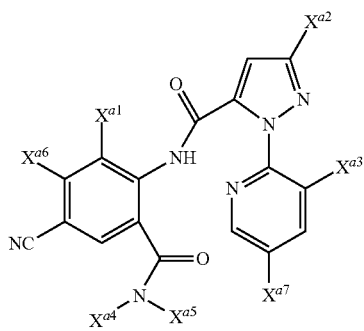

(A)

wherein $X^{a1}$ represents a methyl group, a chlorine atom, a bromine atom or a fluorine atom, $X^{a2}$ represents a fluorine atom, a chlorine atom, a bromine atom, a C1-C4 haloalkyl group or a C1-C4 haloalkoxy group, $X^{a3}$ represents a fluorine atom, a chlorine atom or a bromine atom, $X^{a4}$ represents an optionally substituted C1-C4 alkyl group, an optionally substituted C3-C4 alkenyl group, an optionally substituted C3-C4 alkynyl group, an optionally substituted C3-C5 cycloalkyl group or a hydrogen atom, $X^{a5}$ represents a hydrogen atom or a methyl group, $X^{a6}$ represents a hydrogen atom, a fluorine atom or a chlorine atom, and $X^{a7}$ represents a hydrogen atom, a fluorine atom or a chlorine atom;

a compound represented by the following formula (B):

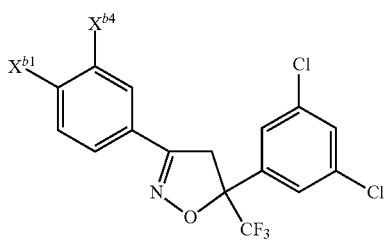

(B)

wherein $X^{b1}$ represents a $X^{b2}$—NH—C(=O) group, a $X^{b2}$—C(=O)—NH—CH$_2$— group, a $X^{b3}$—S(O) group, an optionally substituted pyrrol-1-yl group, an optionally substituted imidazol-1-yl group, an optionally substituted pyrazol-1-yl group, or an optionally substituted 1,2,4-triazol-1-yl group, $X^{b2}$ represents an optionally substituted C1-C4 haloalkyl group such as a 2,2,2-trifluoroethyl group or an optionally substituted C3-C6 cycloalkyl group such as a cyclopropyl group, $X^{b3}$ represents an optionally substituted C1-C4 alkyl group such as a methyl group, and $X^{b4}$ represents a hydrogen atom, a chlorine atom, a cyano group or a methyl group;

a compound represented by the following formula (C):

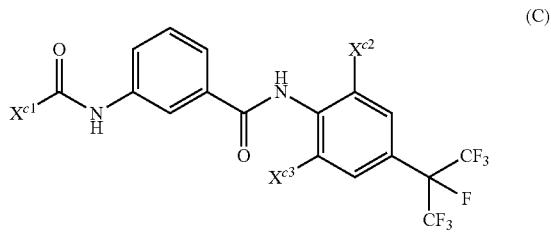

(C)

wherein $X^{c1}$ represents an optionally substituted C1-C4 alkyl group such as a 3,3,3-trifluoropropyl group, an optionally substituted C1-C4 alkoxy group such as a 2,2,2-trichloroethoxy group or an optionally substituted phenyl group such as a 4-cyanophenyl group or an optionally substituted pyridyl group such as a 2-chloro-3-pyridyl group, $X^{c2}$ represents a methyl group or a trifluoromethylthio group, and $X^{c3}$ represents a methyl group or a halogen atom;

acequinocyl, amitraz, benzoximate, bifenazate, bromopropylate, chinomethionat, chlorobenzilate, CPCBS (chlorfenson), clofentezine, cyflumetofen, kelthane (dicofol), fenbutatin oxide, fenothiocarb, fenpyroximate, fluacrypyrim, fluproxyfen, hexythiazox, propargite (BPPS), pyridaben, pyrimidifen, tebufenpyrad, tetradifon, spirodiclofen, spiromesifen, spirotetramat, amidoflumet, and cyenopyrafen.

FORMULATION EXAMPLE 3

Five parts of the present compound (2) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 4

Five parts of the present compound (3) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 5

Five parts of the present compound (4) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 6

Five parts of the present compound (5) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 7

Five parts of the present compound (6) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 8

Five parts of the present compound (7) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 9

Five parts of the present compound (8) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 10

Five parts of the present compound (9) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 11

Five parts of the present compound (10) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 12

Five parts of the present compound (11) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 13

Five parts of the present compound (12) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 14

Five parts of the present compound (13) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 15

Five parts of the present compound (14) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 16

Five parts of the present compound (15) and 4 parts of a compound selected from the group [A] are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

FORMULATION EXAMPLE 17

To 40 parts of any one of the present compounds (1) to (15) is added 5 parts of Sorpol® 5060 (Toho Chemical Industry Co., Ltd.), followed by thoroughly mixing, adding 32 parts of CARPLEX® #80 (SHIONOGI & CO., LTD., fine synthetic hydrous silicon oxide powders) and 23 parts of 300 mesh diatomaceous earth, and further mixing with a juice mixer to obtain a wettable powder.

FORMULATION EXAMPLE 18

Three parts of any one of the present compounds (1) to (15), 5 parts of a synthesized hydrous silicon oxide powder, 5 parts of sodium dodecylbenzene sulfonate, 30 parts of bentonite and 57 parts of clay are thoroughly mixed with stirring. Then, an appropriate amount of water is added thereto, followed by stirring, granulating with a granulator and further air-drying to obtain granules.

FORMULATION EXAMPLE 19

In a mortar, 4.5 parts of any one of the present compounds (1) to (15), 1 part of a synthesized hydrous silicon oxide powder, 1 part of DORILESS B (manufactured by Sankyo Co., Ltd.) as a coagulant and 7 parts of clay are thoroughly mixed, and the mixture is further stirred with a juice mixer. To the resultant mixture, 86.5 parts of cut clay is added, followed by thoroughly mixing to obtain dusts.

FORMULATION EXAMPLE 20

Ten parts of any one of the present compounds (1) to (15), 35 parts of white carbon containing 50 parts of a polyoxyethylene alkyl ether sulfate ammonium salt and 55 parts of water are mixed and finely ground by a wet grinding method to obtain a formulation.

FORMULATION EXAMPLE 21

In 10 parts of dichloromethane, 0.5 part of any one of the present compounds (1) to (15) is dissolved and then the solution is mixed with 89.5 parts of ISOPAR M (Isoparaffin®: Exxon Chemical Co., Ltd.) to obtain an oil solution.

FORMULATION EXAMPLE 22

Into an aerosol can, 0.1 part of any one of the present compound (1) to (15) and 49.9 parts of Neothiozole (Chuo Kasei Co., Ltd.) are poured. After mounting an aerosol valve, 25 parts of dimethylether and 25 parts of LPG are added, followed by shaking and further mounting an actuator to obtain an oily aerosol.

FORMULATION EXAMPLE 23

A solution prepared by dissolving 0.6 part of any one of the present compounds (1) to (15), 0.01 part of BHT, 5 parts of xylene, 3.39 parts of deodorized kerosine and 1 part of an emulsifier {Atomos® 300 (Atomos Chemical Co., Ltd.)} with mixing and 50 parts of distilled water are poured into an aerosol container and a valve part is attached, and then 40 parts of a propellant (LPG) is added under pressure through the valve to obtain an aqueous aerosol.

FORMULATION EXAMPLE 24

Five parts of any one of the present compounds (1) to (15) is dissolved in 80 parts of diethylene glycol monoethyl ether. Thereto 15 parts of propylene carbonate is mixed to obtain a spot-on liquid formulation.

FORMULATION EXAMPLE 25

Ten parts of any one of the present compounds (1) to (15) is dissolved in 70 parts of diethylene glycol monoethyl ether. Thereto 20 parts of 2-octyldodecanol is mixed to obtain a pour-on liquid formulation.

FORMULATION EXAMPLE 26

To 0.5 parts of any one of the present compounds (1) to (15) are added 60 parts of NIKKOL TEALS-42 (a 42% aqueous solution of triethanolamine lauryl sulfate, Nikko Chemicals) and 20 parts of propylene glycol. The mixture is stirred well to obtain a homogeneous solution. Thereto 19.5 parts of water is added and mixed by stirring thoroughly to obtain a homogeneous shampoo formulation.

FORMULATION EXAMPLE 27

A porous ceramic plate with a length of 4.0 cm, a width of 0.4 cm and a thickness of 1.2 cm is impregnated with a solution of 0.1 g of any one of the present compounds (1) to (15) in 2 ml of propylene glycol to obtain a heating-type smoking pesticide.

FORMULATION EXAMPLE 28

Five parts of any one of the present compounds (1) to (15) and 95 parts of an ethylene-methyl methacrylate copolymer (the proportion of methyl methacrylate in the copolymer: 10% by weight, ACRYFT WD301, Sumitomo Chemical) are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

FORMULATION EXAMPLE 29

Five parts of any one of the present compounds (1) to (15) and 95 parts of a flexible polyvinyl chloride resin are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

The following Test Examples shows that the present compounds are effective as an active ingredient of a pesticidal composition. The present compounds are represented by the above compound number.

TEST EXAMPLE 1

Each of the formulations of the present compounds (1), (2), (3), (4), (6), (8), (9), (12), (14) and (15) obtained in Formulation Example 20 was diluted so that the concentration of the present compound was 500 ppm to prepare a test solution.

In a polyethylene cup, 50 g of a culture soil BONSOL 2 (manufactured by Sumitomo Chemical Co., Ltd.) was put and 10 to 15 seeds of a rice plant were seeded. After growing until second true leaves were developed, the test solution thus prepared was sprayed to the rice plant with a uniform cut height of 5 cm at the proportion of 20 mL/cup. After the test solution sprayed over the rice plant was dried, the rice plant was put in a plastic cup so as to prevent escape of a test insect and 30 *Nilaparvata lugens* larvae were released and then allowed to stand in a greenhouse at 25° C. Six days after releasing *Nilaparvata lugens* larvae, the number of *Nilaparvata lugens* parasitic on the rice plant was examined after 6 days.

As a result, the number of insects parasitic on the rice plant was 3 or less when the rice plant was treated with any one of the present compounds (1), (2), (3), (4), (6), (8), (9), (12), (14) and (15).

TEST EXAMPLE 2

Each of the formulations of the present compounds (1), (2), (3), (4), (6), (8), (9), (10), (14) and (15) obtained in Formulation Example 20 was diluted so that the concentration of the present compound was 55.6 ppm to prepare a test solution.

In a polyethylene cup provided with 5 holes having a diameter of 5 mm at the bottom, 50 g of a culture soil BONSOL 2 (manufactured by Sumitomo Chemical Co., Ltd.) was put and 10 to 15 seeds of a rice plant were seeded. After growing until second true leaves were developed, the rice plant was treated with 45 mL of the test solution absorbed from the bottom of the cup. The rice plant was allowed to stand in a greenhouse at 25° C. for 6 days and the height of the rice plant was adjusted to 5 cm by cutting and, after releasing 30 *Nilaparvata lugens* larvae, the number of *Nilaparvata lugens* parasitic on the rice plant was examined after 6 days.

Six days after the treatment, the number of insects being parasitic on the rice plant was 3 or less when the rice plant was treated with any one of the present compounds (1), (2), (3), (4), (6), (8), (9), (10), (14) and (15).

TEST EXAMPLE 3

Each of the formulations of the present compounds (1), (2), (3), (4), (5), (6), (8), (9), (10), (12), (14) and (15) obtained in Formulation Example 20 was diluted so that the concentration of the present compound was 500 ppm to prepare a test solution.

On the bottom of a polyethylene cup having a diameter of 5.5 cm, a filter paper having the same size was laid and 0.7 mL of the test solution was dropped on the filter paper, and then 30 mg of a sucrose as a bait was uniformly placed. In the polyethylene cup, 10 female *Musca domesticas* were released and the cup was lidded. After 24 hours, life and death of *Musca domesticas* were examined and the mortality rate was determined.

As a result, the mortality rate was 90% or more by the treatment of the present compounds (1), (2), (3), (4), (5), (6), (8), (9), (10), (12), (14) and (15).

TEST EXAMPLE 4

Each of the formulations of the present compounds (1), (2), (3), (4), (5), (6), (8), (9), (10), (11), (14) and (15) obtained in Formulation Example 20 was diluted so that the concentration of the present compound was 500 ppm to prepare a test solution.

On the bottom of a polyethylene cup having a diameter of 5.5 cm, a filter paper having the same size was laid and 0.7 mL of the test solution was dropped on the filter paper, and then 30 mg of a sucrose as a bait was uniformly placed. In the polyethylene cup, 2 male adult *Blattalla germanica* were released and the cup was lidded. After 6 days, life and death of *Blattalla germanicas* were examined and the mortality rate was determined.

As a result, the mortality rate was 100% by the treatment of the present compounds (1), (2), (3), (4), (5), (6), (8), (9), (10), (11), (14) and (15).

TEST EXAMPLE 5

Each of the formulations of the present compounds (1), (3), (4), (6), (8), (9), (10), (14) and (15) obtained in Formulation Example 20 was diluted so that the concentration of the present compound was 500 ppm to prepare a test solution.

To 100 mL of ion-exchange water was added 0.7 mL of the above test solution (concentration of an active ingredient: 3.5 ppm). In the solution, 20 *Culex pipiens* pallens last instar larvae were released. After one day, life and death of *Culex pipiens* last instar larvae were examined and the mortality rate was determined.

As a result, the mortality rate was 95% or more by the treatment of the present compounds (1), (3), (4), (6), (8), (9), (10), (14) and (15).

Industrial Applicability

The compound of the present invention is useful as an active ingredient of a pesticidal composition.

The invention claimed is:

1. A fluorine-containing organosulfur compound represented by the formula (I):

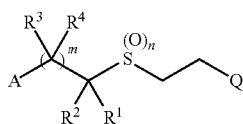

(I)

wherein m represents 0 or 1;
n represents 0, 1 or 2;
A represents a 6-membered aromatic heterocyclic group optionally substituted with a group of the groups E1 to E2;

$R^1$ and $R^3$ are the same or different and represent a C1-C4 chain hydrocarbon group optionally substituted with a halogen atom, a —C(=G)$R^5$ group, a cyano group, a halogen atom or a hydrogen atom;

$R^2$ and $R^4$ are the same or different and represent a C1-C4 chain hydrocarbon group optionally substituted with a halogen atom, a halogen atom, or a hydrogen atom;

Q represents a C1-C5 haloalkyl group containing at least one fluorine atom, or a fluorine atom;

G represents an oxygen atom or a sulfur atom;

$R^5$ represents a C1-C4 alkyl group optionally substituted with a halogen atom, a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, or a hydrogen atom;

the group E1 is a monovalent group selected from the group consisting of a C1-C6 chain hydrocarbon group optionally substituted with a group of the group L, a C3-C6 cycloalkyl group optionally substituted with a halogen atom, —OR$^6$, —SR$^6$, —S(=O)R$^6$, —S(=O)$_2$R$^6$, —C(=O)R$^7$, —OC(=O)R$^8$, a halogen atom, a cyano group, a nitro group and a hydroxyl group;

the group E2 is a divalent group selected from the group consisting of a C2-C6 alkanediyl group optionally substituted with a group of the group L, a 1,3-butadiene-1,4-diyl group optionally substituted with a group of the group L, -G-T-G- and -T-G-T-;

T represents a methylene group or an ethylene group;

$R^6$ represents a C1-C4 chain hydrocarbon group optionally substituted with a halogen atom or a C3-C6 cycloalkyl group optionally substituted with a halogen atom;

$R^7$ represents a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, a C1-C4 alkyl group optionally substituted with a halogen atom, or a hydrogen atom;

$R^8$ represents a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl) amino group optionally with a halogen atom, a C2-C5 cyclic amino group, a C1-C4 alkyl group optionally substituted with a halogen atom, or a hydrogen atom; and the group L is a monovalent group selected from the group consisting of a hydroxyl group, —OR$^6$, —SR$^6$, —S(=O)R$^6$, —S(=O)$_2$R$^6$, —C(=O)R$^7$, —OC(=O)R$^8$, a cyano group, a nitro group and a halogen atom.

2. The fluorine-containing organosulfur compound according to claim 1, wherein m is 0.

3. The fluorine-containing organosulfur compound according to claim 1, wherein m is 1.

4. The fluorine-containing organosulfur compound according to claim 1, wherein n is 0.

5. The fluorine-containing organosulfur compound according to claim 1, wherein n is 1 or 2.

6. The fluorine-containing organosulfur compound according to claim 1, wherein A represents a pyridyl group, a pyridazinyl group, a pyrimidinyl group or a pyrazinyl group, and the pyridyl group, the pyridazinyl group, the pyrimidinyl group or the pyrazinyl group may be substituted with a group of the groups E1 to E2.

7. The fluorine-containing organosulfur compound according to claim 1, wherein A represents a pyridyl group optionally substituted with a group E3, a pyridazinyl group optionally substituted with a group E3, a pyrimidinyl group optionally substituted with a group E3, or a pyrazinyl group optionally substituted with a group E3, and the group E3 is a monovalent group selected from the group consisting of a halogen atom, a trifluoromethyl group, a pentafluoroethyl group, an ethynyl group, a cyano group, a nitro group, a trifluoromethoxy group, a trifluoromethylthio group, a trifluoromethanesulfinyl group, a trifluoromethanesulfonyl group, a methylthio group, a methanesulfinyl group and a methanesulfonyl group.

8. A pesticidal composition comprising the fluorine-containing organosulfur compound according to claim 1 as an active ingredient.

9. A pest control method which comprises applying an effective amount of the compound according to claim 1 to pests or habitats of pestss.

* * * * *